(12) United States Patent
Ajjawi

(10) Patent No.: US 11,098,328 B2
(45) Date of Patent: Aug. 24, 2021

(54) ALGAL LIPID PRODUCTIVITY VIA GENETIC MODIFICATION OF A SIGNALING PROTEIN

(71) Applicant: Synthetic Genomics, Inc., La Jolla, CA (US)

(72) Inventor: Imad Ajjawi, San Diego, CA (US)

(73) Assignee: Synthetic Genomics, Inc., La Jolla, CA (US)

( * ) Notice: Subject to any disclaimer, the term of this patent is extended or adjusted under 35 U.S.C. 154(b) by 25 days.

(21) Appl. No.: 16/209,655

(22) Filed: Dec. 4, 2018

(65) Prior Publication Data

US 2019/0169627 A1 Jun. 6, 2019

Related U.S. Application Data

(60) Provisional application No. 62/594,930, filed on Dec. 5, 2017.

(51) Int. Cl.
*C12P 7/64* (2006.01)
*C12N 15/82* (2006.01)
*C07K 14/405* (2006.01)

(52) U.S. Cl.
CPC .............. *C12P 7/64* (2013.01); *C07K 14/405* (2013.01); *C12N 15/8247* (2013.01); *C12N 15/8216* (2013.01)

(58) Field of Classification Search
None
See application file for complete search history.

(56) References Cited

U.S. PATENT DOCUMENTS

| 8,822,162 B2 * | 9/2014 | Ulijasz | G01N 33/542 435/7.1 |
|---|---|---|---|
| 2013/0259924 A1 | 10/2013 | Bancel et al. | |
| 2014/0230087 A1 | 8/2014 | Hartig et al. | |
| 2014/0273231 A1 | 9/2014 | Zhang et al. | |
| 2015/0056646 A1 * | 2/2015 | Ulijasz | C12Q 1/02 435/29 |
| 2016/0264980 A1 | 9/2016 | Abad et al. | |
| 2017/0067069 A1 | 3/2017 | Bauman et al. | |

OTHER PUBLICATIONS

Nature Editorial (Microbiology by numbers published 2011) (Year: 2011).*
Guiry (How Many Species of Algae Are There. J. Phycol. 48, 1057-1063, 2012) (Year: 2012).*
Corteggiani et al (Chromosome scale genome assembly and transcriptome profiling of Nannochloropsis gaditana in nitrogen depletion. Mol Plant. 7: 323-335, 2014) (Year: 2014).*
Carpinelli, C. E. et al.: "*Chromosome Scale Genome Assembly and Transcriptome Profiling of Nannochloropsis gaditana in Nitrogen Depletion*"; Molecular Plant, Feb. 2014, vol. 7, No. 2; pp. 323-335.
Dietrich, F. S. et al.: "*The Ashbya gossypii genome as a tool for mapping the ancient Saccharomyces cerevisiae genome*"; Science, Apr. 9, 2004, vol. 304, pp. 304-307.
Duanmu, Deqiang et al.: "*Marine algae and land plants share conserved phytochrome signaling systems*"; PNAS, Nov. 4, 2014, vol. 111, No. 44, pp. 15827-15832.
International Search Report dated May 1, 2019, regarding PCT/US2018/063717.
Matthijs, M. et al.: "*Profiling of the Early Nitrogen Stress Response in the Diatom Phaeodactylum tricornutum Reveals a Novel Family of RING-Domain Transcription Factors*"; Plant Physiology, Jan. 2016, vol. 170, No. 1; pp. 489-498.
Radakovits, R. et al.: "*Genetic Engineering of Algae for Enhanced Biofuel Production*"; Eukaryotic Cell, Apr. 2010, vol. 9, No. 4; pp. 486-501.
Sanz-Luque, E et al.: "*Understanding nitrate assimilation and its regulation in microalgae*"; Frontiers in Plant Science, Oct. 26, 2015, vol. 6, No. 899; 17 pages.
Yang, Jain-Chao et al.: Deficiency of Phytochrome B Alleviates Chilling-Induced Photoinhibition in Rice[1]; Am J. of Botany, 2013, 100(9), pp. 1860-1870.

* cited by examiner

*Primary Examiner* — Ashley K Buran
*Assistant Examiner* — Wayne Zhong
(74) *Attorney, Agent, or Firm* — DLA Piper LLP (US)

(57) ABSTRACT

The present invention provides mutant microorganisms having attenuated expression of a gene encoding a polypeptide that includes a GAF domain wherein the mutant microorganisms have higher lipid productivity and/or exhibit increased partitioning of carbon to lipid as compared to wild-type microorganisms from which they are derived. Also provided are methods of producing lipids using the mutant microorganisms, guide RNAs, and nucleic acid constructs used for producing mutant microorganisms.

27 Claims, 6 Drawing Sheets
Specification includes a Sequence Listing.

US 11,098,328 B2

ALGAL LIPID PRODUCTIVITY VIA GENETIC MODIFICATION OF A SIGNALING PROTEIN

CROSS-REFERENCE TO RELATED APPLICATIONS

This application claims benefit of priority under 35 U.S.C. § 119(e) of U.S. Ser. No. 62/594,930, filed Dec. 5, 2017, the entire contents of which is incorporated herein by reference in its entirety.

INCORPORATION OF SEQUENCE LISTING

The material in the accompanying sequence listing is hereby incorporated by reference into this application. The accompanying sequence listing text file, name SGI2120_1_Sequence_Listing.txt, was created on Nov. 19, 2018, and is 34 kb. The file can be accessed using Microsoft Word on a computer that uses Windows OS.

FIELD OF THE DISCLOSURE

The invention relates to mutant microorganisms, such as algae and heterokonts, having increased lipid productivity and methods of their use in producing lipids.

Various attempts to improve lipid productivity by increasing lipid biosynthesis have focused on manipulating genes encoding enzymes for nitrogen assimilation or lipid metabolism or genes encoding polypeptides involved in lipid storage. For example, US2014/0162330 discloses a *Phaeodactylum tricornutum* strain in which the nitrate reductase (NR) gene has been attenuated by RNAi-based knockdown; Trentacoste et al. ((2013) *Proc. Natl. Acad. Sci. USA* 110:19748-19753) disclose diatoms transformed with an RNAi construct targeting the Thaps3_264297 gene predicted to be involved in lipid catabolism; and WO2011127118 discloses transformation of *Chlamydomonas* with genes encoding oleosins (lipid storage proteins) as well as with genes encoding diacylglycerol transferase (DGAT) genes. Although in each case increased lipid production was asserted based on microscopy or staining with lipophilic dyes, no quantitation of lipid production by the manipulated cells was provided, nor was lipid productivity over time determined.

Daboussi et al. 2014 (*Nature Comm.* 5:3881) report that disruption of the UGPase gene in *Phaeodactylum triconornutum*, which is believed to provide precursors to laminarin (a storage carbohydrate) synthesis, results in increased lipid accumulation. However, no biochemical data was shown to indicate that laminarin content was affected (or even present) and lipid and biomass productivities were not reported. Similarly, several groups have reported increases in lipid accumulation in *Chlamydomonas* starchless mutants (Wang et al. 2009 *Eukaryotic Cell* 8:1856-1868; Li et al. 2010 *Metab Eng.* 12:387-391) however, successive reports that actually measured lipid productivity concluded that these strains were impaired in growth when grown in phototrophic conditions (Siaut et al. 2011 *BMC Biotechnol.* 11:7; Davey et al. 2014 *Eukaryot Cell* 13:392-400). These reports concluded that the highest lipid productivities (measured as TAG per liter per day) were actually achieved by the wild-type parental strain.

WO 2011/097261 and US20120322157 report that a gene denoted "SN03" encoding an arrestin protein has a role in increasing lipid production under nutrient replete conditions when overexpressed in *Chlamydomonas*. However, overexpression of the SN03 gene was observed to result in the appearance of unidentified polar lipids, which were not quantified, and did not result in an increase in triglycerides (TAG). Another polypeptide identified as potentially regulating stress-induced lipid biosynthesis has been described by Boyle et al. ((2012) *J. Biol. Chem.* 287:15811-15825). Knockout of the NRR1 gene in *Chlamydomonas* encoding a "SQUAMOUSA" domain polypeptide resulted in a reduction of lipid biosynthesis with respect to wild type cells under nitrogen depletion; however, no mutants were obtained demonstrating increased lipid production. US 2010/0255550 suggests the overexpression of putative transcription factors (TF1, TF2, TF3, TF4, and TF5) in algal cells to increase lipid production, but no such strains are disclosed.

U.S. Patent Application Publication No. US 2017/005803 discloses a gene encoding a regulator that includes a Zinc Cys domain whose attenuation results in increased lipid productivity in mutant algae when cultured in a medium that includes nitrate. The mutant algae demonstrated growth in culture, accumulating biomass at a rate at least 80% that of wild type cells while producing up to twice as much lipid as the wild type progenitor strain. U.S. Patent Application Publication No. US 2017/0121742 discloses mutant algae having attenuated expression of a gene encoding a polypeptide having a Bromo domain and a TAZ zinc finger domain that demonstrate elevated lipid productivity with minimal reduction in biomass productivity with respect to wild type algae.

SUMMARY OF THE DISCLOSURE

In one aspect, provided herein are mutant microorganisms having attenuated expression of a gene encoding a polypeptide that includes a domain known as the cGMP-specific phosphodiesterases, Adenylyl cyclases, and the transcriptional activator FhlA (GAF) domain, such as for example, a GAF2 domain (e.g., SEQ ID NO:1), that in some embodiments, produce more lipid than a control microorganism and/or exhibit increased partitioning of carbon to lipid with respect to the control microorganism, when the mutant microorganism and the control microorganism are cultured under the same conditions. In some embodiments, the control microorganism is a wild-type microorganism. In some embodiments, the mutant microorganism produces at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 100%, at least about 110%, at least about 120%, at least about 130%, at least about 140%, at least about 150%, at least about 160%, at least about 170%, at least about 180%, at least about 190%, at least about 200%, at least about 210%, at least about 220%, at least about 230%, at least about 240%, or at least about 250% more (e.g., at least any of 25%, 50%, 100%, 150%, 200% or 250% more) fatty acid methyl ester-derivatizable lipids (FAME lipids) than a control microorganism. In some embodiments, the mutant microorganisms provided herein exhibit a ratio of FAME to TOC that is at least about 50%, at least about 60%, at least about 70%, at least about 80%, at least about 90%, at least about 100%, at least about 120%, at least about 140%, at least about 160%, at least about 180%, at least about 200%, at least about 220%, at least about 240%, at least about 260%, at least about 280%, at least about 300%, at least about 320%, at least about 340%, at least about 360%, at least about 380%, or at least about 400% higher (e.g., 50-400% higher) than the FAME/TOC ratio of the control microorganism.

"Attenuated expression" of a gene as set forth above includes, for example, reduced expression of the gene such that a reduced level (which may be an undetectable level) of a functional polypeptide encoded by the gene is produced. Attenuated expression also includes expression where a mutated (such as a deleted, truncated, or frame-shifted) polypeptide is produced, such that the mutated polypeptide has reduced or altered function with respect to the non-mutated polypeptide. Attenuated expression can be the result of mutation of the gene encoding the polypeptide, or can be the result of expression or delivery of a construct designed to reduced expression of the gene encoding the polypeptide, such as, for example, and RNAi construct targeting the gene.

In some embodiments, the mutant microorganisms are generated by classical mutagenesis or by genetic engineering techniques. In some embodiments, the mutant microorganism may have a mutation in a gene encoding a polypeptide that includes a GAF (e.g., GAF2) domain, or a gene affecting the expression thereof, that results in a decrease in the level of expression of the gene encoding a polypeptide that includes a GAF domain compared to the level of expression of the gene in a control microorganism. In some embodiments, the one or more mutations are generated using one or more agents that induce a double strand break. In some examples, the agent is a meganuclease, a zinc finger nuclease, a Transcription Activator-Like Effector Nuclease (TALEN) system, and/or a Cas nuclease. In some embodiments, a mutation that results in attenuated expression of a gene encoding a GAF domain is an insertional mutation.

In some embodiments, the mutant microorganism is any eukaryotic microorganism, and in illustrative embodiments, the mutant microorganism is a heterokont or alga. In some example, the mutant microorganism is a heterokont alga such as a diatom or Eustigmatophyte species, and may be, for example, a species of a diatom genus such as *Amphiprora, Amphora, Chaetoceros, Cyclotella, Fragilaria, Fragilaropsis, Hantzschia, Navicula, Nitzschia, Phceodactylum, Phceodactylum, Phceodactylum, Skeletonema,* or *Thalassiosira.* In some examples, the mutant alga is a Eustigmatophyte, such as a Eustigmatophyte belonging to a genus such as *Chloridella, Chlorobptrys, Ellipsoidion, Eustigmatos, Goniochloris, Monodopsis, Monodus, Nannochloropsis, Pseudocharaciopsis, Pseudostaruastrum, Pseudotetraedriella,* and *Vischeria.*

Also provided herein is a biomass comprising a mutant as provided herein. Further provided is an extract of a mutant as provided herein. The extract can be a crude extract or a partially purified, purified, or refined extract that can include any combination of cellular components, including but not limited to membranes, lipids, proteins, carbohydrate, soluble molecules and insoluble molecules. For example the extract can optionally be an extract that has been subjected to one or more treatments such as but not limited to selective precipitation, high or low temperature treatment, filtration, or centrifugation.

Also included are methods of producing lipids using the mutant microorganisms disclosed herein. For example, a mutant microorganism as provided herein can be cultured in batch, semi-continuous, or continuous culture to produce one or more lipids. The methods can include isolating one or more lipids from the culture (e.g., from the cells, culture medium, or whole culture). The culture medium can be nitrogen replete or can be nitrogen-limited or nitrogen deplete. In some embodiments, the medium used for culturing a mutant microorganism as provided herein to produce lipid can include nitrate as substantially the sole source of nitrogen. In some examples, the methods can include culturing an algal mutant under photoautrophic conditions.

Also included are DNA molecules for expressing guide RNAs; guide RNAs that target a gene that encodes a GAF2 domain-containing protein that affects lipid production; and nucleic acid constructs for generating mutant microorganisms using genetic engineering techniques. A guide RNA that targets a GAF gene, e.g., a GAF2 gene, can have homology to a coding region of the gene that includes a GAF domain, or can have homology to a sequence of an intron, 5' UTR, 3' UTR, or region of a gene upstream of the 5'UTR.

These and other objects and features of the invention will become more fully apparent when the following detailed description of the invention is read in conjunction with the accompanying drawings.

BRIEF DESCRIPTION OF THE DRAWINGS

FIG. 4 shows daily FAME productivity over eight days of the assays; FIG. 5 shows daily TOC productivity over eight days of the assays; and FIG. 6 provides the FAME/TOC ratios for each day of the assays. Error bars represent standard deviations of two biological replicates except for day 7. Symbols used in graphs: open diamonds represent wild type WT-3730 cultured in nitrate-only medium PM074, closed diamonds represent wild type WT-3730 cultured in nitrate medium supplemented with ammonium PM124, open triangles represent knockout mutant GE-13536 cultured in nitrate-only medium PM074, and closed triangles represent knockout mutant GE-13536 cultured in nitrate medium supplemented with ammonium PM124.

DETAILED DESCRIPTION

Definitions

Figure 1:
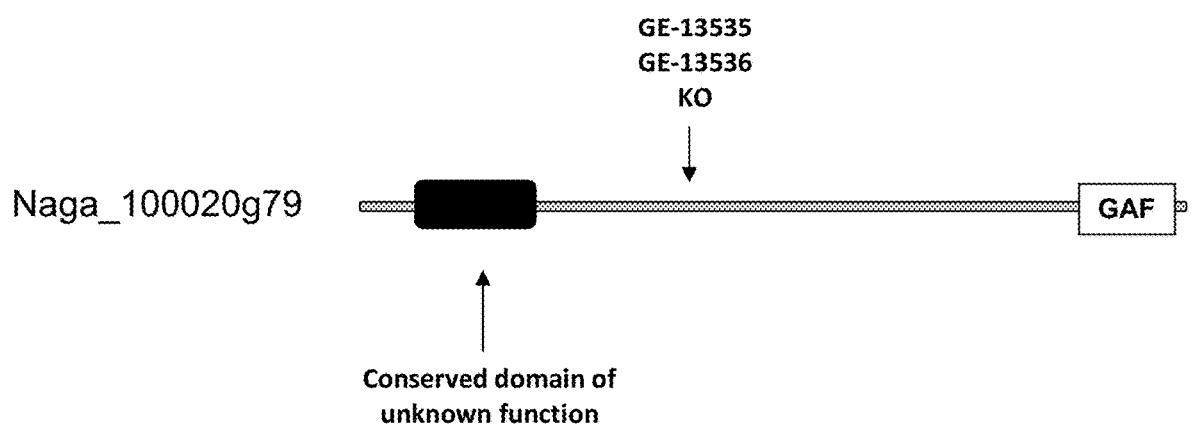
FIG. 1 is a schematic depiction of the protein encoded by a gene at the *N. gaditana* locus Naga_100020g79 (represented by SEQ ID NO:2). The boxes denote a conserved domain of unknown function (at amino acid residues 109-390 of the gene product represented by SEQ ID NO:2) and the GAF2 domain (at amino acid residues 822-1047 of the gene product represented by SEQ ID NO:2). The arrow labeled GE-13535, GE13536 KO demonstrates where the Hygromycin resistance marker was inserted using CRISPR/Cas9 to generate knockout strains GE-13535 and GE-13536. The figure is not to scale.

Unless defined otherwise, all technical and scientific terms used herein have the same meaning as commonly understood by one of ordinary skill in the art to which this invention belongs. In case of conflict, the present application including the definitions will control. Unless otherwise required by context, singular terms shall include pluralities and plural terms shall include the singular.

All headings are for the convenience of the reader and do not limit the invention in any way. References to aspects or embodiments of the invention do not necessarily indicate that the described aspects may not be combined with other described aspects of the invention or features of other aspects of the invention. All publications, patents and other references mentioned herein are incorporated by reference in their entireties for all purposes as if each individual publication or patent application were specifically and individually indicated to be incorporated by reference.

The term "and/or" as used in a phrase such as "A and/or B" herein is intended to include "A and B", "A or B", "A", and "B".

The terms "about", "approximately", and the like, when preceding a list of numerical values or range, refer to each individual value in the list or range independently as if each individual value in the list or range was immediately preceded by that term. The terms mean that the values to which the same refer are exactly, close to, or similar thereto. In some usages "about" or "approximately" can mean within 10%, within 5%, or within 2.5% of the stated value.

"Optional" or "optionally" means that the subsequently described event or circumstance can or cannot occur, and that the description includes instances where the event or circumstance occurs and instances where it does not. For example, the phrase optionally the composition can comprise a combination means that the composition may comprise a combination of different molecules or may not include a combination such that the description includes both the combination and the absence of the combination (i.e., individual members of the combination). Ranges may be expressed herein as from about one particular value, and/or to about another particular value. When such a range is expressed, another aspect includes from the one particular value and/or to the other particular value. Similarly, when values are expressed as approximations, by use of the antecedent about or approximately, it will be understood that the particular value forms another aspect. It will be further understood that the endpoints of each of the ranges are significant both in relation to the other endpoint, and independently of the other endpoint. In addition, a range (e.g., 90-100%) is meant to include the range per se as well as each independent value within the range as if each value was individually listed. All ranges provided within the application are inclusive of the values of the upper and lower ends of the range unless specifically indicated otherwise. The term "combined" or "in combination" or "in conjunction" may refer to a physical combination of agents that are administered together or the use of two or more agents simultaneously with reference to, e.g., time and/or physicality.

Where the intended meaning of "substantially" in a particular context is not set forth, the term is used to include minor and irrelevant deviations that are not material to the characteristics considered important in the context of the subject matter of the invention.

The term "gene" is used broadly to refer to any segment of a nucleic acid molecule (typically DNA, but optionally RNA) encoding a polypeptide or expressed RNA. Thus, genes include sequences encoding expressed RNA (which can include polypeptide coding sequences or, for example, functional RNAs, such as ribosomal RNAs, tRNAs, antisense RNAs, microRNAs, short hairpin RNAs, ribozymes, etc.). Genes may further comprise regulatory sequences required for or affecting their expression, as well as sequences associated with the protein or RNA-encoding sequence in its natural state, such as, for example, intron sequences, 5' or 3' untranslated sequences, etc. In some examples, "gene" may only refer to a protein-encoding portion of a DNA or RNA molecule, which may or may not include introns. A gene is preferably greater than 50 nucleotides in length, more preferably greater than 100 nucleotide in length, and can be, for example, between 50 nucleotides and 500,000 nucleotides in length, such as between 100 nucleotides and 100,000 nucleotides in length or between about 200 nucleotides and about 50,000 nucleotides in length, or about 200 nucleotides and about 20,000 nucleotides in length. Genes can be obtained from a variety of sources, including cloning from a source of interest or synthesizing from known or predicted sequence information.

The term "nucleic acid" or "nucleic acid molecule" refers to, a segment of DNA or RNA (e.g., mRNA), and also includes nucleic acids having modified backbones (e.g., peptide nucleic acids, locked nucleic acids and other modified nucleic acids or nucleic acid analogs (e.g., phosphono peptide nucleci acids, Efimov and Chakhmakhcheva (2005) *Methods Mol Biol.* 288: 147-163)) or modified or non-naturally-occurring nucleobases. The nucleic acid molecules can be double-stranded, partially double stranded, or single-stranded; a single stranded nucleic acid molecule that comprises a gene or a portion thereof can be a coding (sense) strand or a non-coding (antisense) strand. Although a sequence of the nucleic acids may be shown in the form of DNA, a person of ordinary skill in the art recognizes that the corresponding RNA sequence will have a similar sequence with the thymine being replaced by uracil i.e. "t" with "u".

A nucleic acid molecule may be "derived from" an indicated source, which includes the isolation (in whole or in part) of a nucleic acid segment from an indicated source. A nucleic acid molecule may also be derived from an indicated source by, for example, direct cloning, PCR amplification, or artificial synthesis from the indicated polynucleotide source or based on a sequence associated with the indicated polynucleotide source, which may be, for example, a species of organism. Genes or nucleic acid molecules derived from a particular source or species also include genes or nucleic acid molecules having sequence modifications with respect to the source nucleic acid molecules. For example, a gene or nucleic acid molecule derived from a source (e.g., a particular referenced gene) can include one or more mutations with respect to the source gene or nucleic acid molecule that are unintended or that are deliberately introduced, and if one or more mutations, including substitutions, deletions, or insertions, are deliberately introduced the sequence alterations can be introduced by random or targeted mutation of cells or nucleic acids, by amplification or other gene synthesis or molecular biology techniques, or by chemical synthesis, or any combination thereof. A gene or nucleic acid molecule that is derived from a referenced gene or nucleic acid molecule that encodes a functional RNA or polypeptide can encode a functional RNA or polypeptide having at least about 50%, at least about 55%, at least about 65%, at least about 70%, at least about 75%, at least about 80%, at least about 85%, at least about 90%, at least about 95%, at least about 96%, at least about 97%, at least about 98%, or at least about 99% sequence identity with the referenced or source functional RNA or polypeptide, or to a functional fragment thereof. For example, a gene or nucleic acid molecule that is derived from a referenced gene or nucleic acid molecule that encodes a functional RNA or polypeptide can encode a functional RNA or polypeptide having at least about 85%, at least about 90%, at least about 95%, at least about 96%, at least about 97%, at least about 98%, or at least about 99% sequence identity with the referenced or source functional RNA or polypeptide, or to a functional fragment thereof.

As used herein, an "isolated" nucleic acid or protein is removed from its natural milieu or the context in which the nucleic acid or protein exists in nature. For example, an isolated protein or nucleic acid molecule is removed from the cell or organism with which it is associated in its native or natural environment. An isolated nucleic acid or protein can be, in some instances, partially or substantially purified, but no particular level of purification is required for isolation. Thus, for example, an isolated nucleic acid molecule can be a nucleic acid sequence that has been excised from the chromosome, genome, or episome that it is integrated into in nature.

A "purified" nucleic acid molecule or nucleotide sequence, or protein or polypeptide sequence, is substantially free of cellular material and cellular components. The purified nucleic acid molecule or protein may be substantially free of chemicals beyond buffer or solvent, for example. "Substantially free" is not intended to mean that other components beyond the novel nucleic acid molecules are undetectable.

The terms "naturally-occurring" and "wild type" refer to a form found in nature which is most frequently observed in a naturally occurring population and is thus arbitrarily designated as "wild-type". For example, a naturally occurring or wild type nucleic acid molecule, nucleotide sequence or protein may be present in and isolated from a natural source, and is not intentionally modified by human manipulation. "Wild-type" may also refer to the sequence at a specific nucleotide position or positions, or the sequence at a particular codon position or positions, or the sequence at a particular amino acid position or positions.

As used herein "attenuated" means reduced in amount, degree, intensity, or strength. Attenuated gene expression may refer to a significantly reduced amount and/or rate of transcription of the gene in question, or of translation, folding, or assembly of the encoded protein. As nonlimiting examples, an attenuated gene may be a mutated or disrupted gene (e.g., a gene disrupted by partial or total deletion, truncation, frameshifting, or insertional mutation) that does not encode a complete functional open reading frame or that has decreased expression due to alteration or disruption of gene regulatory sequences. An attenuated gene may also be a gene targeted by a construct that reduces expression of the gene, such as, for example, an antisense RNA, microRNA, RNAi molecule, or ribozyme. Attenuated gene expression can be gene expression that is eliminated, for example, reduced to an amount that is insignificant or undetectable. Attenuated gene expression can also be gene expression that results in an RNA or protein that is not fully functional or nonfunctional, for example, attenuated gene expression can be gene expression that results in a truncated RNA and/or polypeptide.

"Exogenous nucleic acid molecule" or "exogenous gene" refers to a nucleic acid molecule or gene that has been introduced ("transformed") into a cell. A transformed cell may be referred to as a recombinant cell, into which additional exogenous gene(s) may be introduced. A descendent of a cell transformed with a nucleic acid molecule is also referred to as "transformed" if it has inherited the exogenous nucleic acid molecule. The exogenous gene or nucleic acid molecule may be derived from a different species (and so "heterologous"), or from the same species (and so "homologous"), relative to the cell being transformed. An "endogenous" nucleic acid molecule, gene or protein is a native nucleic acid molecule, gene, or protein as it occurs in, or is naturally produced by, the host.

The term "native" is used herein to refer to nucleic acid sequences or amino acid sequences as they naturally occur in the host. The term "non-native" is used herein to refer to nucleic acid sequences or amino acid sequences that do not occur naturally in the host. Thus, a "non-native" nucleic acid molecule is a nucleic molecule that is not naturally present in the host cell, for example, the non-native nucleic acid molecule is exogenous to the host cell or microorganism into which it is introduced, and may be heterologous with respect to the host cell or microorganism. Additionally, a nucleic acid sequence or amino acid sequence that has been removed from a cell, subjected to laboratory manipulation, and introduced or reintroduced into a host cell such that it differs in sequence or location in the genome with respect to its position in a non-manipulated organism (i.e., is juxtaposed with or operably linked to sequences it is not juxtaposed with or operably linked to in a non-transformed organism) is considered "non-native". Non-native genes also include genes endogenous to the host microorganism operably linked to one or more heterologous regulatory sequences that have been recombined into the host genome.

A "recombinant" or "engineered" nucleic acid molecule is a nucleic acid molecule that has been altered through human manipulation. As non-limiting examples, a recombinant nucleic acid molecule includes any nucleic acid molecule that: 1) has been partially or fully synthesized or modified in vitro, for example, using chemical or enzymatic techniques (e.g., by use of chemical nucleic acid synthesis, or by use of enzymes for the replication, polymerization, digestion (exonucleolytic or endonucleolytic), ligation, reverse transcription, transcription, base modification (including, e.g., methylation), integration or recombination (including homologous and site-specific recombination) of nucleic acid molecules); 2) includes conjoined nucleotide sequences that are not conjoined in nature; 3) has been engineered using molecular cloning techniques such that it lacks one or more nucleotides with respect to the naturally occurring nucleic acid molecule sequence; and/or 4) has been manipulated using molecular cloning techniques such that it has one or more sequence changes or rearrangements with respect to the naturally occurring nucleic acid sequence. As non-limiting examples, a cDNA is a recombinant DNA molecule, as is any nucleic acid molecule that has been generated by in vitro polymerase reaction(s), or to which linkers have been attached, or that has been integrated into a vector, such as a cloning vector or expression vector.

The term "recombinant protein" as used herein refers to a protein produced by genetic engineering regardless of whether the amino acid varies from that of a wild-type protein.

When applied to organisms, the term recombinant, engineered, or genetically engineered refers to organisms that have been manipulated by introduction of a heterologous or exogenous recombinant nucleic acid sequence into the organism (e.g., a non-native nucleic acid sequence), and includes gene knockouts, targeted mutations, gene replacement, and promoter replacement, deletion, disruption, or insertion, as well as introduction of transgenes or synthetic genes or nucleic acid sequences into the organism. That is, recombinant, engineered, or genetically engineered refers to organisms that have been altered by human intervention. Recombinant or genetically engineered organisms can also be organisms into which constructs for gene "knockdown" have been introduced. Such constructs include, but are not limited to, RNAi, microRNA, shRNA, siRNA, antisense, and ribozyme constructs. Also included are organisms whose genomes have been altered by the activity of meganucleases, zinc finger nucleases, TALENs, or Cas/CRISPR systems. An exogenous or recombinant nucleic acid molecule can be integrated into the recombinant/genetically engineered organism's genome or in other instances may not be integrated into the host genome. As used herein, "recombinant microorganism" or "recombinant host cell" includes progeny or derivatives of the recombinant microorganisms of the invention. Because certain modifications may occur in succeeding generations due to either mutation or environmental influences, such progeny or derivatives may not, in fact, be identical to the parent cell, but are still included within the scope of the term as used herein.

The term "promoter" refers to a nucleic acid sequence capable of binding RNA polymerase in a cell and initiating transcription of a downstream (3' direction) coding sequence. A promoter includes a minimum number of bases or elements necessary to initiate transcription at levels detectable above background. A promoter can include a transcription initiation site as well as protein binding domains (consensus sequences) responsible for the binding of RNA polymerase. Eukaryotic promoters often, but not always, contain "TATA" boxes and "CAT" boxes. Prokaryotic promoters may contain −10 and −35 prokaryotic promoter consensus sequences. A large number of promoters, including constitutive, inducible and repressible promoters, from a variety of different sources are well known in the art. Representative sources include for example, algal, viral, mammalian, insect, plant, yeast, and bacterial cell types, and suitable promoters from these sources are readily available, or can be made synthetically, based on sequences publicly available on line or, for example, from depositories such as the ATCC as well as other commercial or individual sources. Promoters can be unidirectional (initiate transcription in one direction) or bi-directional (initiate transcription in either direction). A promoter may be a constitutive promoter, a repressible promoter, or an inducible promoter. A promoter region can include, in addition to the gene-proximal promoter where RNA polymerase binds to initiate transcription, additional sequences upstream of the gene that can be within about 1 kb, about 2 kb, about 3 kb, about 4 kb, about 5 kb or more of the transcriptional start site of a gene, where the additional sequences can influence the rate of transcription of the downstream gene and optionally the responsiveness of the promoter to developmental, environmental, or biochemical (e.g., metabolic) conditions.

The term "heterologous" when used in reference to a polynucleotide, gene, nucleic acid, polypeptide, or enzyme refers to a polynucleotide, gene, nucleic acid, polypeptide, or enzyme that is from a source or derived from a source other than the host organism species. In contrast a "homologous" polynucleotide, gene, nucleic acid, polypeptide, or enzyme is used herein to denote a polynucleotide, gene, nucleic acid, polypeptide, or enzyme that is derived from the host organism species. When referring to a gene regulatory sequence or to an auxiliary nucleic acid sequence used for maintaining or manipulating a gene sequence (e.g., a promoter, a 5' untranslated region, 3' untranslated region, poly A addition sequence, intron sequence, splice site, ribosome binding site, internal ribosome entry sequence, genome homology region, recombination site, etc.), "heterologous" means that the regulatory sequence or auxiliary sequence is not naturally associated with the gene with which the regulatory or auxiliary nucleic acid sequence is juxtaposed in a construct, genome, chromosome, or episome. Thus, a promoter operably linked to a gene to which it is not operably linked to in its natural state (i.e. in the genome of a non-genetically engineered organism) is referred to herein as a "heterologous promoter," even though the promoter may be derived from the same species (or, in some cases, the same organism) as the gene to which it is linked.

As used herein, the term "protein" or "polypeptide" is intended to encompass a singular "polypeptide" as well as plural "polypeptides," and refers to a molecule composed of monomers (amino acids) linearly linked by amide bonds (also known as peptide bonds). The term "polypeptide" refers to any chain or chains of two or more amino acids, and does not refer to a specific length of the product. Thus, peptides, dipeptides, tripeptides, oligopeptides, "protein," "amino acid chain," or any other term used to refer to a chain or chains of two or more amino acids, are included within the definition of "polypeptide," and the term "polypeptide" can be used instead of, or interchangeably with any of these terms.

Gene and protein Accession numbers, commonly provided in parenthesis after a gene or species name, are unique identifiers for a sequence record publicly available at the National Center for Biotechnology Information (NCBI) website (ncbi.nlm.nih.gov) maintained by the United States National Institutes of Health. The "GenInfo Identifier" (GI) sequence identification number is specific to a nucleotide or amino acid sequence. If a sequence changes in any way, a new GI number is assigned. A Sequence Revision History tool is available to track the various GI numbers, version numbers, and update dates for sequences that appear in a specific GenBank record. Searching and obtaining nucleic acid or gene sequences or protein sequences based on Accession numbers and GI numbers is well known in the arts of, e.g., cell biology, biochemistry, molecular biology, and molecular genetics. Gene loci identifiers refer to the published genome described in Corteggiani Carpinelli et al. (2014) *Mol Plant* 7:323-335 and available online on the CRIBI Genomics *Nannochloropsis* genome portal (nannochloropsis.org).

As used herein, the terms "percent identity" or "homology" with respect to nucleic acid or polypeptide sequences are defined as the percentage of nucleotide or amino acid residues in the candidate sequence that are identical with the known polypeptides, after aligning the sequences for maximum percent identity and introducing gaps, if necessary, to achieve the maximum percent homology. For polypeptide sequences, N-terminal or C-terminal insertions or deletions shall not be construed as affecting homology, and internal deletions and/or insertions into the polypeptide sequence of less than about 65, less than about 60, less than about 50, less than about 40, less than about 30, less than about 20, or less than about 10 amino acid residues shall not be construed as affecting homology of compared amino acid (protein) sequences. For nucleic acid sequences, 5' end or 3' end insertions or deletions shall not be construed as affecting homology, and internal deletions and/or insertions into the polypeptide sequence of less than about 200, less than about 180, less than about 150, less than about 120, less than about 100, less than about 90, less than about 80, less than about 70, less than about 60, less than about 50, less than about 40, or less than about 30 nucleotides shall not be construed as affecting homology of compared nucleic acid sequences. Homology or identity at the nucleotide or amino acid sequence level can be determined by BLAST (Basic Local Alignment Search Tool) analysis using the algorithm employed by the programs blastp, blastn, blastx, tblastn, and tblastx (Altschul (1997), *Nucleic Acids Res.* 25, 3389-3402, and Karlin (1990), *Proc. Natl. Acad. Sci. USA* 87, 2264-2268), which are tailored for sequence similarity searching. The approach used by the BLAST program is to first consider similar segments, with and without gaps, between a query sequence and a database sequence, then to evaluate the statistical significance of all matches that are identified, and finally to summarize only those matches which satisfy a preselected threshold of significance. For a discussion of basic issues in similarity searching of sequence databases, see Altschul (1994), *Nature Genetics* 6, 119-129. The search parameters for histogram, descriptions, alignments, expect (i.e., the statistical significance threshold for reporting matches against database sequences), cutoff, matrix, and filter (low complexity) can be at the default settings. The default scoring matrix used by blastp, blastx, tblastn, and tblastx is the BLOSUM62 matrix (Henikoff (1992), *Proc. Natl. Acad. Sci. USA* 89, 10915-10919), recommended for query sequences over 85 in length (nucleotide bases or amino acids).

For blastn, designed for comparing nucleotide sequences, the scoring matrix is set by the ratios of M (i.e., the reward score for a pair of matching residues) to N (i.e., the penalty score for mismatching residues), wherein the default values for M and N can be +5 and −4, respectively. Four blastn parameters can be adjusted as follows: Q=10 (gap creation penalty); R=10 (gap extension penalty); wink=1 (generates word hits at every winkth position along the query); and gapw=16 (sets the window width within which gapped alignments are generated). The equivalent Blastp parameter settings for comparison of amino acid sequences can be: Q=9; R=2; wink=1; and gapw=32. A Bestfit comparison between sequences, available in the GCG package version 10.0, can use DNA parameters GAP=50 (gap creation penalty) and LEN=3 (gap extension penalty), and the equivalent settings in protein comparisons can be GAP=8 and LEN=2.

Thus, when referring to the polypeptide or nucleic acid sequences of the present invention, included are sequence identities of at least about 50%, of at least about 55%, of at least about 60%, at least about 65%, at least about 70%, at least about 75%, at least about 80%, at least about 85%, at least about 90%, at least about 95%, at least about 96%, at least about 97%, at least about 98%, at least about 99%, or about 100% (e.g., at least any of 50%, 75% or 90%) sequence identity with the full-length polypeptide or nucleic acid sequence, or to fragments thereof comprising a consecutive sequence of at least about 100, at least about 125, at least about 150 (e.g., at least 100) or more amino acid residues of the entire protein; variants of such sequences, e.g., wherein at least one amino acid residue has been inserted N- and/or C-terminal to, and/or within, the disclosed sequence(s) which contain(s) the insertion and substitution. Contemplated variants can additionally or alternately include those containing predetermined mutations by, e.g., homologous recombination or site-directed or PCR mutagenesis, and the corresponding polypeptides or nucleic acids of other species, including, but not limited to, those described herein, the alleles or other naturally occurring variants of the family of polypeptides or nucleic acids which contain an insertion and substitution; and/or derivatives wherein the polypeptide has been covalently modified by substitution, chemical, enzymatic, or other appropriate means with a moiety other than a naturally occurring amino acid which contains the insertion and substitution (for example, a detectable moiety such as an enzyme).

As used herein, the phrase "conservative amino acid substitution" or "conservative mutation" refers to the replacement of one amino acid by another amino acid with a common property. A functional way to define common properties between individual amino acids is to analyze the normalized frequencies of amino acid changes between corresponding proteins of homologous organisms (Schulz (1979) Principles of Protein Structure, Springer-Verlag). According to such analyses, groups of amino acids can be defined where amino acids within a group exchange preferentially with each other, and therefore resemble each other most in their impact on the overall protein structure (Schulz (1979) Principles of Protein Structure, Springer-Verlag). Examples of amino acid groups defined in this manner can include: a "charged/polar group" including Glu, Asp, Asn, Gln, Lys, Arg, and His; an "aromatic or cyclic group" including Pro, Phe, Tyr, and Trp; and an "aliphatic group" including Gly, Ala, Val, Leu, Ile, Met, Ser, Thr, and Cys. Within each group, subgroups can also be identified. For example, the group of charged/polar amino acids can be sub-divided into sub-groups including: the "positively-charged sub-group" comprising Lys, Arg and His; the "negatively-charged sub-group" comprising Glu and Asp; and the "polar sub-group" comprising Asn and Gln. In another example, the aromatic or cyclic group can be sub-divided into sub-groups including: the "nitrogen ring sub-group" comprising Pro, His, and Trp; and the "phenyl sub-group" comprising Phe and Tyr. In another further example, the aliphatic group can be sub-divided into sub-groups including: the "large aliphatic non-polar sub-group" comprising Val, Leu, and Ile; the "aliphatic slightly-polar sub-group" comprising Met, Ser, Thr, and Cys; and the "small-residue sub-group" comprising Gly and Ala. Examples of conservative mutations include amino acid substitutions of amino acids within the sub-groups above, such as, but not limited to: Lys for Arg or vice versa, such that a positive charge can be maintained; Glu for Asp or vice versa, such that a negative charge can be maintained; Ser for Thr or vice versa, such that a free —OH can be maintained; and Gln for Asn or vice versa, such that a free —NH2 can be maintained. A "conservative variant" is a polypeptide that includes one or more amino acids that have been substituted to replace one or more amino acids of the reference polypeptide (for example, a polypeptide whose sequence is disclosed in a publication or sequence database, or whose sequence has been determined by nucleic acid sequencing) with an amino acid having common properties, e.g., belonging to the same amino acid group or sub-group as delineated above.

As used herein, "expression" includes the expression of a gene at least at the level of RNA production, and an "expression product" includes the resultant product, e.g., a polypeptide or functional RNA (e.g., a ribosomal RNA, a tRNA, an antisense RNA, a micro RNA, an shRNA, a ribozyme, etc.), of an expressed gene. The term "increased expression" includes an alteration in gene expression to facilitate increased mRNA production and/or increased polypeptide expression. "Increased production" [of a gene product] includes an increase in the amount of polypeptide expression, in the level of the enzymatic activity of a polypeptide, or a combination of both, as compared to the native production or enzymatic activity of the polypeptide.

Some aspects of the present invention include the partial, substantial, or complete deletion, silencing, inactivation, or down-regulation of expression of particular polynucleotide sequences. The genes may be partially, substantially, or completely deleted, silenced, inactivated, or their expression may be down-regulated in order to affect the activity performed by the polypeptide they encode, such as the activity of an enzyme. Genes can be partially, substantially, or completely deleted, silenced, inactivated, or down-regulated by insertion of nucleic acid sequences that disrupt the function and/or expression of the gene (e.g., viral insertion, transposon mutagenesis, meganuclease engineering, homologous recombination, CRISPR/cas systems, or other methods known in the art). The terms "eliminate," "elimination," and "knockout" can be used interchangeably with the terms "deletion," "partial deletion," "substantial deletion," or "complete deletion." In certain embodiments, a microorganism of interest may be engineered by site directed homologous recombination or targeted integration or mutation using a cas/CRISPR system to knockout a particular gene of interest. In still other embodiments, targeted insertion into or mutation of a gene using a cas/CRISPR system, RNAi, or antisense DNA (asDNA) constructs may be used to partially, substantially, or completely silence, inactivate, or down-regulate a particular gene of interest.

These insertions, disruptions, deletions, base modifications, or other modifications of certain nucleic acid molecules or particular polynucleotide sequences may be understood to encompass "genetic modification(s)" or "transformation(s)" such that the resulting strains of the microorganisms or host cells may be understood to be "genetically modified", "genetically engineered" or "transformed."

As used herein, "up-regulated" or "up-regulation" includes an increase in expression of a gene or nucleic acid molecule of interest or the activity of an enzyme, e.g., an increase in gene expression or enzymatic activity as compared to the expression or activity in an otherwise identical gene or enzyme that has not been up-regulated.

As used herein, "down-regulated" or "down-regulation" includes a decrease in expression of a gene or nucleic acid molecule of interest or the activity of an enzyme, e.g., a decrease in gene expression or enzymatic activity as compared to the expression or activity in an otherwise identical gene or enzyme that has not been down-regulated.

As used herein, "mutant" refers to an organism that has a mutation in a gene that is the result of classical mutagenesis, for example, using gamma irradiation, UV, or chemical mutagens. "Mutant" as used herein also refers to a recombinant cell that has altered structure or expression of a gene as a result of genetic engineering that many include, as non-limiting examples, overexpression, including expression of a gene under different temporal, biological, or environmental regulation and/or to a different degree than occurs naturally and/or expression of a gene that is not naturally expressed in the recombinant cell; homologous recombination, including knock-outs and knock-ins (for example, gene replacement with genes encoding polypeptides having greater or lesser activity than the wild type polypeptide, and/or dominant negative polypeptides); gene attenuation via RNAi, antisense RNA, or ribozymes, or the like; and genome engineering using meganucleases, zinc finger nucleases, TALENs, and/or CRISPR technologies, and the like. A mutant as described herein is made by human intervention and is therefore not a naturally-occurring organism. A mutant organism of interest will typically have a phenotype different than that of the corresponding wild type or progenitor strain that lacks the mutation, where the phenotype can be assessed by growth assays, product analysis, photosynthetic properties, biochemical assays, etc. When referring to a gene "mutant" means the gene has at least one base (nucleotide) change, deletion, or insertion with respect to a native or wild type gene. The mutation (change, deletion, and/or insertion of one or more nucleotides) can be in the coding region of the gene or can be in an intron, 3' UTR, 5' UTR, or promoter region, e.g., within about 1 kb, about 2 kb, or about 3 kb, about 4 kb, or about 5 kb of the translational start site. For example, a mutant having attenuated expression of a gene as disclosed herein can have a mutation, which can be one or more nucleobase changes and/or one or more nucleobase deletions and/or one or more nucleobase insertions, into the region of a gene 5' of the transcriptional start site, such as, in non-limiting examples, within 2 kb, within 1.5 kb, within 1 kb, or within 0.5 kb of the known or putative transcriptional start site, or within 3 kb, within 2.5 kb, within 2 kb, within 1.5 kb, within 1 kb, or within 0.5 kb of the translational start site. As nonlimiting examples, a mutant gene can be a gene that has a mutation, insertion, and/or deletion within the promoter region that can either increase or decrease expression of the gene; can be a gene that has a deletion that results in production of a nonfunctional protein, truncated protein, dominant negative protein, and/or no protein; and/or can be a gene that has one or more point mutations leading to a change in the amino acid of the encoded protein or results in aberrant splicing of the gene transcript, etc.

Conserved domains of polypeptides include those identified in the "cd" (conserved domain) database, the COG database, the pfam database, the SMART database, the PRK database, the TIGRFAM database, or others known the art. The National Center for Biotechnology Information website sponsored by the U.S. National Institutes of Health includes a conserved domain database (CDD) which it describes as "a protein annotation resource that consists of a collection of well-annotated multiple sequence alignment models for ancient domains and full-length proteins. These are available as position-specific score matrices (PSSMs) for fast identification of conserved domains in protein sequences via RPS-BLAST. CDD content includes NCBI-curated domains, which use 3D-structure information to explicitly define domain boundaries and provide insights into sequence/structure/function relationships, as well as domain models imported from a number of external source databases (Pfam, SMART, COG, PRK, TIGRFAM)." Sequences can be searched for conserved domains, for example, at the cdd database of NCBI. See, Marchler-Bauer et al. (2015) *Nucleic Acids Res*. 43(D) 222-226.

The term "Pfam" refers to a large collection of protein domains and protein families maintained by the Pfam Consortium and available at several sponsored world wide web sites. The latest release of Pfam is Pfam 30.0 (June 2016) based on the UniProt protein database release 2012_06. Pfam domains and families are identified using multiple sequence alignments and hidden Markov models (HMMs). Pfam-A family or domain assignments, are high quality assignments generated by a curated seed alignment using representative members of a protein family and profile hidden Markov models based on the seed alignment. (Unless otherwise specified, matches of a queried protein to a Pfam domain or family are Pfam-A matches.) All identified sequences belonging to the family are then used to automatically generate a full alignment for the family (Sonnhammer (1998) *Nucleic Acids Research* 26, 320-322; Bateman (2000) Nucleic Acids Research 26, 263-266; Bateman (2004) *Nucleic Acids Research* 32, Database Issue, D138-D141; Finn (2006) *Nucleic Acids Research Database* Issue 34, D247-251; Finn (2010) *Nucleic Acids Research* Database Issue 38, D211-222). By accessing the Pfam database, for example, using any of the relevant websites (e.g., pfam.xfam.org), protein sequences can be queried against the HMMs using HMMER homology search software (e.g., HMMER2, HMMER3, or a higher version, available online). Significant matches that identify a queried protein as being in a pfam family (or as having a particular Pfam domain) are those in which the bit score is greater than or equal to the gathering threshold for the Pfam domain. Expectation values (e values) can also be used as a criterion for inclusion of a queried protein in a Pfam or for determining whether a queried protein has a particular Pfam domain, where low e values (much less than 1.0, for example less than 0.1, or less than or equal to 0.01) represent low probabilities that a match is due to chance.

A "cDNA" is a DNA molecule that comprises at least a portion the nucleotide sequence of an mRNA molecule, with the exception that the DNA molecule substitutes the nucleobase thymine, or T, in place of uridine, or U, occurring in the mRNA sequence. A cDNA can be double stranded, partially double stranded, or single stranded and can be, for example, the complement of the mRNA sequence. In preferred examples, a cDNA does not include one or more intron sequences that occur in the naturally-occurring gene that the cDNA corresponds to (i.e., the gene as it occurs in the genome of an organism). For example, a cDNA can have sequences from upstream of an intron of a naturally-occurring gene juxtaposed to sequences downstream of the intron of the naturally-occurring gene, where the upstream and downstream sequences are not juxtaposed in a DNA molecule in nature (i.e., the sequences are not juxtaposed in the naturally occurring gene). A cDNA can be produced by reverse transcription of mRNA molecules, or can be synthesized, for example, by chemical synthesis and/or by using one or more restriction enzymes, one or more ligases, one or more polymerases (including, but not limited to, high temperature tolerant polymerases that can be used in polymerase chain reactions (PCRs)), one or more recombinases, etc., based on knowledge of the cDNA sequence, where the knowledge of the cDNA sequence can optionally be based on the identification of coding regions from genome sequences or compiled from the sequences multiple partial cDNAs.

A "control cell" or "control microorganism" is either a wild type cell or microorganism from which the mutant microorganism (genetically engineered or mutagenized microorganism) is directly or indirectly derived, or is a cell or microorganism that is substantially identical to the mutant cell or microorganism referred to (i.e., of the same genus and species, preferably of the same strain) with the exception that the control cell or microorganism does not have the mutation resulting in increased lipid production that the subject microorganism has. For example, where the mutant microorganism has attenuated expression of (1) a gene encoding a polypeptide that includes a GAF (e.g., GAF2) domain; (2) a gene encoding a polypeptide that has a GAF (e.g., GAF2) domain having at least about 50%, at least about 55%, at least about 60%, at least about 65%, at least about 70%, at least about 75%, at least about 80%, at least about 85%, at least about 90%, or at least about 95% identity to SEQ ID NO:1; or (3) a gene encoding a polypeptide having at least about 50%, at least about 55%, at least about 60%, at least about 65%, at least about 70%, at least about 75%, at least about 80%, at least about 85%, at least about 90%, or at least about 95% identity to SEQ ID NO:2, a control cell can be substantially identical to the mutant microorganism with the exception that the control microorganism does not have attenuated expression of a gene according to 1), 2), or 3).

"The same conditions" or "the same culture conditions", as used herein, means substantially the same conditions, that is, any differences between the referenced conditions that may be present are minor and not relevant to the function or properties of the microorganism that are material to the invention, including lipid production or biomass production.

As used herein "lipid" or "lipids" refers to fats, waxes, fatty acids, fatty acid derivatives such as fatty alcohols, wax esters, alkanes, and alkenes, sterols, monoglycerides, diglycerides, triglycerides, phospholipids, sphingolipids, saccharolipids, and glycerolipids. "FAME lipids" or "FAME" refers to lipids having acyl moieties that can be derivatized to fatty acid methyl esters, such as, for example, monoacylglycerides, diacylglycerides, triacylglycerides (TAGs), wax esters, and membrane lipids such as phospholipids, galactolipids, etc. In one example, lipid productivity can be assessed as FAME productivity in milligrams per liter (mg/L) and for algae, may be reported as grams per meter$^2$ per day (g/m$^2$/day). In one example, the semi-continuous assays provided herein, mg/L values can be converted to g/m2/day by taking into account the area of incident irradiance (for example, the semicontinious process assay (SCPA) flask rack aperture may be 1½×33/8", or 0.003145 m$^2$) and the volume of the culture may be 550 ml. To obtain productivity values in g/m$^2$/day, mg/L values can be multiplied by the daily dilution rate (30%) and a conversion factor of 0.175. Where lipid or subcategories thereof (for example, TAG or FAME) are referred to as a percentage, the percentage is a weight percent unless indicated otherwise.

"Biomass" refers to cellular mass, whether of living or dead cells, and can be assessed, for example, as aspirated pellet weight, but is more preferably dry weight (e.g., lyophilate of a culture sample or pelleted cells), ash-free dry weight (AFDW), or total organic carbon (TOC), using methods known in the art. Biomass increases during the growth of a culture under growth permissive conditions and may be referred to as "biomass accumulation" in batch cultures, for example. In continuous or semi-continuous cultures that undergo steady or regular dilution, biomass that is produced that would otherwise accumulate in the culture is removed during culture dilution. Thus, daily biomass productivity (increases in biomass) by these cultures can also be referred to as "biomass accumulation". Biomass productivity can be assessed as TOC productivity in milligrams per liter (mg/L) and for algae, may be reported as grams per meter$^2$ per day (g/m$^2$/day). In the semi-continuous assays provided herein, mg/L values are converted to g/m2/day by taking into account the area of incident irradiance (the SCPA flask rack aperture of 1½×33/8", or 0.003145 m$^2$) and the volume of the culture (550 ml). To obtain productivity values in g/m$^2$/day, mg/L values are multiplied by the daily dilution rate (30%) and a conversion factor of 0.175. Where biomass is expressed as a percentage, the percentage is a weight percent unless indicated otherwise.

In the context of this disclosure, a "nitrogen source" is a source of nitrogen that can be taken up and metabolized by the subject microorganism and incorporated into biomolecules for growth and propagation. For example, compounds including nitrogen that cannot be taken up and/or metabolized by the microorganism for growth (e.g., nitrogen-containing biological buffers such as Hepes, Tris, etc.) are not considered nitrogen sources in the context of the invention.

"Reduced nitrogen", as used herein, is nitrogen in the chemical form of ammonium salt, ammonia, urea, amides, or an amino acid (e.g., an amino acid that can be taken up and metabolized by the microorganism being cultured to provide a source of nitrogen for incorporation into biomolecules, thereby supporting growth). Examples of amino acids that may be nitrogen sources can include, without limitation, glutamate, glutamine, histidine, proline, lysine, arginine, asparagine, alanine, and glycine. "Non-reduced nitrogen" in the context of a nitrogen source that can be present in a culture medium for microorganisms refers to nitrate or nitrite that must be reduced prior to assimilation into organic compounds by the microorganism.

"The sole source of nitrogen (in the culture medium)" is used interchangeably with "substantially the sole source of nitrogen" and indicates that no other nitrogen source that can be metabolized by the organism (i.e., a nitrogen source that provides nitrogen that can be taken up by the organism and incorporated by the organism into biomolecules such as proteins and nucleic acids) is intentionally added to the culture medium, or that no other nitrogen source that can be utilized by the organism is present in an amount sufficient to significantly increase the growth of the organisms or cells cultured in the referenced medium. Throughout this application, for brevity, the terms "nitrate-only" is used to characterize culture media in which nitrate is the only source of nitrogen that is available to the organisms for supporting growth.

Similarly, "the sole source of carbon (in the culture medium)" is used interchangeably with "substantially the sole source of carbon" and indicates that no other carbon source that can be metabolized by the microorganism (i.e., used for energy or as a carbon source for the production of biomolecules) is present in an amount sufficient to significantly increase the productivity, growth, or propagation of the microorganisms or cells cultured in the referenced medium or that can become incorporated into biomolecules such as lipids produced by the microorganisms or cells at a percentage of greater than 5% of the carbon incorporated into the biomolecule.

"Nitrogen replete" conditions refer to media conditions in which no further growth or propagation benefit is conferred by adding additional nitrogen (in a form that can be used by the microorganism) to the medium. Similarly, "nutrient replete" conditions refer to media conditions in which no nutrient is limiting to growth or propagation, that is, when a medium is nutrient replete, adding additional nutrient(s) to the medium does not result in an improved growth or propagation rate. In the context of "nutrient replete", "nutrients" includes, as nonlimiting examples, phosphate, sulfur, iron, and optionally silica, but excludes carbon sources such as sugars or organic acids that may be used by the organism as an energy source.

Disclosed herein are methods for manipulating, assaying, culturing, and analyzing microorganisms. The invention set forth herein also makes use of standard methods, techniques, and reagents for cell culture, transformation of microorganisms, genetic engineering, and biochemical analysis that are known in the art. Although methods and materials similar or equivalent to those described herein can be used in practice or testing of the present invention, suitable methods and materials are described below. The materials, methods, and examples are illustrative only and are not intended to be limiting. Other features and advantages of the invention will be apparent from the detailed description and from the claims.

Mutant Microorganisms Having Increased Lipid Productivity cGMP-specific phosphodiesterases, Adenylyl cyclases, and the transcriptional activator FhlA ("GAF") domains are found in a wide range of proteins from many microorganisms and are named after some of the proteins in which at least one these domains is present. In some embodiments, this disclosure provides mutant microorganisms having attenuated and/or altered expression and/or function of at least one gene encoding a polypeptide having a GAF domain (including but not limited to inactivation and/or deletion of such a gene), and/or attenuated and/or altered expression and/or function of the polypeptide having a GAF domain per se. Also included are mutant microorganisms having altered expression or function of a gene or protein affecting the expression and/or function of a gene encoding a polypeptide having a GAF domain that affects lipid production. In various embodiments, such mutant microorganisms can produce more lipid and/or exhibit increased partitioning of carbon to lipid as compared to a control microorganism that does not have such attenuated and/or altered expression or function of a gene encoding a polypeptide and/or the polypeptide having a GAF domain. GAF2 domains are a subset of the GAF domain family, typically characterized as belonging to pfam PF13185. In some embodiments, the GAF domain of the mutant microorganism referred to above is a GAF2 domain. In some embodiments, the gene encoding the GAF2 domain is localized to the Naga_100020g79 locus on chromosome 14 of *Nannochloropsis* gaditana, or a syntenic locus in another species. In some embodiments, the gene encoding a polypeptide that includes a GAF2 domain includes a GAF2 domain having an amino acid sequence having at least about 50%, at least 55%, at least 60%, at least 65%, at least 70%, at least 75%, at least 80%, at least 85%, at least 90%, at least 95%, at least 96%, at least 97%, at least 98%, or at least about 99% identity to SEQ ID NO:1. In other embodiments, the mutant microorganism has attenuated expression of a gene encoding a polypeptide that has a GAF (e.g., a GAF2) domain that includes the amino acid sequence set forth in SEQ ID NO:1, or a conservative variant thereof. In other embodiments, the mutant microorganism has attenuated expression of a gene encoding a polypeptide that has a GAF domain (e.g., a GAF2 domain) having the amino acid sequence set forth in SEQ ID NO:1. The gene encoding a GAF2 domain can encode a polypeptide that includes a GAF2 domain and has at least about 50%, at least 55%, at least 60%, at least 65%, at least 70%, at least 75%, at least 80%, at least 85%, at least 90%, at least 95%, at least 96%, at least 97%, at least 98%, or at least about 99% identity to SEQ ID NO:2.

Thus, in some embodiments, the mutant microorganism has attenuated and/or altered expression and/or function of a gene encoding a polypeptide having a GAF2 domain. In some embodiments, the GAF2 domain can be characterized as pfam PF13185 with a bit score of greater than 20.0 or greater than 28.0 (the gathering cutoff) and an e-value of less than 0.01 or less than 0.001.

In some embodiments, a mutant microorganism as provided herein that produces more lipid and/or exhibits increased partitioning of carbon to lipid compared to a control microorganism can have attenuated and/or altered expression and/or function of a gene encoding a polypeptide that comprises an amino acid sequence having at least about 50%, at least 55%, at least 60%, at least 65%, at least 70%, at least 75%, at least 80%, at least 85%, at least 90%, at least 95%, at least 96%, at least 97%, at least 98%, or at least about 99% identity to SEQ ID NO:2. In other embodiments, the mutant microorganism has attenuated expression of a gene encoding a polypeptide that includes the amino acid sequence set forth in SEQ ID NO:2, or a conservative variant thereof. In some embodiments, the mutant microorganism has attenuated expression of a gene encoding a polypeptide having the amino acid sequence set forth in SEQ ID NO:2.

In some embodiments, the mutant microorganisms provided herein (for example, microorganisms obtained by classical mutagenesis or genetic engineering) produce at least about 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 100%, at least 110%, at least 120%, at least 130%, at least 140%, at least 150%, at least 160%, at least 170%, at least 180%, at least 190%, at least 200%, at least 210%, at least 220%, at least 230%, at least 240%, or at least about 250% more lipid with respect to a control microorganism when both the mutant microorganism and control microorganism are cultured under substantially identical. For example, the mutant microorganism can produce between about 25% and about 250% more, between about 25% and about 225% more, between about 25% and about 200% more, between about 25% and about 175% more, between about 25% and about 150% more, between about 25% and about 125% more, between about 50% and about 250% more, between about 50% and about 225% more, between about 50% and about 200% more, between about 50% and about 175% more, between about 50% and about 150% more, between about 50% and about 125% more, between about 75% and about 250% more, between about 75% and about 225% more, between about 75% and about 200% more, or between about 75% more and about 175% more, between about 75% more and about 150% more, or between about 75% and about 125% more (e.g., 25-250% more) lipid with respect to a control microorganism when both the mutant microorganism and control microorganism are cultured under substantially identical conditions in which the control microorganism culture produces biomass. The culture conditions can be nitrogen replete, and can be nutrient replete, with respect to the control microorganism. In some embodiments the control microorganism is a wild type microorganism of the same species from which the mutant is directly or indirectly derived, and the culture conditions are nitrogen replete, and can be nutrient replete, with respect to the wild type microorganism.

The culture conditions under which a mutant as provided herein produces more lipid or demonstrates greater partitioning of carbon to lipid than a control microorganism can be batch, semi-continuous, or continuous conditions that may be nitrogen replete, nitrogen limited (for example, where a nitrogen source is present at less than about 5 mM, less than about 4 mM, less than about 3 mM, less than about 2 mM, less than about 1 mM, or less than about 0.5 mM concentration) or nitrogen deplete (substantially free of a nitrogen source). In some embodiments, the conditions under which a mutant microorganism having attenuated expression of a gene encoding a polypeptide that includes a GAF2 domain or having at least 50%, 60%, 70%, 80%, 85%, 90%, or 95% identity to SEQ ID NO:2 produces more lipid that a control strain are conditions in which nitrate is present as substantially the sole nitrogen source in the culture medium.

In some embodiments, a mutant microorganism as disclosed herein produces at least about 15%, at least 20%, at least about 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 100%, at least 110%, or at least about 120% more storage lipids, such as for example, triacylglycerols (TAGs), than the control microorganism, e.g., under conditions where nitrate is substantially the sole nitrogen source and both the mutant and control microorganisms are producing biomass.

In some embodiments, a mutant microorganism as provided herein can demonstrate greater lipid productivity than a control microorganism over a culture period of at least about three days, for example, over a culture period of at least about four, at least about five, at least about six, at least about seven, at least about eight, at least about nine, at least about ten, at least about eleven, at least about twelve, at least about thirteen, at least about fourteen, at least about fifteen, at least about twenty, at least about thirty, or at least about sixty days when the mutant microorganism and the control microorganism are cultured under substantially identical conditions that support growth and propagation of the control microorganism, i.e., under conditions in which the control microorganism culture produces biomass. In some examples the culture period in which a mutant microorganism as provided herein produces at least about 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 100%, at least 110%, at least 120%, at least 130%, at least 140%, at least 150%, at least 160%, at least 170%, at least 180%, at least 190%, at least 200%, at least 210%, at least 220%, at least 230%, at least 240%, or at least about 250% more lipid with respect to a control microorganism can be less than 180 days, less than 120 days, or less than 90 days, where the mutant can have a higher average daily lipid productivity over the time period. For example, a mutant microorganism as provided herein can produce at least about 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 100%, at least 110%, at least 120%, at least 130%, at least 140%, at least 150%, at least 160%, at least 170%, at least 180%, at least 190%, at least 200%, at least 210%, at least 220%, at least 230%, at least 240%, or at least about 250% more lipid than a control microorganism during a culture period of from three to 90 days, from three to 60 days, from three to thirty days, or from three to fifteen days. For example, a mutant microorganism as provided herein can produce at least about 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 100%, at least 110%, at least 120%, at least 130%, at least 140%, at least 150%, at least 160%, at least 170%, at least 180%, at least 190%, at least 200%, at least 210%, at least 220%, at least 230%, at least 240%, or at least about 250% more lipid than a control microorganism during a culture period ranging from about five to about 90 days, from about five to about 60 days, from about five to about thirty days, or from about five to about fifteen days, or from about seven to about 90 days, from about seven to about 60 days, from about seven to about thirty days, from about seven to about twenty days, or from about seven to about fifteen days.

The amount of lipid produced by a microorganism can be determined by removing samples of culture at any point during the culture period, for example, at the end of the culture period or at intervals during the culture period, such as daily, every other day, etc. Productivity can be volumetric productivity, for example, the productivity of a culture can be expressed as weight per milliliter or liter of culture, and can be a daily productivity (e.g., mg/liter/day or g/liter/day), for example, an average daily productivity over multiple days of the culture (for example, at least about three, four, five, six, seven, eight, nine, ten, eleven, twelve, thirteen, fourteen fifteen, or more days), or can be a total amount produced per unit volume for a defined period of time in culture. Productivity is preferably measured multiple times during the culture period, for example, at least about twice or at least about three times, and may be assessed every day, every other day, every third day, etc.

Biomass productivity can be assessed, for example, by measuring total organic carbon (TOC) or by other methods, such as measuring dry weight or ash-free dry weight (AFDW). Methods for measuring TOC are known in the art (e.g., U.S. Pat. No. 8,835,149) and are provided herein. Methods of measuring AFDW are also well-known and can be found, for example, in U.S. Pat. No. 8,940,508, incorporated herein by reference in its entirety.

Methods of measuring the amount of lipid produced by microorganisms are also well-known in the art and provided in the examples herein. For example, total extractable lipid can be determined according to Folch et al. (1957) *J. Biol. Chem.* 226: 497-509; Bligh & Dyer (1959) *Can. J. Biochem. Physiol.* 37: 911-917; or Matyash et al. (2008) *J. Lipid Res.* 49:1137-1146, for example, and the percentage of biomass present as lipid can also be assessed using Fourier transform infrared spectroscopy (FT-IR) (Pistorius et al. (2008) *Biotechnol & Bioengin.* 103:123-129). Additional references for gravimetric analysis of FAME and TAGs are provided in U.S. Pat. No. 8,207,363 and WO 2011127118 for example, each incorporated herein by reference in its entirety.

In some embodiments, a mutant microorganism as provided herein produces an average of at least about 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 100%, at least 110%, at least 120%, at least 130%, at least 140%, at least 150%, at least 160%, at least 170%, at least 180%, at least 190%, at least 200%, at least 210%, at least 220%, at least 230%, at least 240%, or at least about 250% more FAME lipids over the length of the culture period or per day with respect to a control microorganism, when the mutant microorganism and control microorganism are cultured under the same culture conditions, where the culture conditions are nitrogen-replete, and are preferably nutrient replete culture conditions with respect to the control microorganism, over a period of at least about three days, at least about four days, at least about five days, at least about seven days, at least about ten days, at least about twelve days, or at least about fourteen days, and can be culture conditions in which both the mutant and control microorganism are producing biomass.

The culture conditions can include culturing in a culture medium that includes less than about 5 mM, less than about 4.5 mM, less than about 4 mM, less than about 3.5 mM, less than about 3 mM, less than about 2.5 mM, less than about 2 mM, less than about 1.5 mM, less than about 1 mM, less than about 0.5 mM (e.g., less than 5 mM), or substantially none of a reduced nitrogen source such as ammonium. For example, the ammonium concentration may be at a concentration ranging from about 0 to about 5 mM, from about 0 to about 4.5 mM, from about 0 to about 4.0 mM, from about 0 to about 3.5 mM, from about 0 to about 3 mM, from about 0 to about 2.5 mM, from about 0 to about 2.0 mM, from about 0 to about 1.5 mM, from about 0 to about 1.0 mM, or from about 0 to about 0.5 mM (e.g., 0-5 mM). The ammonium concentration may be at a concentration ranging from about 0.2 to about 3 mM, 0.2 to about 2.5 mM, from about 0.2 to about 2 mM, from about 0.2 to about 1.5 mM, about 0.2 to about 1 mM, from about 0.3 to about 2.5 mM, from about 0.3 to about 2 mM, from about 0.3 to about 1.5 mM, or from about 0.3 to about 1 mM (e.g., 0.2-3 mM). In further examples, the ammonium concentration may be at a concentration ranging from about 0.4 mM to about 2.5 mM, from about 0.4 to about 2 mM, or from about 0.4 mM to about 1.5 mM (e.g., 0.4-2.5 mM). Alternatively or in addition, the culture conditions can include culturing in a culture medium that includes nitrate as substantially the sole source of nitrogen. The control microorganism in some examples is a wild type microorganism, e.g., a wild type microorganism from which the mutant microorganism is directly or indirectly derived.

In some embodiments, a mutant microorganism as provided herein is an algal microorganism that produces at least about 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 100%, at least 110%, at least 120%, at least 130%, at least 140%, at least 150%, at least 160%, at least 170%, at least 180%, at least 190%, at least 200%, at least 210%, at least 220%, at least 230%, at least 240%, or at least about 250% more FAME lipids than a control alga when cultured under photoautotrophic conditions in a medium that includes less than about 5 mM, less than about 4.5 mM, less than about 4 mM, less than about 3.5 mM, less than about 3 mM, less than about 2.5 mM ammonium, less than about 2.0 mM, less than about 1.5 mM ammonium, less than about 1.0 mM ammonium, less than about 0.5 mM ammonium (e.g., less than 5 mM), or substantially no ammonium, and includes, for example, at least about 1.0 mM, at least about 2.0 mM, at least about 3.0 mM, at least about 4.0 mM, at least about 5.0 mM, at least about 6.0 mM, at least about 7.0 mM, at least about 8.0 mM, at least about 9.0 mM, or at least about 10.0 mM nitrate (e.g., at least 1.0 mM). For example, the ammonium concentration may be at a concentration ranging from about 0 to about 5 mM, from about 0 to about 4.5 mM, from about 0 to about 4.0 mM, from about 0 to about 3.5 mM, from about 0 to about 3 mM, from about 0 to about 2.5 mM, from about 0 to about 2.0 mM, from about 0 to about 1.5 mM, from about 0 to about 1.0 mM, or from about 0 to about 0.5 mM (e.g., 0-5 mM). The ammonium concentration may be at a concentration ranging from about 0.2 to about 3 mM, 0.2 to about 2.5 mM, from about 0.2 to about 2 mM, from about 0.2 to about 1.5 mM, about 0.2 to about 1 mM, from about 0.3 to about 2.5 mM, from about 0.3 to about 2 mM, from about 0.3 to about 1.5 mM, or from about 0.3 to about 1 mM (e.g., 0.2-3 mM). In further examples, the ammonium concentration may be at a concentration ranging from about 0.4 mM to about 2.5 mM, from about 0.4 to about 2 mM, or from about 0.4 mM to about 1.5 mM (e.g., 0.4-2.5 mM). The culture conditions can in some examples include substantially no ammonium, and in some examples can include substantially no reduced nitrogen as a nitrogen source. The culture in some examples includes nitrate as a nitrogen source, which can optionally be substantially the sole nitrogen source in the culture medium. The photoautotrophic conditions may be under a diel cycle. The light period of the diel cycle may be of any length and can be, for example, from about four hours to about twenty-two hours, and can be, for example, from about six hours to about twenty hours, e.g., from about eight hours to about eighteen hours per twenty-four hour cycle. The microorganism can be exposed to natural or artificial light or a combination thereof. The available light can vary in intensity throughout the light period.

Mutant microorganisms provided herein can have greater partitioning of carbon to lipid with respect to a control microorganism cultured under identical conditions in which both the control microorganism and the mutant microorganism are producing biomass. A mutant having increased partitioning of carbon to lipid with respect to a control microorganism can have increased partitioning of carbon to total extractable lipid, to total neutral lipids, to triglycerides, and/or to FAME-derivatizable lipids. In some examples, a mutant microorganism as provided herein can have a ratio of the amount of FAME-derivatizable lipids ("FAME") produced to biomass (TOC or ash-free dry weight (AFDW), for example) produced that is at least about 50%, at least 60%, at least 70%, at least 80%, at least 90%, at least 100%, at least 120%, at least 140%, at least 160%, at least 180%, at least 200%, at least 220%, at least 240%, at least 260%, at least 280%, at least 300%, at least 320%, at least 340%, at least 360%, at least 380%, or at least 400% higher than that of a control microorganism. For example, the mutant microorganism can have a ratio of the amount of FAME-derivatizable lipids ("FAME") produced to biomass (TOC or ash-free dry weight (AFDW), for example) produced that is between about 50% higher to about 400% higher, about 50% higher to about 375% higher, about 50% higher to about 350% higher, about 50% higher to about 325% higher, about 50% higher to about 300% higher, about 50% higher to about 275% higher, about 50% higher to about 250% higher, about 50% higher to about 225% higher, about 75% higher to about 400% higher, about 75% higher to about 375% higher, about 75% higher to about 350% higher, about 75% higher to about 325% higher, about 75% higher to about 300% higher, about 75% higher to about 275% higher, about 75% higher to about 250% higher, or about 75% higher to about 225% higher (e.g., 50-400% higher) lipid productivity with respect to a control microorganism when both the mutant microorganism and control microorganism are cultured under substantially identical conditions in which the control microorganism culture produces biomass. Lipid and biomass production and/or production can be assessed, for example, by gravimetric analysis as known in the art and demonstrated in the examples herein. For example, a mutant microorganism as provided herein can have a ratio of FAME to TOC that is at least about 50%, at least 60%, at least 70%, at least 80%, at least 90%, at least 100%, at least 120%, at least 140%, at least 160%, at least 180%, at least 200%, at least 220%, at least 240%, at least 260%, at least 280%, at least 300%, at least 320%, at least 340%, at least 360%, at least 380%, or at least about 400% higher than the FAME/TOC ratio of a control microorganism when both the mutant microorganism and the control microorganism are cultured under the same conditions. In some embodiments, the FAME/TOC ratio is about 50-400% higher in the mutant microorganism than in the control microorganism.

In various examples, the FAME/TOC ratio of a mutant microorganism as provided herein can be, for example, at least about 0.30, at least about 0.35, at least about 0.40, at least about 0.45, at least about 0.50, at least about 0.55, at least about 0.60, at least about 0.65, at least about 0.70, at least about 0.75, at least about 0.80, at least about 0.85, or at least about 0.90 (e.g., at least any of 0.30, 0.50, 0.75, or 0.90) when cultured under conditions that are nitrogen replete, for example, nutrient replete, with respect to the control microorganism. The culture conditions can include, for example, a culture medium that includes less than about 5 mM, less than about 4.5 mM, less than about 4 mM, less than about 3.5 mM, less than about 3 mM, less than about 2.5 mM, less than about 2 mM, less than about 1.5 mM, less than about 1.0 mM, or less than about 0.5 mM (e.g., less than 5 mM) ammonium and in some examples can include at least about 1.0 mM, at least about 2.0 mM, at least about 3.0 mM, at least about 4.0 mM, at least about 5.0 mM, at least about 6.0 mM, at least about 7.0 mM, at least about 8.0 mM, at least about 9.0 mM, or at least about 10.0 mM (e.g., at least 1.0 mM) nitrate. The culture conditions can in some examples include substantially no ammonium, and in some examples can include substantially no reduced nitrogen as a nitrogen source. The culture in some examples includes nitrate as a nitrogen source, which can optionally be substantially the sole nitrogen source in the culture medium. In an illustrative embodiment, the mutant microorganism exhibits a FAME/TOC ratio of at least about 0.35.

The properties of a mutant as provided herein having increased lipid production are compared to the same properties of a control microorganism that may be a wild type organism of the same species as the mutant, preferably the progenitor strain of the lipid-overproducing mutant. Alternatively, a control microorganism can be a microorganism that is substantially identical to the mutant microorganism with the exception that the control microorganism does not have the mutation that leads to higher lipid productivity. For example, a control microorganism can be a genetically engineered microorganism or classically mutated organism that has been further mutated or engineered to generate a mutant having increased lipid productivity and/or increased lipid partitioning as disclosed herein.

In some examples, a control microorganism can be a microorganism that is substantially identical to the mutant microorganism, with the exception that the control microorganism does not have a mutation in a gene that regulates lipid induction (i.e., a gene encoding a polypeptide having a GAF2 domain, a gene encoding a polypeptide that includes an amino acid sequence having at least 50% identity to SEQ ID NO:1, and/or a gene encoding a polypeptide having at least 50% identity to SEQ ID NO:2, whose mutation results in increased lipid production). The properties of a lipid-overproducing mutant having a disrupted, attenuated, or otherwise directly or indirectly genetically manipulated gene (resulting in altered structure or expression of the lipid induction regulator gene) are also be compared with the same properties of a control cell that does not have a disrupted, attenuated, or otherwise directly or indirectly genetically manipulated lipid induction regulator gene resulting in altered structure or expression of the lipid induction regulator gene (regardless of whether the cell is "wild type"). For example, a control cell may be a recombinant cell that includes one or more non-native genes or a cell mutated in a gene other than the lipid induction regulator gene whose effects are being assessed, etc.

The mutant microorganism can be of any eukaryotic microalgal strain such as, for example, any species of any of the genera *Achnanthes, Amphiprora, Amphora, Ankistrodesmus, Asteromonas, Boekelovia, Bolidomonas, Borodinella, Botrydium, Botryococcus, Bracteococcus, Chaetoceros, Carteria, Chlamydomonas, Chlorococcum, Chlorogonium, Chlorella, Chroomonas, Chrysosphaera, Cricosphaera, Crypthecodinium, Cryptomonas, Cyclotella, Desmodesmus, Dunaliella, Elipsoidon, Emiliania, Eremosphaera, Ernodesmius, Euglena, Eustigmatos, Franceia, Fragilaria, Fragilaropsis, Gloeothamnion, Haematococcus, Hantzschia, Heterosigma, Hymenomonas, Isochrysis, Lepocinclis,*

*Micractinium, Monodus, Monoraphidium, Nannochloris, Nannochloropsis, Navicula, Neochloris, Nephrochloris, Nephroselmis, Nitzschia, Ochromonas, Oedogonium, Oocystis, Ostreococcus, Parachlorella, Parietochloris, Pascheria, Pavlova, Pelagomonas, Phceodactylum, Phagus, Picochlorum, Platymonas, Pleurochrysis, Pleurococcus, Prototheca, Pseudochlorella, Pseudoneochloris, Pseudostaurastrum, Pyramimonas, Pyrobotrys, Scenedesmus, Schizochlamydella, Skeletonema, Spyrogyra, Stichococcus, Tetrachlorella, Tetraselmis, Thalassiosira, Tribonema, Vaucheria, Viridiella, Vischeria*, and *Volvox*. Non-limiting examples of particularly suitable species include, for instance, diatoms such as, for example, a species of any of the genera *Amphora, Chaetoceros, Cyclotella, Fragilaria, Fragilaropsis, Hantzschia, Monodus, Navicula, Nitzschia, Phceodactylum*, or *Thalassiosira*, or Eustigmatophytes, e.g., *Eustigmatos, Nannochloropsis, Pseudostaurastrum*, or *Vischeria*.

In some examples, the recombinant alga is a green alga, i.e., an algal member of the Chlorophyte division of the Viridiplantae kingdom, including without limitation, a microalga of any of the classes Chlorophyceae, Chlorodendrophyceae, Pedinophyceae, Pleurastrophyceae, Prasinophyceae, and Trebouxiophyceae. In some examples, a recombinant alga as provided herein can be a species that is a member of any of the Chlorophyceae, Prasinophyceae, Trebouxiophyceae, or Chlorodendrophyceae classes, such as a species of any of the *Asteromonas, Ankistrodesmus, Carteria, Chlamydomonas, Chlorococcum, Chlorogonium, Chrysosphaera, Desmodesmus, Dunaliella, Haematococcus, Monoraphidium, Neochloris, Oedogonium, Pelagomonas, Pleurococcus, Pyrobotrys, Scenedesmus, Volvox, Micromonas, Ostreococcus Prasinocladus Scherffelia, Tetraselmis, Botryococcus, Chlorella, Eremosphaera, Franceia, Micractinium, Nannochloris, Oocystis, Parachlorella, Picochlorum, Prototheca*, or *Pseudochlorella* genera. In various examples, a recombinant alga as provided herein can be a species or strain of the Trebouxiophyceae, such as but not limited to *Botryococcus, Chlorella, Eremosphaera, Franceia, Micractinium, Nannochloris, Oocystis, Parachlorella, Picochlorum, Prototheca*, or *Pseudochlorella*.

In some examples, the recombinant alga is a heterokont alga, and may belong to the diatoms (bacillariophytes), eustigmatophytes, xanthophytes, phaeophytes, chrysophytes, or raphidophytes. In some examples, the mutant alga belongs to a Bacillariophyte or Eustigmatophyte genus such as but not limited to *Amphiprora, Amphora, Chaetoceros, Cyclotella, Fragilaria, Fragilaropsis, Hantzschia, Monodus, Nannochloropsis, Navicula, Nitzschia, Phceodactylum, Phceodactylum, Pseudostaurastrum, Vischeria, Phceodactylum, Skeletonema*, and *Thalassiosira*. In some examples, the mutant alga is a Eustigmatophyte and belongs to a genus selected from the group consisting of *Chloridella, Chlorobptrys, Ellipsoidion, Eustigmatos, Goniochloris, Monodopsis, Monodus, Nannochloropsis, Pseudocharaciopsis, Pseudostaruastrum, Pseudotetraedriella*, and *Vischeria*. In some examples, the mutant alga cell is a *Nannochloropsis* species.

Alternatively, a mutant microorganism as provided herein may be a heterokont that is a Labyrinthulomycete microorganism, e.g., a member of the Labrinthulids or Thraustochytrids, such as, for example, a species of any of the genera *Labryinthula, Labryinthuloides, Thraustochytrium, Schizochytrium, Aplanochytrium, Aurantiochytrium, Oblongichytrium, Japonochytrium, Diplophrys*, and *Ulkenia*.

The mutants can be spontaneous mutants, classically-derived mutants, or engineered mutants having attenuated expression of a regulator gene, for example, a gene whose expression affects the expression of many other genes such as a gene encoding a transcription factor or a transcriptional activator.

The mutant microorganism having attenuated expression of a gene that regulates lipid production can be a "knockout" mutant, for example, in which the reading frame of the polypeptide is disrupted such that the functional protein is not produced. For example, the gene can include an insertion, deletion, or mutation in the reading frame that results in no functional protein being made. In various examples, a knockout mutation can be generated by insertion of a sequence, often but not necessarily including a selectable marker gene, into the gene, for example, into the coding region of the gene. Such an insertion can be by use of a cas/CRISPR system that integrates a donor fragment into a targeted locus, or can be by homologous recombination, for example. Such an insertion can disrupt an open reading frame and/or splicing signals, or generate nonfunctional fusion proteins or truncated proteins. In other examples, the mutant microorganism can be a "knockdown" mutant in which expression of the gene is reduced but not eliminated, for example, reduced from 5% or less to 95% or more, for example, from 5% to 95% or 10% to 90%, with respect to expression levels of a wild type cell. Knockdowns can be mutants in which a mutation, insertion, or deletion occurs in a non-coding region of the gene, for example, the 5' or 3' region of a gene, or can be effected by expressing constructs in the cells that reduce expression of the targeted gene, such as RNAi, ribozyme, or antisense constructs. In addition to CRISPR systems, homologous recombination, transposable elements, or random integration can be used to generate insertion mutants (either knockdown or knockout).

A mutant microorganism as provided herein can be designed by targeting an endogenous gene of a microorganism of interest that encodes a polypeptide that includes a GAF (e.g., GAF2) domain as disclosed herein. Such genes can be identified in a microorganism of interest using bioinformatics methods, molecular biology techniques and combinations thereof. For example, a gene encoding a polypeptide that includes a GAF (e.g., GAF2) domain can be identified using Southern hybridization, screening of cDNA libraries by hybridization, or PCR, for example, using degenerate probes and/or primers. Genome sequences available in public or proprietary databases can be searched by any of a number of programs that perform sequence matching (e.g., blast programs such as blastp, blastn, and tblastn (protein sequence queried against translated nucleotide sequence)) or analyze domain structures of encoded amino acid sequences. For example, HMMER provides software online for analyzing structural and functional domains encoded by genes that can be used to scan genome sequences, including, for example, hmmsearch and hmmscan. Such searches can be done online. Programs such as MUSCLE and hmmalign can also be used to search for orthologs of proteins such as the proteins disclosed herein (e.g., GAF (e.g., GAF2) domain-containing polypeptides) by constructing phylogenetic trees to determine relationships among proteins. Gene targeting can make use of sequences identified in the genome of the microorganism of interest. It is not necessary to resolve the complete structure of a gene to target the gene for attenuation. For example, using methods disclosed herein, including, without limitation, genome editing (using meganucleases, zinc finger nucleases, TALENs, or Cas/CRISPR systems), RNAi constructs, antisense constructs, homologous recombination constructs, and ribozyme constructs, only a portion of a gene sequence can be employed in gene attenuation constructs and techniques.

In some embodiments, the mutant microorganism can be further engineered or mutagenized to have at least one additional genetic modification that confers herbicide resistance, toxin resistance, enhanced growth properties, enhanced photosynthetic efficiency, enhanced lipid production or accumulation, and production of particular lipids.

Gene Attenuation

A mutant microorganism as provided herein having attenuated expression of a gene that regulates lipid biosynthesis is a mutant generated by human intervention, for example, by classical mutagenesis or genetic engineering. Methods for generating mutants of microbial strains are well-known in the art. For example, a mutant microorganism as provided herein can be a mutant generated by any feasible mutagenesis method, including but not limited to UV irradiation, gamma irradiation, or chemical mutagenesis. Screening for mutants having increased lipid production can be, for example, by staining with lipophilic dyes such as Nile Red or BODIPY as known in the art (e.g., Cabanelas et al. (2015) *Bioresource Technology* 184:47-52), or by quantitating lipid produced by the strains using analytical biochemistry methods known in the art or disclosed herein.

In one aspect this disclosure provides genetically modified organisms, e.g., microorganisms having one or more genetic modifications or mutations for attenuating expression of a naturally-occurring lipid regulator gene such as a naturally-occurring gene encoding a polypeptide having a GAF domain (e.g., a GAF2 domain) that in a wild type organism has at least about 50%, at least 55%, at least 60%, at least 65%, at least 70%, at least 75%, at least 80%, at least 85%, at least 90%, at least 95%, at least 96%, at least 97%, at least 98%, or at least about 99% identity to SEQ ID NO:1; a naturally-occurring gene encoding a polypeptide that in a wild type organism has at least about 50%, at least 55%, at least 60%, at least 65%, at least 70%, at least 75%, at least 80%, at least 85%, at least 90%, at least 95%, at least 96%, at least 97%, at least 98%, or at least about 99% identity to SEQ ID NO:2; a naturally-occurring gene localized to the Naga_100020g79 locus or a syntenic locus in a heterokont or algal species; and/or a naturally-occurring gene having a coding region with at least about 50%, at least 55%, at least 60%, at least 65%, at least 70%, at least 75%, at least 80%, at least 85%, at least 90%, at least 95%, at least 96%, at least 97%, at least 98%, or at least about 99% identity to SEQ ID NO:3. As used herein "attenuating" or "altering" the expression and/or function of a gene (e.g., a "lipid regulator gene") means reducing or eliminating expression of the gene in any manner that reduces production, expression and/or function of the normally expressed fully functional protein. Means for attenuating a gene such as a lipid regulator gene include, for example, homologous recombination constructs; CRISPR systems, including guide RNAs, Cas9 or other cas enzymes, and optionally, donor fragments for insertion into the targeted site; RNAi constructs, including shRNAs, antisense RNA constructs; ribozyme constructs; TALENS, Zinc Finger nucleases; and meganucleases. For instance, in some embodiments, the gene can be disrupted by, for example, an insertion or gene replacement mediated by homologous recombination and/or by the activity of a double strand break inducing agent such as meganuclease (see, e.g., WO 2012/017329 (US 2013/0164850) and US 2016/0272980), zinc finger nuclease (Perez-Pinera et al. (2012) *Curr. Opin. Chem. Biol.* 16: 268-277; WO 2012/017329 (US 2013/ 0164850); and US 2012/0324603), TALEN (WO 2014/ 207043 (US 2016/0130599); WO 2014/076571 (US 2016/ 0272980)), or a cas protein (e.g., a Cas9 protein) of a CRISPR system (see e.g., U.S. Pat. Nos. 8,697,359; 8,795, 965; 8,889,356; US 2016/0304893; US 2016/0090603; US 2014/0068797). Other methods of disruption are known in the art and would be suitable here as would be understood by those of ordinary skill in the art.

In some embodiments, the mutant microorganism has one or more mutations to or affecting the expression of a gene localized to the Naga_100020g79 locus or a syntenic locus in a heterokont or algal species. In some embodiments, the mutant microorganism has a mutation to, or a mutation that affects the expression of, a gene having an open reading frame having at least about 50%, at least 55%, at least 60%, at least 65%, at least 70%, at least 75%, at least 80%, at least 85%, at least 90%, at least 95%, at least 96%, at least 97%, at least 98%, or at least about 99% identity to SEQ ID NO:3. In some embodiments, the mutant microorganism has one or more mutations that are present in or affect expression of: a nucleic acid encoding a polypeptide comprising an amino acid sequence of at least about 50%, at least 55%, at least 60%, at least 65%, at least 70%, at least 75%, at least 80%, at least 85%, at least 90%, at least 95%, at least 96%, at least 97%, at least 98%, or at least about 99% identity to SEQ ID NO:1 or SEQ ID NO:2; and/or a nucleic acid having an open reading frame that comprises a nucleotide sequence of at least about 50%, at least 55%, at least 60%, at least 65%, at least 70%, at least 75%, at least 80%, at least 85%, at least 90%, at least 95%, at least 96%, at least 97%, at least 98%, or at least about 99% identity to SEQ ID NO:3. In some embodiments, the mutant microorganism has one or more mutations in the GAF2 domain of the gene in the Naga_100020g79 locus or a chromosomal locus syntenic thereto (referred to herein as the STP-4551 gene or a homolog thereof).

A recombinant microorganism engineered to have attenuated expression of a lipid regulator gene can have a disrupted lipid regulator gene that includes as least one insertion, mutation, or deletion that reduces or abolishes expression of the gene such that a fully functional lipid regulator gene is not produced or is produced in lower amounts than is produced by a control microorganism that does not include a disrupted lipid regulator gene. For instance, in some embodiments, one or more mutations (change, deletion, and/or insertion of one or more nucleotides) can be in the coding region of the gene or can be in an intron, 3' UTR, 5' UTR, or promoter region, e.g., within about 2 kb of the transcriptional start site or within about 3 kb of the translational start site in a transcribed or non-transcribed portion of the gene. In some embodiments, for example, a mutant microorganism having attenuated expression of a gene as disclosed herein can have one or more mutations, which can be one or more nucleobase changes and/or one or more nucleobase deletions and/or one or more nucleobase insertions, into the region of a gene 5' of the transcriptional start site, such as, in non-limiting examples, within about 2 kb, within 1.5 kb, within 1 kb, or within 0.5 kb of the known or putative transcriptional start site, or within about 3 kb, within 2.5 kb, within 2 kb, within 1.5 kb, within 1 kb, or within about 0.5 kb of the translational start site. As non-limiting examples, a mutant gene can be a gene that has a mutation, insertion, or deletion within the promoter region that can either increase or decrease expression of the gene; can be a gene that has a deletion that results in production of a nonfunctional protein, truncated protein, dominant negative protein, or no protein; can be a gene that has one or more point mutations leading to a change in the amino acid of the encoded protein or results in aberrant splicing of the gene transcript, etc.

A mutant as provided herein that produces at least about 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 100%, at least 110%, at least 120%, at least 130%, at least 140%, at least 150%, at least 160%, at least 170%, at least 180%, at least 190%, at least 200%, at least 210%, at least 220%, at least 230%, at least 240%, or at least about 250% more lipid can also be a genetically engineered mutant, for example, a mutant in which a gene encoding a polypeptide having a GAF domain, such as for example the GAF2 domain, or a gene localized to the Naga_100020g79 locus or an ortholog thereof (e.g., a gene encoding a polypeptide having a GAF domain that has at least about 50%, at least 55%, at least 60%, at least 65%, at least 70%, at least 75%, at least 80%, at least 85%, at least 90%, at least 95%, at least 96%, at least 97%, at least 98%, or at least about 99% identity to SEQ ID NO:1 or a gene encoding a polypeptide having at least about 50%, at least 55%, at least 60%, at least 65%, at least 70%, at least 75%, at least 80%, at least 85%, at least 90%, at least 95%, at least 96%, at least 97%, at least 98%, or at least about 99% identity to SEQ ID NO:2) has been targeted by homologous recombination for knock-out, knockdown, or gene replacement (for example with mutated form of the gene that may encode a polypeptide having reduced activity with respect to the wild type polypeptide). For example, a microbial strain of interest may be engineered by site directed homologous recombination to insert a sequence into a genomic locus and thereby alter a gene and/or its expression, or to insert a promoter into a genetic locus of the host microorganism to affect the expression of a particular gene or set of genes at the locus.

For example, gene knockout, gene knockdown, or gene replacement by homologous recombination can be by transformation of a nucleic acid (e.g., DNA) fragment that includes a sequence homologous to the region of the genome to be altered, where the homologous sequence is interrupted by a foreign sequence, typically a selectable marker gene that allows selection for the integrated construct. The genome-homologous flanking sequences on either side of the foreign sequence or mutated gene sequence can be for example, at least about 50, at least 100, at least 200, at least 300, at least 400, at least 500, at least 600, at least 700, at least 800, at least 900, at least 1,000, at least 1,200, at least 1,500, at least 1,750, or at least about 2,000 nucleotides in length. A gene knockout or gene "knock in" construct in which a foreign sequence is flanked by target gene sequences, can be provided in a vector that can optionally be linearized, for example, outside of the region that is to undergo homologous recombination, or can be provided as a linear fragment that is not in the context of a vector, for example, the knock-out or knock-in construct can be an isolated or synthesized fragment, including but not limited to a PCR product. In some instances, a split marker system can be used to generate gene knock-outs by homologous recombination, where two DNA fragments can be introduced that can regenerate a selectable marker and disrupt the gene locus of interest via three crossover events (Jeong et al. (2007) *FEMS Microbiol Lett* 273: 157-163).

The CRISPR systems referred to herein, and reviewed recently by Hsu et al. (*Cell* 157:1262-1278, 2014) include, in addition to the cas nuclease polypeptide or complex, a targeting RNA, often denoted "crRNA", that interacts with the genome target site by complementarity with a target site sequence, a trans-activating ("tracr") RNA that complexes with the cas polypeptide and also includes a region that binds (by complementarity) the targeting crRNA. This disclosure contemplates the use of two RNA molecules (a "crRNA" and a "tracrRNA") that can be co-transformed into a host strain (or expressed in a host strain) that expresses or is transfected with a cas protein for genome editing, or the use of a single guide RNA that includes a sequence complementary to a target sequence as well as a sequence that interacts with a cas protein. That is, in some strategies a CRISPR system as used herein can comprise two separate RNA molecules (RNA polynucleotides: a "tracr-RNA" and a "targeter-RNA" or "crRNA", see below) and referred to herein as a "double-molecule DNA-targeting RNA" or a "two-molecule DNA-targeting RNA". Alternatively, as illustrated in the examples, the DNA-targeting RNA can also include the trans-activating sequence for interaction with the cas protein (in addition to the target-homologous ("cr") sequences), that is, the DNA-targeting RNA can be a single RNA molecule (single RNA polynucleotide) and is referred to herein as a "chimeric guide RNA," a "single-guide RNA," or an "sgRNA." The terms "DNA-targeting RNA" and "gRNA" are inclusive, referring both to double-molecule DNA-targeting RNAs and to single-molecule DNA-targeting RNAs (i.e., sgRNAs). Both single-molecule guide RNAs and two RNA systems have been described in detail in the literature and for example, in U.S. Patent Application Publication No. US 2014/0068797, incorporated by reference herein in its entirety. Some embodiments of the methods and compositions presented herein include a guide RNA that has a sequence corresponding to a target sequence in a gene localized to the Naga_100020g79 locus, such as for example, a target sequence having the sequence set forth in SEQ ID NO:5. In some embodiments, the guide RNA is a chimeric guide. In other embodiments, the guide RNA does not include a tracr sequence. Any cas protein can be used in the methods herein, e.g., Cas1, Cas1B, Cas2, Cas3, Cas4, Cas5, Cas6, Cas7, Cas8, Cas9 (also known as Csn1 and Csx12), Cas10, Cbf1, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Cpf1, Csb1, Csb2, Csb3, Csx17, Csx14, Csx10, Csx16, CsaX, Csx3, Csx1, Csx15, Csf1, Csf2, Csf3, Csf4, C2c1, C2c2, C2c3, and homologs thereof, or modified versions thereof. The cas protein can be a Cas9 protein, such as a Cas9 protein of *Staphylococcus pyogenes, S. thermophilus, S. pneumonia, S. aureus*, or *Neisseria meningitidis*, as nonlimiting examples. Also considered are the Cas9 proteins provided as SEQ ID NOs:1-256 and 795-1346 in U.S. Patent Application Publication No. US 2014/0068797, incorporated herein by reference in its entirety, and chimeric Cas9 proteins that may combine domains from more than one Cas9 protein, as well variants and mutants of identified Cas9 proteins.

Cas nuclease activity cleaves target DNA to produce double strand breaks. These breaks are then repaired by the cell in one of two ways: non-homologous end joining or homology-directed repair. In non-homologous end joining (NHEJ), the double-strand breaks are repaired by direct ligation of the break ends to one another. In this case, no new nucleic acid material is inserted into the site, although some nucleic acid material may be lost, resulting in a deletion, or altered, often resulting in mutation. In homology-directed repair, a donor polynucleotide (sometimes referred to as a "donor DNA" or "editing DNA") which may have homology to the cleaved target DNA sequence is used as a template for repair of the cleaved target DNA sequence, resulting in the transfer of genetic information from the donor polynucleotide to the target DNA. As such, new nucleic acid material may be inserted/copied into the site. The modifications of the target DNA due to NHEJ and/or homology-directed repair (for example using a donor DNA molecule) can lead to, for example, gene correction, gene replacement, gene tagging, transgene insertion, nucleotide deletion, gene disruption, gene mutation, etc.

In some instances, cleavage of DNA by a site-directed modifying polypeptide (e.g., a cas nuclease, zinc finger nuclease, meganuclease, or TALEN) may be used to add, delete, or alter the sequence of nucleic acid material from a target DNA sequence by cleaving the target DNA sequence and allowing the cell to repair the sequence in the absence of an exogenously provided donor polynucleotide. Such NHEJ events can result in mutations ("mis-repair") at the site of rejoining of the cleaved ends that can resulting in gene disruption.

If a DNA-targeting RNA is co-administered to cells that express a cas nuclease along with a donor DNA, the subject methods may be used to add, i.e. insert or replace, nucleic acid material to a target DNA sequence (e.g., "knock out" by insertional mutagenesis, or "knock in" a nucleic acid that encodes a protein (e.g., a selectable marker, reporter gene, and/or any protein of interest), an siRNA, a miRNA, etc., to modify a nucleic acid sequence (e.g., introduce a mutation), and the like.

A donor DNA can in particular embodiments include a gene regulatory sequence (e.g., a promoter) that can, using CRISPR targeting, be inserted upstream of the coding regions of the gene and upstream of the presumed proximal promoter region of the gene, for example, at least about 50 bp, at least 100 bp, at least 120 bp, at least 150 bp, at least 200 bp, at least 250 bp, at least 300 bp, at least 350 bp, at least 400 bp, at least 450 bp, or at least 500 bp upstream of the initiating ATG of the coding region of the lipid regulator gene. The donor DNA can include a sequence, such as for example a selectable marker or any convenient sequence, that may be interfere with the native promoter. The additional sequence inserted upstream of the initiating ATG of the lipid regulator open reading frame (e.g., in the 5'UTR or upstream of the transcriptional start site of the lipid regulator gene) can decrease or even eliminate expression of the endogenous lipid regulator gene. Alternatively, or in addition, the native lipid regulator gene can have its endogenous promoter wholly or partially replaced by a weaker or differently regulated promoter, or a non-promoter sequence.

In some examples, a nucleic acid molecule introduced into a host cell for generating a high efficiency genome editing cell line encodes a Cas9 enzyme that is mutated to with respect to the corresponding wild-type enzyme such that the mutated Cas9 enzyme lacks the ability to cleave one or both strands of a target polynucleotide containing a target sequence. For example, an aspartate-to-alanine substitution (D10A) in the RuvC I catalytic domain of Cas9 from *S. pyogenes* converts Cas9 from a nuclease that cleaves both strands to a nickase (an enzyme that cleaves a single strand). Other examples of mutations that render Cas9 a nickase include, without limitation, H840A, N854A, and N863A. In some embodiments, a Cas9 nickase may be used in combination with guide sequence(s), e.g., two guide sequences, which target respectively sense and antisense strands of the DNA target. This combination allows both strands to be nicked and used to induce NHEJ. Two nickase targets (within close proximity but targeting different strands of the DNA) can be used to inducing mutagenic NHEJ. Such targeting of a locus using enzymes that cleave opposite strands at staggered positions can also reduce nontarget cleavage, as both strands must be accurately and specifically cleaved to achieve genome mutation. In additional examples, a mutant Cas9 enzyme that is impaired in its ability to cleave DNA can be expressed in the cell, where one or more guide RNAs that target a sequence upstream of the transcriptional or translational start site of the targeted gene are also introduced. In this case, the cas enzyme may bind the target sequence and block transcription of the targeted gene (Qi et al. (2013) *Cell* 152:1173-1183). This CRISPR interference of gene expression can be referred to as RNAi and is also described in detail in Larson et al. (2013) *Nat. Protoc.* 8: 2180-2196. In some cases, a cas polypeptide such as a Cas9 polypeptide is a fusion polypeptide, comprising, e.g.: i) a Cas9 polypeptide (which can optionally be variant Cas9 polypeptide as described above); and b) a covalently linked heterologous polypeptide (also referred to as a "fusion partner"). A heterologous nucleic acid sequence may be linked to another nucleic acid sequence (e.g., by genetic engineering) to generate a chimeric nucleotide sequence encoding a chimeric polypeptide. In some embodiments, a Cas9 fusion polypeptide is generated by fusing a Cas9 polypeptide with a heterologous sequence that provides for subcellular localization (i.e., the heterologous sequence is a subcellular localization sequence, e.g., a nuclear localization signal (NLS) for targeting to the nucleus; a mitochondrial localization signal for targeting to the mitochondria; a chloroplast localization signal for targeting to a chloroplast; an ER retention signal; and the like). In some embodiments, the heterologous sequence can provide a tag (i.e., the heterologous sequence is a detectable label) for ease of tracking and/or purification (e.g., a fluorescent protein, e.g., green fluorescent protein (GFP), YFP, RFP, CFP, mCherry, tdTomato, and the like; a hemagglutinin (HA) tag; a FLAG tag; a Myc tag; and the like).

Host cells can be genetically engineered (e.g., transduced or transformed or transfected) with, for example, a vector construct that can be, for example, a vector for homologous recombination that includes nucleic acid sequences homologous to a portion of a lipid regulator gene locus of the host cell or to regions adjacent thereto, or can be an expression vector for the expression of any or a combination of: a cas protein (e.g., a Cas9 protein), a CRISPR chimeric guide RNA, a crRNA, and/or a tracrRNA, an RNAi construct (e.g., a shRNA), an antisense RNA, or a ribozyme. The vector can be, for example, in the form of a plasmid, a viral particle, a phage, etc. A vector for expression of a polypeptide or RNA for genome editing can also be designed for integration into the host, e.g., by homologous recombination. A vector containing a polynucleotide sequence as described herein, e.g., sequences having homology to host lipid regulator gene sequences (including sequences that are upstream and downstream of the lipid regulator-encoding sequences), as well as, optionally, a selectable marker or reporter gene, can be employed to transform an appropriate host to cause attenuation of a lipid regulator gene.

The recombinant microorganism in some examples can have reduced but not abolished expression of the lipid regulator gene, and the recombinant microorganism can have an increase in lipid production of from about 25% to about 250% or more, for example. For example, the increase in lipid production can be between about 25% more to about 250% more, about 25% more to about 225% more, about 25% more to about 200% more, about 25% more to about 175% more, about 25% more to about 150% more, about 25% more to about 125% more, about 50% more to about 250% more, about 50% more to about 225% more, about 50% more to about 200% more, about 50% more to about 175% more, about 50% more to about 150% more, about 50% more to about 125% more, about 75% more to about 250% more, about 75% more to about 225% more, about 75% more to about 200% more, or about 75% more to about 175% more, about 75% more to about 150%, or about 75% more to about 125% more (e.g., 25-250% more) with respect to a control microorganism. A genetically modified microorganism as provided herein can in some examples include a nucleic acid construct for attenuating the expression of a lipid regulator gene, such as, for example, a gene encoding a polypeptide having a GAF domain, such as for example a GAF2 domain, that has at least about 50%, at least 55%, at least 60%, at least 65%, at least 70%, at least 75%, at least 80%, at least 85%, at least 90%, at least 95%, at least 96%, at least 97%, at least 98%, or at least about 99% identity to SEQ ID NO:1; or a gene encoding a polypeptide comprising an amino acid sequence having at least about 50%, at least 55%, at least 60%, at least 65%, at least 70%, at least 75%, at least 80%, at least 85%, at least 90%, at least 95%, at least 96%, at least 97%, at least 98%, or at least about 99% identity to SEQ ID NO:2. For example, a host microorganism can include a construct for expressing an RNAi molecule, ribozyme, or antisense molecule that reduces expression of a lipid regulator gene encoding a polypeptide having a GAF domain that has at least about 50%, at least 55%, at least 60%, at least 65%, at least 70%, at least 75%, at least 80%, at least 85%, at least 90%, at least 95%, at least 96%, at least 97%, at least 98%, or at least about 99% identity to SEQ ID NO:1 or a lipid regulator gene encoding a polypeptide having at least about 50%, at least 55%, at least 60%, at least 65%, at least 70%, at least 75%, at least 80%, at least 85%, at least 90%, at least 95%, at least 96%, at least 97%, at least 98%, or at least about 99% identity to SEQ ID NO:2. In some examples, a recombinant microorganism as provided herein can include at least one introduced (exogenous or non-native) construct for reducing expression of a lipid regulator gene.

In some examples, engineered strains (e.g., genetically engineered strains) can be selected for expression of a lipid regulator gene that is decreased with respect to a control cell that does not include a genetic modification for attenuating lipid regulator gene expression, but not eliminated, using methods known in the art, such as, for example, RNA-Seq or reverse transcription-PCR (RT-PCR). A genetically engineered strain as provided herein can be engineered to include a construct for attenuating gene expression by reducing the amount, stability, or translatability of mRNA of a gene encoding a lipid regulator. For example, a microorganism such as an algal or heterokont strain can be transformed with an antisense RNA, RNAi, or ribozyme construct targeting an mRNA of a lipid regulator gene using methods known in the art. For example, an antisense RNA construct that includes all or a portion of the transcribed region of a gene can be introduced into a microorganism to decrease gene expression (Shroda et al. (1999) *The Plant Cell* 11:1165-78; Ngiam et al. (2000) *Appl. Environ. Microbiol.* 66: 775-782; Ohnuma et al. (2009) *Protoplasma* 236: 107-112; Lavaud et al. (2012) *PLoS One* 7:e36806). Alternatively or in addition, an RNAi construct (for example, a construct encoding a short hairpin RNA) targeting a gene having a GAF (e.g., GAF2) domain can be introduced into a microorganism such as an alga or heterokont for reducing expression of the lipid regulator gene (see, for example, Cerruti et al. (2011) *Eukaryotic Cell* (2011) 10: 1164-1172; Shroda et al. (2006) *Curr. Genet.* 49:69-84).

Ribozymes are RNA-protein complexes that cleave nucleic acids in a site-specific fashion. Ribozymes have specific catalytic domains that possess endonuclease activity. For example, U.S. Pat. No. 5,354,855 (incorporated herein in its entirety by reference) reports that certain ribozymes can act as endonucleases with a sequence specificity greater than that of known ribonucleases and approaching that of the DNA restriction enzymes. Catalytic RNA constructs (ribozymes) can be designed to base pair with an mRNA encoding a gene as provided herein to cleave the mRNA target. In some examples, ribozyme sequences can be integrated within an antisense RNA construct to mediate cleavage of the target. Various types of ribozymes can be considered, their design and use is known in the art and described, for example, in Haseloff et al. (1988) *Nature* 334:585-591. Ribozymes are targeted to a given sequence by virtue of annealing to a site by complimentary base pair interactions. Two stretches of homology are required for this targeting. These stretches of homologous sequences flank the catalytic ribozyme structure defined above. Each stretch of homologous sequence can vary in length from 7 to 15 nucleotides. The only requirement for defining the homologous sequences is that, on the target RNA, they are separated by a specific sequence which is the cleavage site. For hammerhead ribozyme, the cleavage site is a dinucleotide sequence on the target RNA is a uracil (U) followed by either an adenine, cytosine or uracil (A,C or U) (Thompson et al., (1995) *Nucl Acids Res* 23:2250-68). The frequency of this dinucleotide occurring in any given RNA is statistically 3 out of 16. Therefore, for a given target messenger RNA of 1,000 bases, 187 dinucleotide cleavage sites are statistically possible.

The general design and optimization of ribozyme directed RNA cleavage activity has been discussed in detail (Haseloff and Gerlach (1988) *Nature* 334:585-591; Symons (1992) *Ann Rev Biochem* 61: 641-71; Chowrira et al. (1994) *J Biol Chem* 269:25856-64; Thompson et al. (1995) supra), all incorporated by reference in their entireties. Designing and testing ribozymes for efficient cleavage of a target RNA is a process well known to those skilled in the art. Examples of scientific methods for designing and testing ribozymes are described by Chowrira et al., (1994) supra and Lieber and Strauss (1995) *Mol Cell Biol.* 15: 540-51, each incorporated by reference. The identification of operative and preferred sequences for use in down regulating a given gene is a matter of preparing and testing a given sequence, and is a routinely practiced "screening" method known to those of skill in the art. The use of RNAi constructs is described in literature cited above as well as in US2005/0166289 and WO 2013/016267 (both of which are incorporated herein by reference), for example. A double stranded RNA with homology to the target gene is delivered to the cell or produced in the cell by expression of an RNAi construct, for example, an RNAi short hairpin (sh) construct. The construct can include a sequence that is identical to the target gene, or at least about 50%, at least 55%, at least 60%, at least 65%, at least 70%, at least 75%, at least 80%, at least 85%, at least 90%, at least 95%, at least 96%, at least 97%, at least 98%, or at least about 99% identical to a sequence of the target gene. The construct can have at least about 20, at least 30, at least 40, at least 50, at least 100, at least 200, at least 300, at least 400, at least 500, at least 600, at least 700, at least 800, at least 900, or at least about 1 kb of sequence homologous to the target gene. Expression vectors can be engineered using promoters selected for continuous or inducible expression of an RNAi construct, such as a construct that produces an shRNA.

A nucleic acid construct for gene attenuation, e.g., a ribozyme, RNAi, or antisense construct can include at least about fifteen, at least twenty, at least thirty, at least forty, at least fifty, or at least sixty nucleotides having at least about 80% identity, such as at least 85%, at least 90%, at least 95%, or at least about 99% identity or complementarity to at least about a portion of the sequence of an endogenous lipid regulator gene of the microorganism to be engineered. A nucleic acid construct for gene attenuation, e.g., a ribozyme, RNAi, or antisense construct can include at least about fifteen, at least twenty, at least thirty, at least forty, at least fifty, or at least sixty nucleotides having at least about 80%, such as at least about 95% or about 100% identity or complementarity to the sequence of a naturally-occurring gene, such as a gene having encoding a polypeptide having at least about 50%, at least 55%, at least 60%, at least 65%, at least 70%, at least 75%, at least 80% or at least 85%, at least 90%, or at least about 95% sequence identity to an endogenous lipid regulator gene, such as a gene localized to the Naga_100020g79 locus (SEQ ID NO:3) or a gene that encodes a polypeptide having a GAF domain, such as for example GAF2 (e.g., SEQ ID NO 1). For example, a nucleic acid construct for gene attenuation, e.g., a ribozyme, RNAi, or antisense construct can include at least about fifteen, at least twenty, at least thirty, at least forty, at least fifty, or at least sixty nucleotides having at least about 80% identity or complementarity to the sequence of a naturally-occurring lipid regulator gene, such as any provided herein. The nucleotide sequence can be, for example, from at least about 30 nucleotides to at least about 3 kilobases, for example, from at least about 30 nucleotides to at least about 50 nucleotides in length, from at least about 50 nucleotides to at least about 100 nucleotides in length, from at least about 100 nucleotides to at least about 500 nucleotides in length, from at least about 500 nucleotides to at least about 1 kb in length, from at least about 1 kb to at least about 2 kb in length, or from at least about 2 kb to at least about 5 kb in length. For example, an antisense sequence can be from at least about 100 nucleotides to at least about 1 kb in length. For example, a nucleic acid construct for gene attenuation, e.g., a ribozyme, RNAi, or antisense construct can include at least about fifteen, at least twenty, at least thirty, at least forty, at least fifty, at least sixty, or at least about 100 nucleotides having at least about 50%, at least 55%, at least 60%, at least 65%, at least 70%, at least 75%, at least 80%, or at least 85%, for example at least 86%, at least 87%, at least 88%, at least 89%, at least 90%, at least 91%, at least 92%, at least 93%, at least 94%, or at least about 95% identity or complementarity to an endogenous lipid regulator gene or a portion thereof.

Promoters used in antisense, RNAi, or ribozyme constructs can be any that are functional in the host organism and that are suitable for the levels of expression required for reducing expression of the target gene to a desired amount. Promoters functional in algae and heterokonts are known in the art and disclosed herein. The construct can be transformed into algae using any feasible method, include any disclosed herein. A recombinant organism or microorganism transformed with a nucleic acid molecule for attenuating lipid regulator gene expression, such as but not limited to an antisense, RNAi, or ribozyme construct, can have the properties of a lipid regulator mutant as described herein, including, for example, reduced chlorophyll, increased photosynthetic efficiency, and increased productivity in culture, with respect to a host organism or microorganism that does not include the exogenous nucleic acid molecule that results in attenuated gene expression.

Nucleic Acid Molecules and Constructs

Also provided herein are nucleic acid molecules encoding polypeptides that include amino acid sequences having at least about 50%, at least 55%, at least 60%, at least 65%, at least 70%, at least 75%, at least 80%, at least 85%, at least 90%, at least 95%, at least 96%, at least 97%, at least 98%, or at least about 99% identity to SEQ ID NO:2. Alternatively or in addition, a nucleic acid molecule as provided herein can include a sequence having at least about 50%, at least 55%, at least 60%, at least 65%, at least 70%, at least 75%, at least 80%, at least 85%, at least 90%, at least 95%, at least 96%, at least 97%, at least 98%, or at least about 99% to an amino acid sequence of SEQ ID NO:2, and/or encoded by a nucleotide sequence having at least about 50%, at least 55%, at least 60%, at least 65%, at least 70%, at least 75%, at least 80%, at least 85%, at least 90%, at least 95%, at least 96%, at least 97%, at least 98%, or at least about 99% identity to SEQ ID NO:3 can include an amino acid sequence encoding a GAF domain, e.g., a GAF2 domain belonging to pfam PF13185. For example, the polypeptide encoded by the nucleic acid molecule can include a GAF domain having an amino acid sequence with at least about 50%, at least 55%, at least 60%, at least 65%, at least 70%, at least 75%, at least 80%, at least 85%, at least 90%, at least 95%, at least 96%, at least 97%, at least 98%, or at least about 99% identity to SEQ ID NO:4.

The nucleic acid molecule in various examples can be or comprise a cDNA that lacks one or more introns present in the naturally-occurring gene, or, alternatively, can include one or more introns not present in the naturally-occurring gene. The nucleic acid molecule in various examples can have a sequence that is not 100% identical to a naturally-occurring gene. For example, the nucleic acid molecule can include a mutation with respect to a naturally-occurring gene that reduces the activity of the encoded polypeptide or reduces expression of the mRNA or protein encoded by the gene.

The nucleic acid molecule in various examples can comprise a heterologous promoter operably linked to the sequence encoding a polypeptide that includes an amino acid sequence having at least about 50%, at least 55%, at least 60%, at least 65%, at least 70%, at least 75%, at least 80%, at least 85%, at least 90%, at least 95%, at least 96%, at least 97%, at least 98%, or at least about 99% identity to SEQ ID NO:1 or SEQ ID NO:2 and/or a sequence having at least about 50%, at least 55%, at least 60%, at least 65%, at least 70%, at least 75%, at least 80%, at least 85%, at least 90%, at least 95%, at least 96%, at least 97%, at least 98%, or at least about 99% identity to SEQ ID NO:3 or SEQ ID NO:4. Alternatively or in addition, a nucleic acid molecule can comprise a vector that includes a sequence encoding a polypeptide that includes an amino acid sequence having at least about 50%, at least 55%, at least 60%, at least 65%, at least 70%, at least 75%, at least 80%, at least 85%, at least 90%, at least 95%, at least 96%, at least 97%, at least 98%, or at least about 99% identity to SEQ ID NO:1 or SEQ ID NO:2; and/or a sequence that has at least about 50%, at least 55%, at least 60%, at least 65%, at least 70%, at least 75%, at least 80%, at least 85%, at least 90%, at least 95%, at least 96%, at least 97%, at least 98%, or at least about 99% identity to SEQ ID NO:3 or SEQ ID NO:4.

This disclosure also provides constructs designed for attenuating expression of a gene encoding a GAF domain, such as for example the GAF2 domain. The construct can be or comprise, in various examples, a sequence encoding a guide RNA of a CRISPR system, an RNAi construct, an antisense construct, a ribozyme construct, or a construct for homologous recombination, e.g., a construct having one or more nucleotide sequences having homology to a naturally-occurring GAF (e.g., GAF2) domain-encoding gene as disclosed herein and/or sequences adjacent thereto in the native genome from which the gene is derived. For example, the construct can include at least a portion of a gene encoding a polypeptide having a GAF domain, e.g., a sequence homologous to at least a portion of an gene that encodes a polypeptide that includes an amino acid sequence having at least about 50%, at least 55%, at least 60%, at least 65%, at least 70%, at least 75%, at least 80%, at least 85%, at least 90%, at least 95%, at least 96%, at least 97%, at least 98%, or at least about 99% identity to SEQ ID NO:1 or SEQ ID NO:2.

The construct for gene attenuation can include, for example, at least a portion of the coding region, intron, 5'UTR, promoter region, or 3' UTR of a gene encoding a polypeptide having a GAF domain, such as for example GAF2, or a polypeptide having at least about 50%, at least 55%, at least 60%, at least 65%, at least 70%, at least 75%, at least 80%, at least 85%, at least 90%, at least 95%, at least 96%, at least 97%, at least 98%, or at least about 99% identity to SEQ ID NO:2, or at least a portion of a gene having at least about 50%, at least 55%, at least 60%, at least 65%, at least 70%, at least 75%, at least 80%, at least 85%, at least 90%, at least 95%, at least 96%, at least 97%, at least 98%, or at least about 99% identity to SEQ ID NO:3, in either sense or antisense orientation.

In further examples a construct can be designed for the in vitro or in vivo expression of a guide RNA (e.g., of a CRISPR system) designed to target a naturally-occurring gene having a sequence having at least about 50%, at least 55%, at least 60%, at least 65%, at least 70%, at least 75%, at least 80%, at least 85%, at least 90%, at least 95%, at least 96%, at least 97%, at least 98%, or at least about 99% identity to at least a portion of SEQ ID NO:3, and/or encoding a polypeptide having a GAF domain, such as for example GAF2, comprising an amino acid sequence having at least about 50%, at least 55%, at least 60%, at least 65%, at least 70%, at least 75%, at least 80%, at least 85%, at least 90%, at least 95%, at least 96%, at least 97%, at least 98%, or at least about 99% identity to SEQ ID NO:1 or SEQ ID NO:2, and/or can include a sequence homologous to a portion of a gene encoding a polypeptide having a GAF domain (e.g., GAF2), including, for example, an intron, a 5'UTR, a promoter region, and/or a 3' UTR.

In yet further examples, a construct for attenuating expression of a gene encoding a GAF domain-containing polypeptide can be a guide RNA or antisense oligonucleotide, where the sequence having homology to a transcribed region of a gene encoding a polypeptide having a GAF domain in antisense orientation.

Nucleic acid constructs for attenuating expression of a GAF domain-encoding gene or a gene encoding a polypeptide having at least about 50%, at least 55%, at least 60%, at least 65%, at least 70%, at least 75%, at least 80%, at least 85%, at least 90%, at least 95%, at least 96%, at least 97%, at least 98%, or at least about 99% identity to SEQ ID NO:2 can include, for example at least about 17, at least 18, at least 19, at least 20, at least 21, at least 22, at least 23, at least 24, or at least about 25 nucleotides of sequence of a naturally occurring GAF domain-encoding gene and/or a gene encoding a polypeptide having at least about 50%, at least 55%, at least 60%, at least 65%, at least 70%, at least 75%, at least 80%, at least 85%, at least 90%, at least 95%, at least 96%, at least 97%, at least 98%, or at least about 99% identity to SEQ ID NO:2 and/or a gene having at least about 50%, at least 55%, at least 60%, at least 65%, at least 70%, at least 75%, at least 80%, at least 85%, at least 90%, at least 95%, at least 96%, at least 97%, at least 98%, or at least about 99% identity to a portion of SEQ ID NO:3.

In one example, provided herein is a nucleic acid molecule having at least about 50%, at least about 55%, at least about 60%, at least about 65%, at least about 70%, or at least about 75%, at least about 80%, at least about 85%, at least about 90%, or at least about 95% (e.g., at least any of 50%, 70%, 90% or 95%) identity to at least a portion of SEQ ID NO:3 or SEQ ID NO:4, where the nucleic acid molecule encodes a guide RNA of a CRISPR system. The nucleic acid molecule can include, for example at least about 17, at least about 18, at least about 19, at least about 20, at least about 21, at least about 22, at least about 23, at least about 24, or at least about 25 nucleotides (e.g., at least any of 17-25 nucleotides) of sequence of a naturally occurring GAF domain containing gene, such as but not limited to SEQ ID NO:3.

In addition, provided herein are antisense, ribozyme, or RNAi constructs that include at least a portion of a gene having a GAF domain (e.g., GAF2) or a polypeptide having at least about 65% identity to SEQ ID NO:2 and/or a gene having at least about 50%, at least 55%, at least 60%, at least 65%, at least 70%, at least 75%, at least 80%, at least 85%, at least 90%, at least 95%, at least 96%, at least 97%, at least 98%, or at least about 99% identity to a portion of SEQ ID NO:3, in which a promoter, such as a heterologous promoter, is operably linked to the GAF domain gene sequence and the GAF domain gene sequence is in antisense orientation.

Further, provided herein are constructs for homologous recombination that include a nucleotide sequence from or adjacent to a naturally-occurring algal gene encoding a polypeptide having an amino acid sequence with at least about 50%, at least 55%, at least 60%, at least 65%, at least 70%, at least 75%, at least 80%, at least 85%, at least 90%, at least 95%, at least 96%, at least 97%, at least 98%, or at least about 99% identity to SEQ ID NO:1 or SEQ ID NO:2; a gene localized to the Naga_100020g79 locus; and/or a gene that comprises an ORF comprising a sequence having at least about 50%, at least 55%, at least 60%, at least 65%, at least 70%, at least 75%, at least 80%, at least 85%, at least 90%, at least 95%, at least 96%, at least 97%, at least 98%, or at least about 99% identity to SEQ ID NO:3 and/or SEQ ID NO:4. In some embodiments, the nucleotide sequence is juxtaposed with a heterologous nucleic acid sequence that can be, in nonlimiting examples, a selectable marker or detectable marker gene. In some examples a construct for homologous recombination includes two nucleic acid sequences from or adjacent to a naturally-occurring algal gene encoding a polypeptide having an amino acid sequence with at least about 50%, at least 55%, at least 60%, at least 65%, at least 70%, at least 75%, at least 80%, at least 85%, at least 90%, at least 95%, at least 96%, at least 97%, at least 98%, or at least 99% identity to SEQ ID NO:1 or SEQ ID NO:2; a gene localized to the Naga_100020g79 locus; and/or a gene that comprises an ORF comprising a sequence having at least about 50%, at least 55%, at least 60%, at least 65%, at least 70%, at least 75%, at least 80%, at least 85%, at least 90%, at least 95%, at least 96%, at least 97%, at least 98%, or at least about 99% identity to SEQ ID NO:3 and/or SEQ ID NO:4, where the two sequences flank a heterologous sequence for insertion into the gene locus.

One skilled in the art will appreciate that a number of transformation methods can be used for genetic transformation of microorganisms and, therefore, can be deployed for the methods of the present invention. "Stable transformation" is intended to mean that the nucleic acid construct introduced into an organism integrates into the genome of the organism or is part of a stable episomal construct and is capable of being inherited by the progeny thereof. "Transient transformation" is intended to mean that a polynucleotide is introduced into the organism and does not integrate into the genome or otherwise become established and stably inherited by successive generations.

Genetic transformation can result in stable insertion and/or expression of transgenes, constructs from either the nucleus or the plastid, and in some cases can result in transient expression of transgenes. The transformation methods can also be used for the introduction of guide RNAs or editing DNAs. Genetic transformation of microalgae has been reported successful for more than 30 different strains of microalgae, which belong to at least ~22 species of green, red, and brown algae, diatoms, euglenids, and dianoflagellates (see, e.g., Radakovits et al., *Eukaryotic Cell,* 2010; and Gong et al., *J. Ind. Microbiol. Biotechnol.,* 2011). Non-limiting examples of such useful transformation methods include agitation of cells in the presence of glass beads or silicon carbide whiskers as reported by, for example, Dunahay, *Biotechniques,* 15(3):452-460, 1993; Kindle, *Proc. Natl. Acad. Sci. U.S.A.,* 1990; Michael and Miller, *Plant J.,* 13, 427-435, 1998. Electroporation techniques have been successfully used for genetic transformation of several microalgal species including *Nannochloropsis* sp. (see, e.g., Chen et al., *J. Phycol.,* 44:768-76, 2008), *Chlorella* sp. (see, e.g., Chen et al., *Curr. Genet.,* 39:365-370, 2001; Chow and Tung, *Plant Cell Rep.* Vol. 18, No. 9, 778-780, 1999), *Chlamydomonas* (Shimogawara et al., Genetics, 148: 1821-1828, 1998), *Dunaliella* (Sun et al., *Mol. Biotechnol.,* 30(3): 185-192, 2005). Micro-projectile bombardment, also referred to as microparticle bombardment, gene gun transformation, or biolistic bombardment, has been used successfully for several algal species including, for example, diatoms species such as *Phaeodactylum* (Apt et al., *Mol. Gen. Genet.,* 252:572-579, 1996), Cyclotella and Navicula (Dunahay et al., *J. Phycol.,* 31:1004-1012, 1995), Cylindrotheca (Fischer et al., *J. Phycol.,* 35:113-120, 1999), and *Chaetoceros* sp. (Miyagawa-Yamaguchi et al., *Phycol. Res.* 59: 113-119, 2011), as well as green algal species such as *Chlorella* (El-Sheekh, *Biologia Plantarum*, Vol. 42, No. 2: 209-216, 1999), and *Volvox* species (Jakobiak et al., Protist, 155:381-93, 2004). Additionally, *Agrobacterium*-mediated gene transfer techniques can also be useful for genetic transformation of microalgae, as has been reported by, for example, Kumar, *Plant Sci.,* 166(3):731-738, 2004, and Cheney et al., *J. Phycol.,* Vol. 37, Suppl. 11, 2001.

A transformation vector or construct as described herein will typically comprise a marker gene that confers a selectable or scorable phenotype on target host cells, e.g., algal cells or may be co-transformed with a construct that includes a marker. A number of selectable markers have been successfully developed for efficient isolation of genetic transformants of algae. Common selectable markers include antibiotic resistance, fluorescent markers, and biochemical markers. Several different antibiotic resistance genes have been used successfully for selection of microalgal transformants, including blastocidin, bleomycin (see, for example, Apt et al., 1996, supra; Fischer et al., 1999, supra; Fuhrmann et al., *Plant J.,* 19, 353-61, 1999, Lumbreras et al., *Plant J.,* 14(4):441-447, 1998; Zaslavskaia et al., *J. Phycol.,* 36:379-386, 2000), spectinomycin (Cerutti et al., *Genetics,* 145: 97-110, 1997; Doetsch et al., *Curr. Genet.,* 39, 49-60, 2001; Fargo, *Mol. Cell. Biol.,* 19:6980-90, 1999), streptomycin (Berthold et al., *Protist,* 153:401-412, 2002), paromomycin (Jakobiak et al., *Protist*, supra.; Sizova et al., *Gene,* 277: 221-229, 2001), nourseothricin (Zaslavskaia et al., 2000, supra), G418 (Dunahay et al., 1995, supra; Poulsen and Kroger, FEBS Lett., 272:3413-3423, 2005, Zaslavskaia et al., 2000, supra), hygromycin (Berthold et al., 2002, supra), chloramphenicol (Poulsen and Kroger, 2005, supra), and many others. Additional selectable markers for use in microalgae such as *Chlamydomonas* can be markers that provide resistance to kanamycin and amikacin resistance (Bateman, *Mol. Gen. Genet.* 263:404-10, 2000), zeomycin and phleomycin (e.g., ZEOCIN™ pheomycin D1) resistance (Stevens, *Mol. Gen. Genet.* 251:23-30, 1996), and paromomycin and neomycin resistance (Sizova et al., 2001, supra). Other fluorescent or chromogenic markers that have been used include luciferase (Falciatore et al., *J. Mar. Biotechnol.,* 1: 239-251, 1999; Fuhrmann et al., *Plant Mol. Biol.,* 2004; Jarvis and Brown, *Curr. Genet.,* 19: 317-322, 1991), β-glucuronidase (Chen et al., 2001, supra; Cheney et al., 2001, supra; Chow and Tung, 1999, supra; El-Sheekh, 1999, supra; Falciatore et al., 1999, supra; Kubler et al., *J. Mar. Biotechnol.,* 1:165-169, 1994), β-galactosidase (Gan et al., *J. Appl. Phycol.,* 15:345-349, 2003; Jiang et al., *Plant Cell Rep.,* 21:1211-1216, 2003; Qin et al., *High Technol. Lett.,* 13:87-89, 2003), and green fluorescent protein (GFP) (Cheney et al., 2001, supra; Ender et al., *Plant Cell,* 2002, Franklin et al., *Plant J.,* 2002; 56, 148, 210).

One skilled in the art will readily appreciate that a variety of known promoter sequences can be usefully deployed for transformation systems of microalgal species in accordance with the present invention. For example, the promoters commonly used to drive transgene expression in microalgae include various versions of the of cauliflower mosaic virus promoter 35S (CaMV35S), which has been used in both dinoflagellates and chlorophyta (Chow et al, *Plant Cell Rep.,* 18:778-780, 1999; Jarvis and Brown, *Curr. Genet.,* 317-321, 1991; Lohuis and Miller, *Plant J.,* 13:427-435, 1998). The SV40 promoter from simian virus has also reported to be active in several algae (Gan et al., *J. Appl. Phycol.,* 151 345-349, 2003; Qin et al., *Hydrobiologia* 398-399, 469-472, 1999). The promoters of RBCS2 (ribulose bisphosphate carboxylase, small subunit) (Fuhrmann et al., *Plant J.,* 19:353-361, 1999) and PsaD (abundant protein of photosystem I complex; Fischer and Rochaix, *FEBS Lett.* 581:5555-5560, 2001) from *Chlamydomonas* can also be useful. The fusion promoters of HSP70A/RBCS2 and HSP70A/02TUB (tubulin) (Schroda et al., *Plant J.,* 21:121-131, 2000) can also be useful for an improved expression of transgenes, in which HSP70A promoter may serve as a transcriptional activator when placed upstream of other promoters. High-level expression of a gene of interest can also be achieved in, for example diatoms species, under the control of a promoter of an fcp gene encoding a diatom fucoxanthin-chlorophyll a/b binding protein (Falciatore et al., *Mar. Biotechnol.,* 1:239-251, 1999; Zaslavskaia et al., *J. Phycol.* 36:379-386, 2000) or the vcp gene encoding a eustigmatophyte violaxanthin-chlorophyll a/b binding protein (see U.S. Pat. No. 8,318,482, incorporated by reference herein). If so desired, inducible promoters can provide rapid and tightly controlled expression of genes in transgenic microalgae. For example, promoter regions of the NR genes encoding nitrate reductase can be used as such inducible promoters. The NR promoter activity is typically suppressed by ammonium and induced when ammonium is replaced by nitrate (Poulsen and Kroger, *FEBS Lett* 272:3413-3423, 2005), thus gene expression can be switched off or on when microalgal cells are grown in the presence of ammonium/nitrate. Additional algal promoters that can find use in the constructs and transformation systems provided herein include those disclosed in U.S. Pat. No. 8,883,993; U.S. Patent Appl. Pub. No. US 2013/0023035; U.S. Patent Application Pub. No. US 2013/0323780; and U.S. Patent Application Pub. No. US 2014/0363892, all incorporated herein by reference in their entireties.

Host cells can be either untransformed cells or cells that are already transfected with at least one nucleic acid molecule. For example, an algal host cell that is engineered to have attenuated expression of a lipid regulator gene can further include one or more genes that may confer any desirable trait, such as, but not limited to, increased production of biomolecules of interest, such as one or more proteins, pigments, alcohols, or lipids.

Methods of Producing Lipids

Also provided herein are methods of producing lipid by culturing a mutant microorganism as provided herein that has increased lipid productivity with respect to a control cell when cultured under the same conditions. The methods include culturing a mutant microorganism as provided herein in a suitable medium to produce lipid and recovering biomass or at least one lipid from the culture. The microorganism can in some examples be an alga, and the culture can be a photoautotrophic culture. Culturing can be in batch, semi-continuous, or continuous mode.

The mutant microorganism in some examples can be cultured in a medium that comprises less than about 5 mM ammonium, less than about 4.5 mM ammonium, less than about 4 mM ammonium, less than about 3.5 mM ammonium, less than about 3 mM ammonium, less than about 2.5 mM ammonium, less than about 2 mM ammonium, less than about 1.5 mM ammonium, less than or equal to about 1 mM ammonium, less than or equal to about 0.5 mM (e.g., less than 5 mM), or substantially no ammonium. The culture medium can include, for example, from about 0 to about 5 mM ammonium, from about 0 to about 4.5 mM ammonium, from about 0 to about 4.0 mM ammonium, from about 0 to about 3.5 mM ammonium, from about 0 to about 3 mM ammonium, from about 0 to about 2.5 mM ammonium, from about 0 to about 2.0 mM ammonium, from about 0 to about 1.5 mM ammonium, from about 0 to about 1.0 mM ammonium, from about 0 to about 0.5 mM ammonium, from about 0.2 to about 3 mM ammonium, from about 0.2 to about 2.5 mM ammonium, from about 0.2 to about 2 mM ammonium, from about 0.2 to about 1.5 mM ammonium, from about 0.2 to about 1 mM ammonium, from about 0.3 to about 2.5 mM ammonium, from about 0.3 to about 2 mM ammonium, from about 0.3 to about 1.5 mM ammonium, from about 0.3 to about 1 mM ammonium, from about 0.4 to about 2.5 mM ammonium, from about 0.4 to about 2 mM ammonium, or from about 0.4 to about 1.5 mM (e.g., 0-5 mM) ammonium. The microorganism can be cultured in a medium that includes nitrate, which in some examples may be substantially the sole nitrogen source in the culture medium or may be present in addition to less than about 5 mM ammonium, less than about 4.5 mM ammonium, less than about 4 mM ammonium, less than about 3.5 mM ammonium, less than about 3 mM ammonium, less than about 2.5 mM ammonium, less than about 2 mM ammonium, less than about 1.5 mM ammonium, less than or equal to about 1 mM ammonium, less than or equal to about 0.5 mM (e.g., less than 5 mM), or substantially no ammonium. Alternatively or in addition, the culture medium can comprises urea, which in some examples can be substantially the sole source of nitrogen in the culture medium.

The lipid producing microorganisms may be cultured in any suitable vessel(s), including flasks or bioreactors. In some examples, the mutant microorganism is an alga and is exposed to light for at least a portion of the culture period, in which the algae may be exposed to artificial or natural light (or natural light supplemented with artificial light). The culture comprising mutant algae that are deregulated in their response to low light may be cultured on a light/dark cycle that may be, for example, a natural or programmed light/dark cycle, and as illustrative examples, may provide twelve hours of light to twelve hours of darkness, fourteen hours of light to ten hours of darkness, sixteen hours of light to eight hours of darkness, etc. Alternatively, an algal mutant can be cultured in continuous light.

Culturing refers to the intentional fostering of growth (e.g., increases in cell size, cellular contents, and/or cellular activity) and/or propagation (e.g., increases in cell numbers via mitosis) of one or more cells by use of selected and/or controlled conditions. The combination of both growth and propagation may be termed proliferation. A microorganism as provided herein may be cultured for at least about five, at least about six, at least about seven at least about eight, at least about nine, at least about ten, at least about eleven at least about twelve, at least about thirteen, at least about fourteen, or at least about fifteen days, or at least about one, two three, four, five, six, seven, eight, nine, or ten weeks, or longer. The culturing can be in a culture medium that is nutrient replete with respect to a control alga.

Non-limiting examples of selected and/or controlled conditions that can be used for culturing the recombinant microorganism can include the use of a defined medium (with known characteristics such as pH, ionic strength, and/or carbon source), specified temperature, oxygen tension, carbon dioxide levels, growth in a bioreactor, or the like, or combinations thereof. In some embodiments, the microorganism or host cell can be grown mixotrophically, using both light and a reduced carbon source. Alternatively, the microorganism or host cell can be cultured phototrophically. When growing phototrophically, the algal strain can advantageously use light as an energy source. An inorganic carbon source, such as $CO_2$ or bicarbonate can be used for synthesis of biomolecules by the microorganism. "Inorganic carbon", as used herein, includes carbon-containing compounds or molecules that cannot be used as a sustainable energy source by an organism. Typically "inorganic carbon" can be in the form of $CO_2$ (carbon dioxide), carbonic acid, bicarbonate salts, carbonate salts, hydrogen carbonate salts, or the like, or combinations thereof, which cannot be further oxidized for sustainable energy nor used as a source of reducing power by organisms. A microorganism grown photoautotrophically can be grown on a culture medium in which inorganic carbon is substantially the sole source of carbon. For example, in a culture in which inorganic carbon is substantially the sole source of carbon, any organic (reduced) carbon molecule or organic carbon compound that may be provided in the culture medium either cannot be taken up and/or metabolized by the cell for energy and/or is not present in an amount sufficient to provide sustainable energy for the growth and proliferation of the cell culture.

Microorganisms and host cells that can be useful in accordance with the methods of the present invention can be found in various locations and environments throughout the world. The particular growth medium for optimal propagation and generation of lipid and/or other products can vary and may be optimized to promote growth, propagation, or production of a product such as a lipid, protein, pigment, antioxidant, etc. In some cases, certain strains of microorganisms may be unable to grow in a particular growth medium because of the presence of some inhibitory component or the absence of some essential nutritional requirement of the particular strain of microorganism or host cell.

Solid and liquid growth media are generally available from a wide variety of sources, as are instructions for the preparation of particular media suitable for a wide variety of strains of microorganisms. For example, various fresh water and salt water media can include those described in Barsanti (2005) Algae: Anatomy, Biochemistry & Biotechnology, CRC Press for media and methods for culturing algae. Algal media recipes can also be found at the websites of various algal culture collections, including, as nonlimiting examples, the UTEX Culture Collection of Algae; Culture Collection of Algae and Protozoa; and Katedra Botaniky.

The culture methods can optionally include inducing expression of one or more genes and/or regulating a metabolic pathway in the microorganism. Inducing expression can include adding a nutrient or compound to the culture, removing one or more components from the culture medium, increasing or decreasing light and/or temperature, and/or other manipulations that promote expression of the gene of interest. Such manipulations can largely depend on the nature of the (heterologous) promoter operably linked to the gene of interest.

In some embodiments of the present invention, the microorganisms having increased lipid productivity can be cultured in a photobioreactor equipped with an artificial light source, and/or having one or more walls that is transparent enough to light, including sunlight, to enable, facilitate, and/or maintain acceptable microorganism growth and proliferation. For production of fatty acid products or triglycerides, photosynthetic microorganisms or host cells can additionally or alternately be cultured in shake flasks, test tubes, vials, microtiter dishes, petri dishes, or the like, or combinations thereof.

Additionally or alternately, mutant or recombinant photosynthetic microorganisms or host cells may be grown in ponds, canals, sea-based growth containers, trenches, raceways, channels, or the like, or combinations thereof. In such systems, the temperature may be unregulated, or various heating or cooling method or devices may be employed As with standard bioreactors, a source of inorganic carbon (such as, but not limited to, $CO_2$, bicarbonate, carbonate salts, and the like), including, but not limited to, air, $CO_2$-enriched air, flue gas, or the like, or combinations thereof, can be supplied to the culture. When supplying flue gas and/or other sources of inorganic that may contain CO in addition to $CO_2$, it may be necessary to pre-treat such sources such that the CO level introduced into the (photo)bioreactor do not constitute a dangerous and/or lethal dose with respect to the growth, proliferation, and/or survival of the microorganisms.

The mutant microorganisms can optionally include one or more non-native genes encoding a polypeptide for the production of a product, such as but not limited to a lipid.

The methods include culturing a mutant microorganism as provided herein, such as a mutant microorganism as provided herein that has increased lipid productivity with respect to a control cell when cultured under the same conditions to produce biomass or lipid. Lipids can be recovered from culture by recovery means known to those of ordinary skill in the art, such as by whole culture extraction, for example, using organic solvents or by first isolating biomass from which lipids are extracted (see, for example, Hussein et al. Appl. Biochem. Biotechnol. 175:3048-3057; Grima et al. (2003) Biotechnol. Advances 20:491-515). In some cases, recovery of fatty acid products can be enhanced by homogenization of the cells (Gunerken et al. (2015) Biotechnol. Advances 33:243-260). For example, lipids such as fatty acids, fatty acid derivatives, and/or triglycerides can be isolated from algae by extraction of the algae with a solvent at elevated temperature and/or pressure, as described in the co-pending, commonly-assigned U.S. patent publication No. US 2013/0225846 entitled "Solvent Extraction of Products from Algae", filed on Feb. 29, 2012, which is incorporated herein by reference in its entirety. Biomass can be harvested, for example, by centrifugation or filtering. The biomass may be dried and/or frozen. Further products may be isolated from biomass, such as, for example, various lipids or one or more proteins. Also included in the invention is an algal biomass comprising biomass of lipid regulator mutant, such as any disclosed herein, such as but not limited to a lipid regulator mutant that includes a mutation in a gene encoding a polypeptide that has a GAF (e.g., GAF2) domain having at least about 50%, at least about 55%, at least 60%, at least 65%, at least 70%, at least 75%, at least 80%, at least 85%, at least 90%, at least 95%, at least 96%, at least 97%, at least 98%, or at least about 99% identity to SEQ ID NO:1 or a mutation in a gene encoding a polypeptide having at least about 50%, at least 55%, at least 60%, at least 65%, at least 70%, at least 75%, at least 80%, at least 85%, at least 90%, at least 95%, at least 96%, at least 97%, at least 98%, or at least about 99% identity to SEQ ID NO:1.

Also considered are cell extracts, including crude cell lysates or cell lysates from which one or more components has been separated. One or more separation steps such as, but not limited to, centriguation, precipitation, filtration, or chromatography can optionally be used to produce the extract. In various nonlimiting examples, a cell lysate can be decanted, filtered, or removed from sedimented solid, particulate, membranous, or aggregated cellular material to produce the extract A cell extract can alternatively or in addition optionally be the product of an extraction that uses one or more detergents, surfactants, or solvents which may also be present in the extract. The extract can optionally include one or more salts, buffers, stabilizers, or antioxidants.

Other embodiments are also contemplated herein, as would be understood by one of ordinary skill in the art. Certain embodiments are further described in the following examples. These embodiments are provided as examples only and are not intended to limit the scope of the claims in any way.

All references cited herein are incorporated by reference in their entireties. All headings are for the convenience of the reader and do not limit the invention in any way. References to aspects or embodiments of the invention do not necessarily indicate that the described aspects may not be combined with other described aspects of the invention or features of other aspects of the invention.

EXAMPLES

Media Used in Examples

PM074 is a nitrogen replete ("nitrate-only") medium that is 10×F/2 made by adding 1.3 ml PROLINE® F/2 Algae Feed Part A (Aquatic Eco-Systems) and 1.3 ml PROLINE® F/2 Algae Feed Part B (Aquatic Eco-Systems) to a final volume of 1 liter of a solution of Instant Ocean salts (35 g/L) (Aquatic Eco Systems, Apopka, Fla.). Proline A and Proline B together include 8.8 mM $NaNO_3$, 0.361 mM $NaH_2PO_4.H_2O$, 10×F/2 Trace metals, and 10×F/2 Vitamins (Guillard (1975) Culture of phytoplankton for feeding marine invertebrates. in "Culture of Marine Invertebrate Animals." (eds: Smith W. L. and Chanley M. H.) Plenum Press, New York, USA. pp 26-60).

PM124 medium is PM074 supplemented with 5 mM Ammonium and 10 mM HEPES pH 8.0. It is made by adding 10 mls of 1 M HEPES pH 8 and 5 mls of $NH_4Cl$ to the PM074 recipe (final volume of 1 L). Additional media with controlled ammonium levels was made by adjusting the ammonium concentration of PM074 and adding additional Hepes buffer.

PM074 and PM124 media are nitrogen replete and nutrient replete with respect to wild type Nannochloropsis.

Example 1

Identification of a GAF-Domain Containing Polypeptide that Influences Lipid Biosynthesis Transgenic algal strains of Nannochloropsis gaditana were created in which a gene localized to the Naga_100020g79 locus, which encodes a protein containing a conserved domain of unknown function and a GAF2 domain (Pfam ID: PF13185; represented by SEQ ID NO:1) found in signal transductions proteins, was functionally ablated or knocked out in a wild-type N. gaditana strain (designated WT-3730) by targeted mutagenesis using CRISPR technology. The nucleotide sequence of the coding region of the N. gaditana gene at the Naga_100020g79 locus is provided as SEQ ID NO:3 and SEQ ID NO:2 represents the amino acid sequence of the encoded protein. The gene was named the STP-4551 gene. The amino acid sequence of the GAF2 domain of STP-4551 is provided as SEQ ID NO: 1.

To produce the knock-out mutants, a high efficiency Nannochloropsis Cas9 Editor line (N. gaditana strain GE-6791) was developed essentially as disclosed in co-pending application US 2017/0073695 "Compositions and Methods for High Efficiency In Vivo Genome Editing". Strain GE-6791, which expresses a gene encoding the Streptococcus pyogenes Cas9 nuclease and also includes a blasticidin resistance gene and a green fluorescence protein gene (TurboGFP, Evrogen), was modified to remove the GFP gene by targeting it with a guide RNA. Transformation was by electroporation essentially as disclosed in U.S. patent application publication US 2014/0220638, incorporated herein by reference. The resulting strain, GE-13038, included a Cas9 gene and a blasticidin resistance gene, and was GFP⁻ (did not express GFP). The GE-13038 strain was used as a host for transformation with a chimeric guide RNA and donor DNA for insertional knockout. Accordingly, a Nannochloropsis strain was engineered and isolated that included a Cas9 expression cassette which contained a Cas9 gene from Streptococcus pyogenes codon optimized for N. gaditana (SEQ ID NO:5) that included sequences encoding an N-terminal nuclear localization signal (SEQ ID NO:6), followed by a FLAG tag (SEQ ID NO:7), and peptide linker (together provided as SEQ ID NO:8), driven by the N. gaditana RPL24 promoter (SEQ ID NO:9) and terminated by the N. gaditana bidirectional terminator 2 (SEQ ID NO:10) and a selectable marker expression cassette, which contained the blasticidin S deaminase gene from Aspergillus terreus codon optimized for N. gaditana (SEQ ID NO:11), driven by the N. gaditana TCTP promoter (SEQ ID NO:12) and followed by the EIF3 terminator (SEQ ID NO:13).

The STP-4551 gene localized to the Naga_100020g79 locus (ORF having sequence of SEQ ID NO:3; FIG. 1) was one of the genes targeted for disruption using Cas9-mediated genome editing. Briefly, a Hygromycin resistance expression cassette was targeted to insert into the gene, and a DNA construct was made (SGI-DNA, La Jolla, Calif.) for producing a guide RNA in which the DNA molecule included the sequence of a chimeric guide engineered downstream of a T7 promoter. The chimeric guide sequence included a 21 bp target sequence (SEQ ID NO:4) homologous to a sequence within the gene localized to the Naga_100020g79 locus located upstream of an S. pyogenes Cas9 PAM sequence (NGG), and also included the transactivating CRISPR RNA (tracr RNA) sequence. The chimeric guide sequence was synthesized by first making a DNA template made up of complementary DNA oligonucleotides (SEQ ID NO:14 and SEQ ID NO:15) that when annealed produced a double-stranded construct having the T7 promoter immediately upstream of the guide target sequence which was then followed by the tracr mate and tracr sequences. The two DNA oligonucleotides were annealed to create a double-stranded DNA template which was used in in vitro transcription reactions using the MEGAshortscript™ T7 Kit (Life Technologies, Carlsbad, Calif. # AM1354M) according to the manufacturer's instructions to synthesize the guide RNA. The resulting RNA was purified using Zymo-Spin™ V-E columns (Zymo Research #C1024-25) according to the manufacturer's protocol.

The donor fragment for insertion into the gene localized to the Naga_100020g79 locus included a selectable marker cassette that included the hygromycin resistance gene (HygR, SEQ ID NO:16) downstream of the N. gaditana EIF3 promoter (SEQ ID NO:17) and followed by N. gaditana bidirectional terminator 2 (SEQ ID NO:10), with the entire promoter-hygromycin resistance gene-terminator sequence flanked by 27 base pair identification sequences on the 5' (SEQ ID NO:18) and 3' (SEQ ID NO:19) ends to yield the DNA fragment referred to as the "Hyg Resistance Cassette" (SEQ ID NO:20).

For targeted knockout of the gene localized to the Naga_100020g79 locus, Cas9 Editor line GE-6791 was transformed by electroporation using 5 µg of purified chimeric guide RNA targeting the gene localized to the Naga_100020g79 locus and 1 µg of the selectable donor DNA (Hyg Resistance Cassette Naga_100020g79; SEQ ID NO:20) essentially as described in US 2014/0220638. Following electroporation, cells were plated on PM124 agar media containing hygromycin to select for transformants that incorporated the hygromycin resistance cassette. Transformants were patched onto a fresh plate and screened by colony PCR for insertion of the donor fragment into the gene localized to the Naga_100020g79 locus.

For colony PCR screening, a small amount of cells from a colony to be screened was suspended into 100 µl of 5% Chelex 100 Resin (BioRad)/TE solution and the suspension was boiled for 10 minutes at 99° C., after which the tubes were briefly spun. One microliter of the lysate supernatant was added to a PCR reaction mix, in which the PCR mixture and reactions were set up and performed according to the QIAGEN Fast Cycling PCR Master Mix Protocol from the manufacturer (handbook available on the Qiagen website). The primers used to detect the insertion of the donor fragment into the targeted locus (Naga_100020g79) were SEQ ID NO:21 and SEQ ID NO:22. The PCR-based colony screening identified two knockout strains of the STP-4551 gene localized to the Naga_100020g79 locus, GE-13535 and GE-13536.

Example 2

Naga_100020g79 Knockout Mutant in Batch Productivity Assay

The knockout mutant strains having disrupted genes encoding a GAF2 domain-containing polypeptide, GE-13535 and GE-13536, were assessed in a batch productivity assay in nitrogen replete medium PM074 that included 8.8 mM nitrate as the sole nitrogen source available to the cells in the absence of any reduced carbon source that could support algal growth (i.e., the productivity assay was conducted under photoautotrophic conditions). After inoculation, engineered knockout strains and wild type strain WT-3730 were grown in triplicate cultures in a batch assay in 75 cm$^2$ rectangular tissue culture flasks containing 175 ml of PM074 medium for seven days. Under these conditions, nitrogen begins to become limiting in the culture medium on approximately Day 3, with the concentration of nitrogen in the culture medium continuing to drop throughout the remainder of the assay. The flasks were positioned with their narrowest "width" dimension against an LED light. The culture flasks were masked with an opaque white plastic to provide a 21.1 cm$^2$ rectangular opening for irradiance to reach the cultures. Incident irradiance was programmed at a 16 h light:8-hour dark cycle where a linear ramp up of irradiance from 0 to 1200 uE and then a linear ramp down in irradiance from 1200 to 0 uE over a 4 h period. Deionized H$_2$O was added to the cultures daily to replace evaporative losses. The temperature of the cultures was regulated by a water bath set at 25° C. Cultures were inoculated at OD$_{730}$ of 0.5 on day 0 and samples (5 mls) were removed on days 3, 5, and 7 for assessing cell density, fatty acid methyl esters (FAME) as a measure of lipid, and total organic carbon (TOC). Sampling was done 30 minutes prior to the end of the light cycle.

In these assays, the carbon partitioning to lipid phenotype was assessed by measuring fatty acid methyl esters (FAMEs) to represent lipids and total organic carbon (TOC) to represent biomass; and the ratio of FAME/TOC was used to assess whether a strain had increased carbon partitioning to lipids versus the wild type 3730 strain.

FAME analysis was performed on 2 mL samples that were dried using a GeneVac HT-4X. To each of the dried pellets the following were added: 500 µL of 500 mM KOH in methanol, 200 µL of tetrahydrofuran containing 0.05% butylated hydroxyl toluene, 40 µL of a 2 mg/ml C11:0 free fatty acid/C13:0 triglyceride/C23:0 fatty acid methyl ester internal standard mix and 500 µL of glass beads (425-600 am diameter). The vials were capped with open top PTFE septa-lined caps and placed in an SPEX GenoGrinder at 1.65 krpm for 7.5 minutes. The samples were then heated at 80° C. for five minutes and allowed to cool. For derivatization, 500 µL of 10% boron trifluoride in methanol was added to the samples prior to heating at 80° C. for 30 minutes. The tubes were allowed to cool prior to adding 2 mL of heptane and 500 µL of 5 M NaCl. The samples were vortexed for five minutes at 2K rpm and finally centrifuged for three minutes at 1K rpm. The heptane layer was sampled using a Gerstel MPS Autosampler. Quantitation used the 80 µg of C23:0 FAME internal standard. The samples were run on an Agilent 7890A gas chromatography system using a J&W Scientific 127-3212 DB-FFAP, 10 m×100 µm×100 nm column and an FID detector at 260° C. The flow rate was 500 µL/minute using H$_2$ as a carrier with constant flow control. The oven was set at 100° C. for 0.98 min, then 15.301° C./minute to 230° C. and held for 1.66 min. The inlet contained a 4 mm glass wool packed liner (Agilent P/N 5183-4647), and was set at 250° C. and used a split ratio of 40:1. The injection volume was 900 nL. Total organic carbon (TOC) was determined by diluting 2 mL of cell culture to a total volume of 20 mL with DI water. Three injections per measurement were injected into a Shimadzu TOC-Vcsj Analyzer for determination of Total Carbon (TC) and Total Inorganic Carbon (TIC). The combustion furnace was set to 720° C., and TOC was determined by subtracting TIC from TC. The 4 point calibration range was from 2 ppm to 200 ppm corresponding to 20-2000 ppm for non-diluted cultures with a correlation coefficient of $r^2>0.999$.

Figure 2:
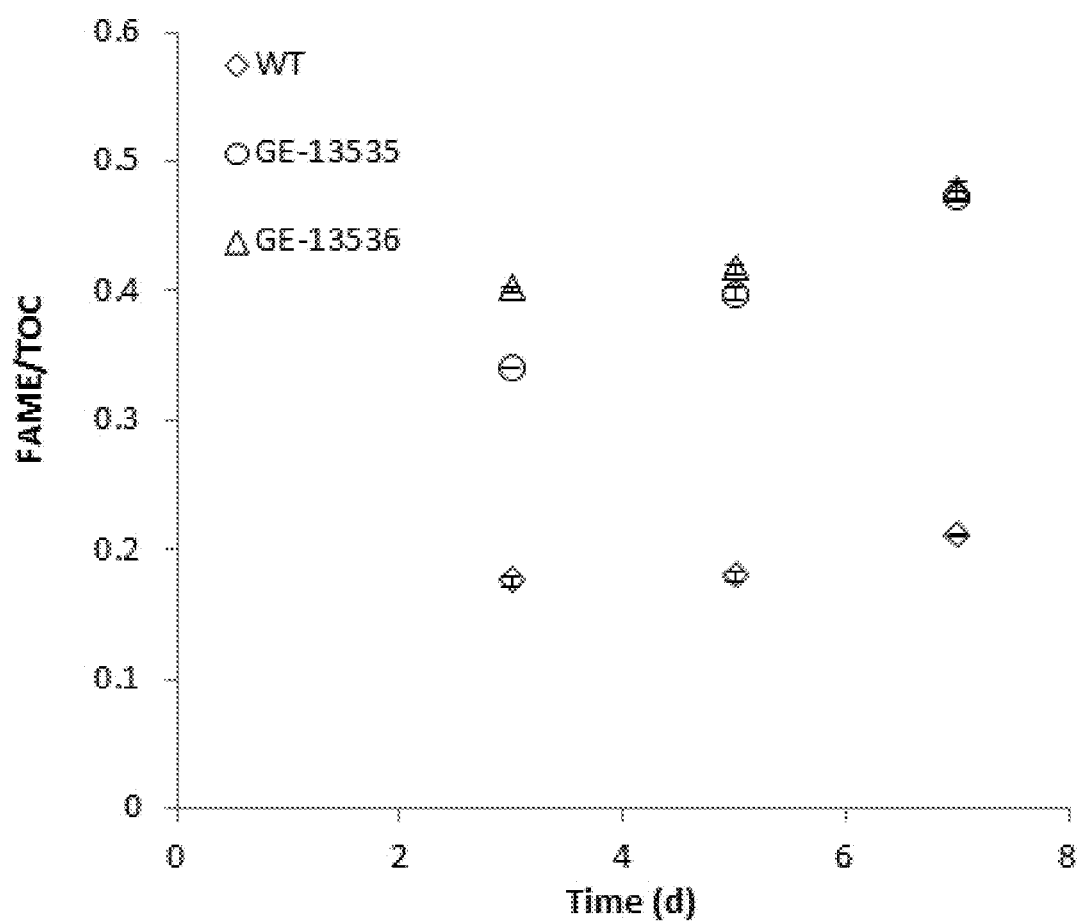
FIG. 2 is a graph showing FAME/TOC ratios of mutant strains GE-13535 and GE-13536 and wild type strain WT-3730 grown in batch culture using nitrate as the nitrogen source. Error bars represent standard deviations of two biological replicates. Symbols used in graphs: diamonds represent wild type WT-3730, circles represent knockout mutant GE-13535, and triangles represent knockout mutant GE-13536.
Figure 3:
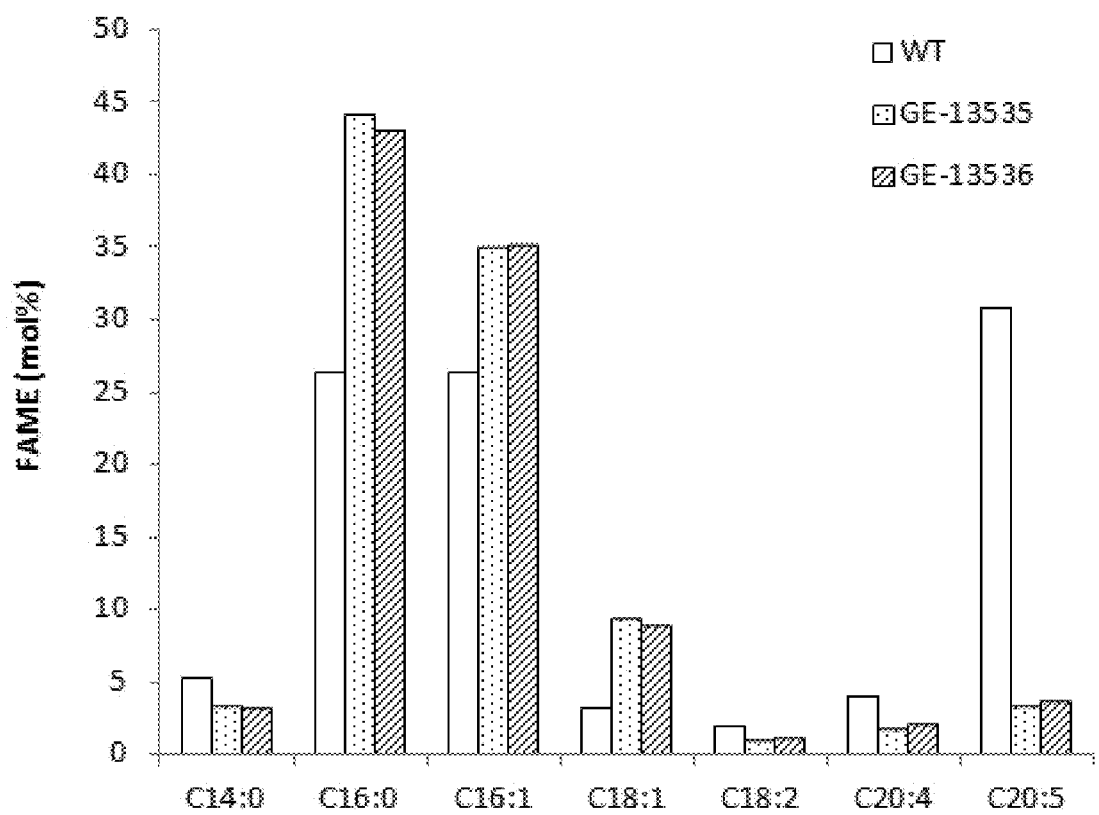
FIG. 3 is a bar graph depicting the amount of fatty acids of various chain lengths present in the lipids isolated on day 7 of the batch assay from wild type WT-3730 (no pattern) and knockout strains GE-13535 (dotted) and GE-13536 (slanted lines).

The results of the assays are provided in Tables 1 and 2 and FIGS. 2 and 3. Table 1 and FIG. 2 show the FAME/TOC ratios of wild type Nannochloropsis gaditana strain WT-3730 grown in a batch productivity assay in nitrogen replete medium PM074, which included 8.8 mM nitrate as the sole nitrogen source available to the cells, alongside the FAME/TOC ratios of mutant strains (GE-13535 and GE-13536) on days 3, 5 and 7 of the culture. Wild-type strains possessed FAME/TOC ratios close to 0.2 throughout the productivity run while FAME/TOC ratios of the mutants GE-13535 and GE-13536 hovered around 0.4, thus resulting in a 95-131% increase over wild type depending on the culture day. Table 2 and FIG. 3 show FAME profiles at day 5 of the run; the mutants possessed high levels of 16:0 and 16:1 fatty acids and low levels of EPA (20:5) compared to the wild-type strain.

TABLE 1

FAME/TOC ratios for wild-type and mutant strains

| Days | WT | s.d. | GE-13535 | s.d. | % increase | GE-13536 | s.d. | % increase |
|---|---|---|---|---|---|---|---|---|
| 3 | 0.175 | 0.0043 | 0.341 | <0.0000 | 94.86 | 0.401 | 0.0013 | 129.14 |
| 5 | 0.180 | 0.0038 | 0.397 | 0.0051 | 120.56 | 0.416 | 0.0034 | 131.11 |
| 7 | 0.211 | 0.0009 | 0.473 | 0.0033 | 124.76 | 0.477 | 0.0080 | 126.07 |

TABLE 2

Fatty acids as percentage of total fatty acids

|  | C14:0 | C16:0 | C16:1 | C18:1 | C18:1 | C18:2 | C20:4 | C20:5 | Total FAME |
|---|---|---|---|---|---|---|---|---|---|
| WT-3730 | 4.9 | 27.5 | 28.9 | 2.5 | 0.6 | 1.9 | 4.1 | 28.9 | 100.0 |
| WT-3730 | 5.3 | 26.3 | 26.3 | 3.2 | 0.6 | 1.9 | 3.9 | 30.7 | 100.0 |
| GE-13535 | 3.1 | 44.1 | 34.9 | 9.2 | 0.9 | 0.8 | 1.6 | 3.2 | 100.0 |
| GE-13536 | 2.9 | 42.9 | 35.0 | 8.7 | 0.9 | 0.9 | 1.9 | 3.5 | 100.0 |

Figure 4:
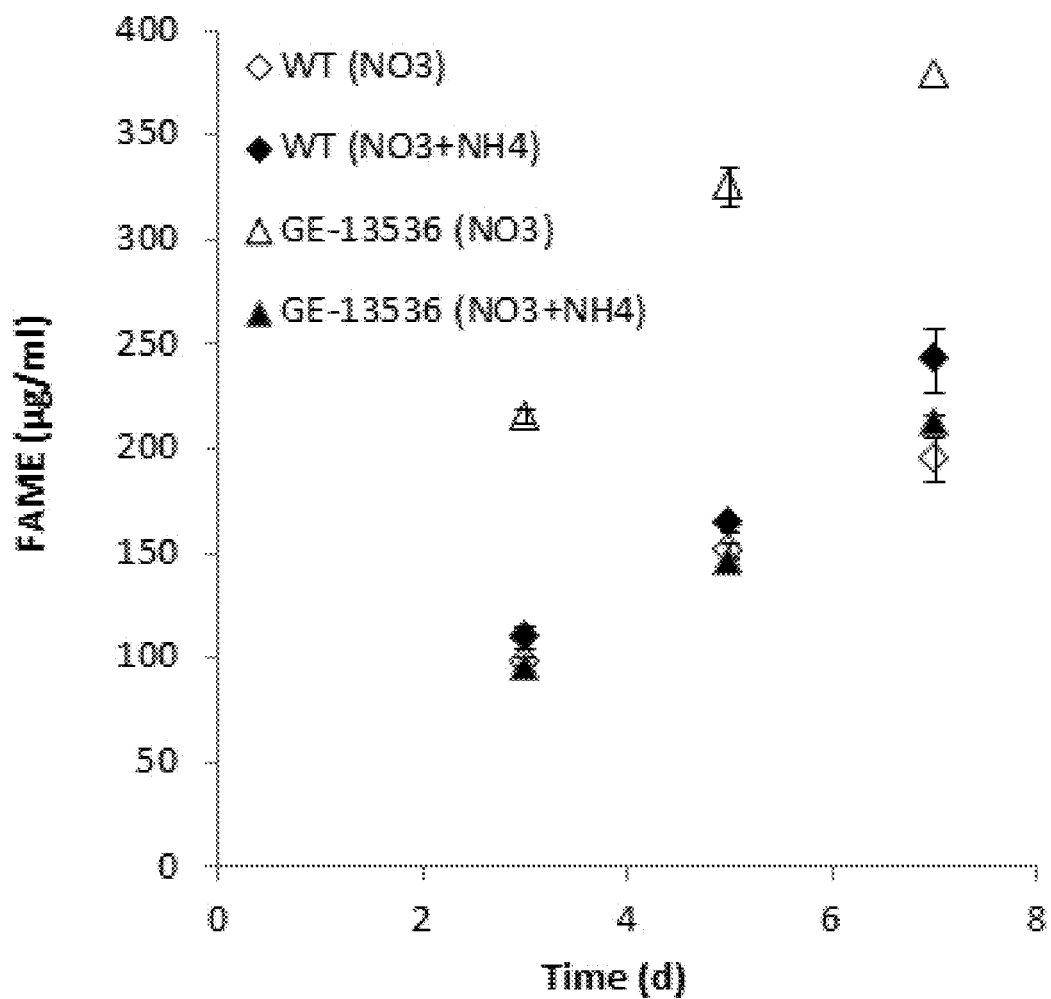
FIGS. 4-6 provide graphs depicting productivities of the *N. gaditana* wild type strain and GE-13536 knockout strain in batch assays in which the culture medium either contains nitrate ($NO_3$) as the only nitrogen source or is supplemented with ammonium ($NO_3+NH_4$).
Figure 5:
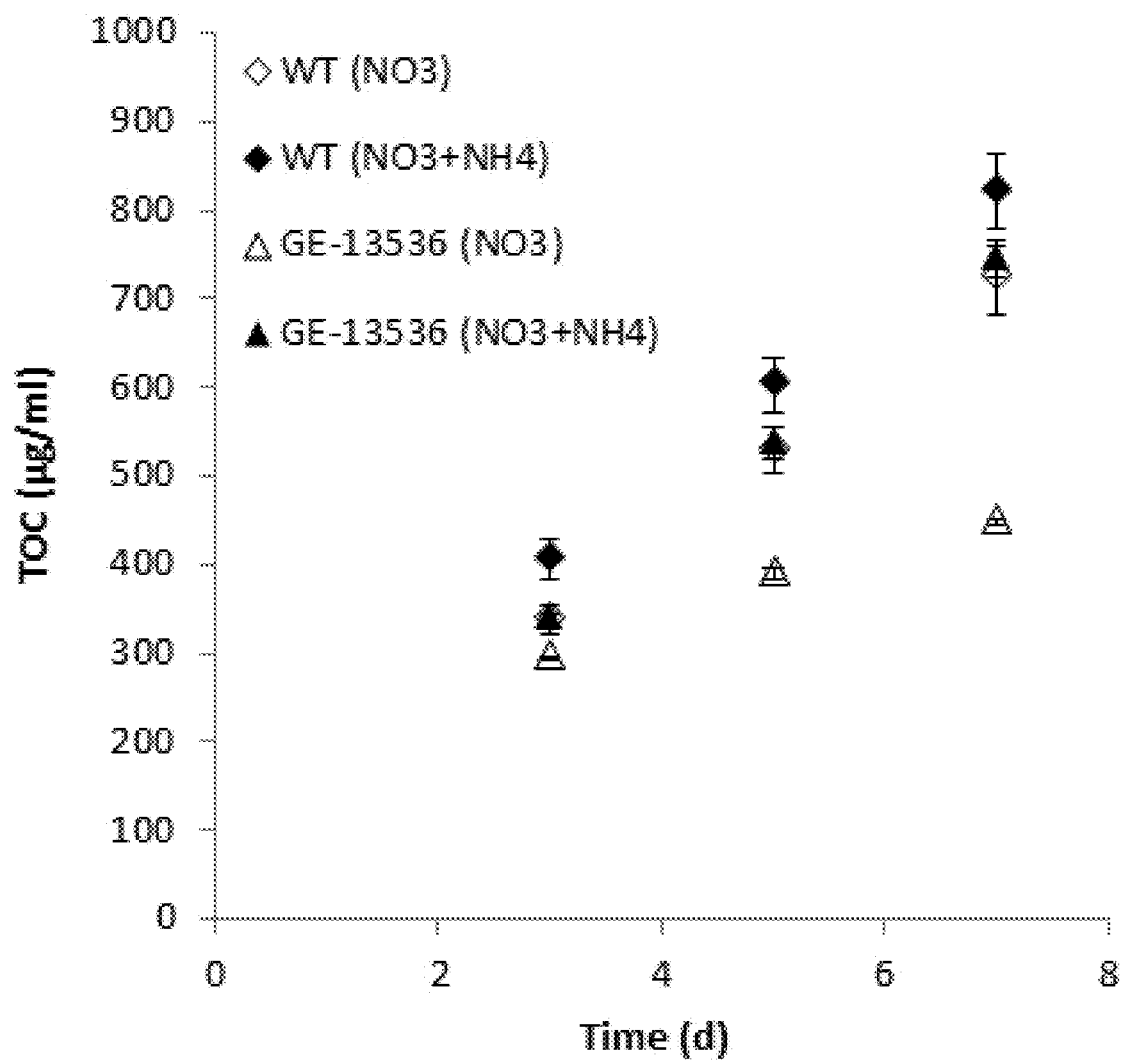
Figure 6:
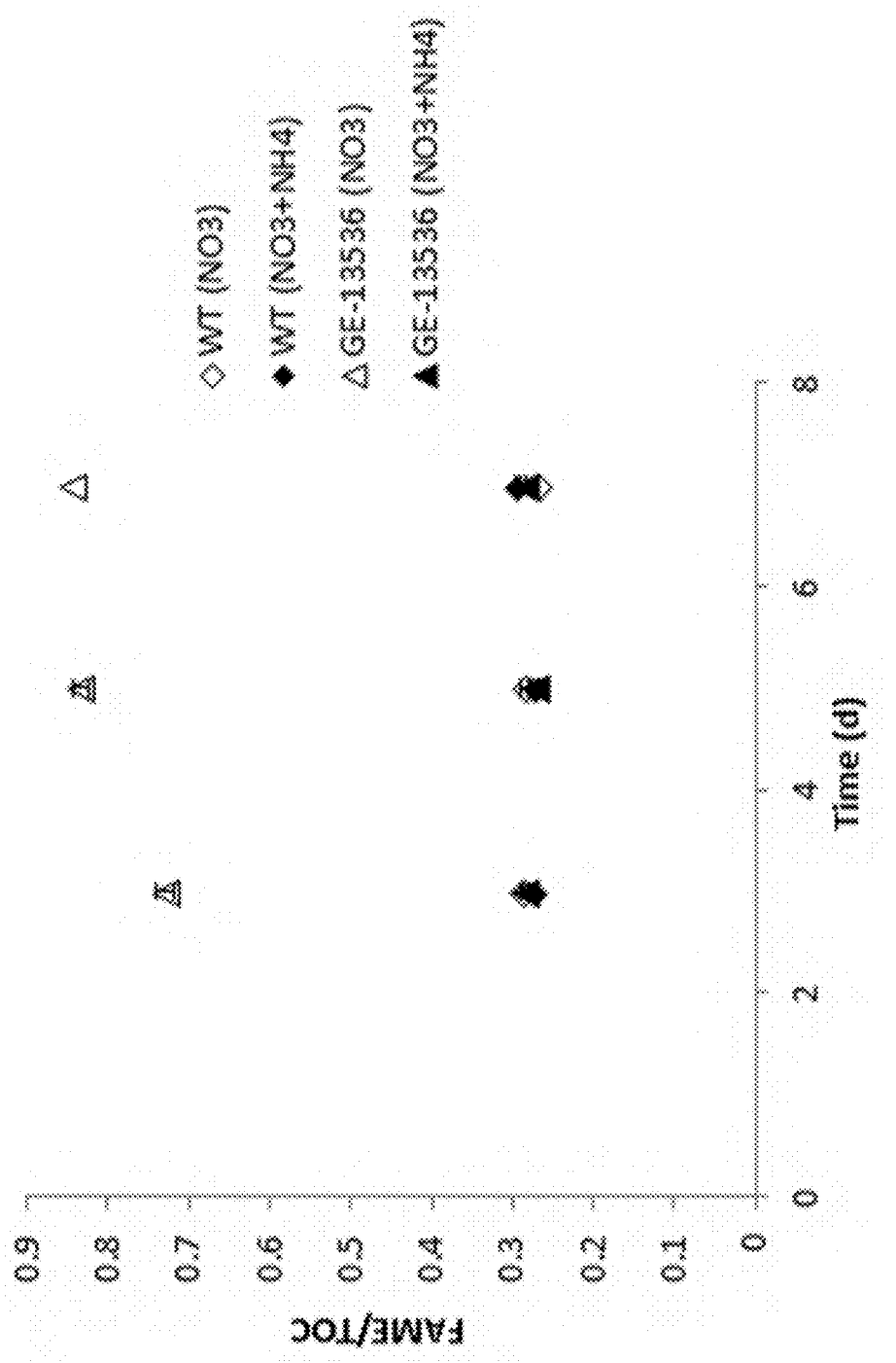

Since the two mutant strains GE-13535 and GE-13536 originated from the same transformation event and therefore contain the same mutation in the Naga_100020g79 locus, only one mutant strain (GE-13536) was selected for further testing. The mutant strain GE-13536 was cultured in a batch assay using two different nitrogen sources, one set of duplicate cultures with 8.8 mM nitrate (PM074 medium) and another set of duplicate cultures with 5 mM ammonium and 8.8 mM nitrate (PM124 medium)), along with duplicate cultures of the wild type under identical conditions, and assessed for productivity in comparison to wild type under each condition. Table 3 and FIG. 4 show that GE-13536 produced significantly more FAME than the wild type strain when grown on nitrate-only medium, demonstrating about 97% more FAME than the wild-type on Day 7; about 116% more FAME than the wild-type on Day 5; and 122% more FAME than the wild-type on Day 3. GE-13536 also exhibited a decrease in TOC (Table 3 and FIG. 5) compared to wild type when grown on nitrate-only medium. Over the course of the assay, the biomass of the GE-13536 mutant strain cultured on nitrate-only medium, as measured by TOC, was approximately 62-87% of the biomass of the wild-type strain cultured under the same conditions. Increases of approximately 154-214% in the FAME/TOC ratio (Table 5 and FIG. 6) were observed over the course of the experiment for GE-13536 when grown on nitrate-only medium as compared to the wild-type strain grown on the same medium. The mutant strain had similar FAME, TOC, and FAME/TOC ratios as the wild-type strain when ammonium was present in the culture medium. Thus, the Naga_100020g79 knockout mutant was induced for lipid biosynthesis on nitrate-only medium, but not when ammonium was present in the culture medium.

TABLE 3

FAME produced by wild-type and mutant strain GE-13536

| Days | Avg., s.d. WT (NO3) | Avg., s.d. WT (NO3 + NH4) | % increase | Avg., s.d. GE-13536 (NO3) | % increase | Avg., s.d. GE-13536 (NO3 + NH4) | % increase |
|---|---|---|---|---|---|---|---|
| 3 | 97.05 ± 3.15 | 109.59 ± 5.56 | 12.92 | 215.18 ± 3.79 | 121.72 | 95.09 ± 1.11 | −2.02 |
| 5 | 150.44 ± 4.10 | 163.91 ± 3.37 | 8.95 | 324.58 ± 9.25 | 115.75 | 145.84 ± 2.24 | −3.06 |
| 7 | 194.59 ± 10.27 | 242.05 ± 15.10 | 24.39 | 377.67 ± | 94.08 | 211.41 ± 4.72 | 8.64 |

TABLE 4

TOC produced by wild-type and mutant strain GE-13536

| Days | Avg., s.d. WT (NO3) | Avg., s.d. WT (NO3 + NH4) | % increase | Avg., s.d. GE-13536 (NO3) | % increase | Avg., s.d. GE-13536 (NO3 + NH4) | % increase |
|---|---|---|---|---|---|---|---|
| 3 | 338.85 ± 16.33 | 405.35 ± 23.41 | 19.62 | 294.85 ± 0.92 | −12.99 | 336.85 ± 8.13 | −0.59 |
| 5 | 528.6 ± 25.46 | 603 ± 30.69 | 14.07 | 389.55 ± 6.72 | −26.31 | 537.4 ± 17.96 | 1.66 |
| 7 | 724 ± 41.01 | 821.5 ± 41.58 | 13.47 | 448.6 ± | −38.04 | 742.5 ± 16.83 | 2.56 |

TABLE 5

FAME/TOC ratios for wild-type and mutant Strain GE-13536

| Days | Avg. WT (NO3) | Avg. WT (NO3 + NH4) | % increase | Avg. GE-13536 (NO3) | % increase | Avg. GE-13536 (NO3 + NH4) | % increase |
|---|---|---|---|---|---|---|---|
| 3 | 0.287 ± 0.0045 | 0.270 ± 0.0019 | −5.92 | 0.7298 ± 0.0106 | 154.29 | 0.28 ± 0.00 | −2.44 |
| 5 | 0.285 ± 0.0060 | 0.272 ± 0.0083 | −4.56 | 0.8331 ± 0.0094 | 192.32 | 0.27 ± 0.00 | −5.26 |
| 7 | 0.269 ± 0.0010 | 0.295 ± 0.0035 | 9.67 | 0.8445 ± | 213.94 | 0.29 ± 0.00 | 7.81 |

While certain embodiments have been described in terms of the examples and preferred embodiments, it is understood that variations and modifications will occur to those skilled in the art. Therefore, it is intended that the appended claims cover all such equivalent variations that come within the scope of the following claims.

Although the invention has been described with reference to the above examples, it will be understood that modifications and variations are encompassed within the spirit and scope of the invention. Accordingly, the invention is limited only by the following claims.

What is claimed is:

1. A mutant *Nannochloropsis* microorganism comprising a complete knockout of a gene encoding a polypeptide comprising a GAF2 domain having at least 90% sequence identity to SEQ ID NO: 1; and wherein the mutant microorganism:
   a) produces at least about 25% more lipid than a control microorganism; and/or
   b) exhibits increased partitioning of carbon to lipid with respect to the control microorganism; and
   when the mutant microorganism and control microorganism are cultured under identical conditions.

2. The mutant *Nannochloropsis* microorganism of claim 1, wherein the gene encodes a polypeptide comprising a GAF2 domain having at least 90% sequence identity to SEQ ID NO: 2.

3. The mutant *Nannochloropsis* microorganism of claim 1, wherein the mutant microorganism comprises a complete knockout of a gene comprising an open reading frame having at least 90% sequence identity to SEQ ID NO: 3.

4. The mutant *Nannochloropsis* microorganism of claim 1, wherein the control microorganism is a wild type microorganism.

5. The mutant *Nannochloropsis* microorganism of claim 1, wherein the mutant microorganism produces at least 100% more fatty acid methyl ester-derivatizable lipids (FAME lipids) than a control microorganism over a 5 day period.

6. The mutant *Nannochloropsis* microorganism of claim 5, wherein the culture medium comprises nitrate as the sole nitrogen source.

7. The mutant *Nannochloropsis* microorganism of claim 5, wherein the 7 day period occurs under photoautotrophic conditions.

8. The mutant *Nannochloropsis* microorganism of claim 1, wherein the mutant microorganism exhibits a FAME/TOC ratio at least 90% higher than the FAME/TOC ratio of the control microorganism.

9. The mutant *Nannochloropsis* microorganism according to claim 8, wherein the mutant microorganism exhibits a FAME/TOC ratio of at least about 0.35.

10. The mutant *Nannochloropsis* microorganism of claim 1, wherein lipid productivity is determined in a batch productivity assay.

11. The mutant *Nannochloropsis* microorganism of claim 1, wherein said identical conditions comprise culturing said mutant and control microorganisms in a medium comprising less than 2 mM ammonium.

12. The mutant *Nannochloropsis* microorganism according to claim 11, wherein said identical conditions comprise culturing said mutant and control microorganisms in a medium comprising nitrate as substantially the sole nitrogen source.

13. The mutant *Nannochloropsis* microorganism of claim 1, wherein said identical conditions comprise culturing said mutant and control microorganisms in a medium that is nutrient replete with respect to the control microorganism.

14. The mutant *Nannochloropsis* microorganism of claim 1, wherein the mutant microorganism is a genetically engineered mutant.

15. The mutant *Nannochloropsis* microorganism according to claim 14, wherein the deletion is generated using a Cas/CRISPR system.

16. The mutant *Nannochloropsis* microorganism of claim 14, wherein the mutant microorganism comprises an RNAi construct, a ribozyme construct, or an antisense construct that targets the gene encoding the polypeptide having a GAF domain, or a gene affecting the expression thereof.

17. The mutant *Nannochloropsis* microorganism according to claim 14, wherein the knockout is produced by site directed homologous recombination.

18. The mutant *Nannochloropsis* microorganism of claim 14, wherein the knockout is a truncation, frameshifting, or insertional mutation.

19. The mutant *Nannochloropsis* microorganism of claim 14, wherein the knockout is generated using meganuclease, zinc finger nuclease, a Transcription Activator-Like Effector Nuclease (TALEN) system, and/or a Cas/CRISPR system.

20. The mutant *Nannochloropsis* microorganism of claim 15, wherein the mutant microorganism comprises a Cas/CRISPR-mediated insertion into the gene.

21. The mutant *Nannochloropsis* microorganism of claim 1, wherein the mutant microorganism comprises at least one additional genetic modification that confers herbicide resistance, toxin resistance, enhanced growth properties, enhanced photosynthetic efficiency, enhanced lipid production or accumulation, and/or production of particular lipids.

22. A method of producing lipid, comprising culturing the mutant *Nannochloropsis* microorganism of claim 1 in a culture medium to produce lipid.

23. The method of claim 22, further comprising isolating lipid from the microorganism, the culture medium, or both.

24. The method of claim 22, wherein the microorganism is cultured using batch, continuous, or semi-continuous culture conditions.

25. The method of claim 22, wherein the microorganism is an alga and the culturing is under photoautotrophic conditions.

26. The method of claim 22, wherein the microorganism is cultured in a photobioreactor or fermenter.

27. The method of claim 22, wherein the microorganism is grown in a pond, canal, sea-based growth container, trench, raceway, or channel.

\* \* \* \* \*

```
                              SEQUENCE LISTING

<160> NUMBER OF SEQ ID NOS: 22

<210> SEQ ID NO 1
    <211> LENGTH: 91
    <212> TYPE: PRT
    <213> ORGANISM: Nannochloropsis gaditana
    <220> FEATURE:
    <221> NAME/KEY: misc_feature
    <223> OTHER INFORMATION: GAF2 domain of STP-4551

<400> SEQUENCE: 1

Leu Ser Gln Trp Ile Tyr Tyr Ser Arg Asn Phe Ala Phe Phe Glu Gly
    1               5                   10                  15

Gln Gly Met Pro Gly Arg Val Phe Arg Ser Gln Val Pro Glu Tyr Leu
                20                  25                  30

Glu Asn Ile Ala Ser Ile Asp Ala Lys Leu Phe Leu Arg Arg Asp Gly
                35                  40                  45

Ala Gln Val Ala Gly Val His Ser Ser Phe Gly Val Pro Leu Val Gln
            50                  55                  60

Asp Ser Val Ile Val Leu Val Phe Tyr Ser Asn His Asp Ser Ser
    65                  70                  75                  80

Ser His Ile Thr Gln Glu Leu Leu Asp Phe Val
                    85                  90

<210> SEQ ID NO 2
    <211> LENGTH: 1050
    <212> TYPE: PRT
    <213> ORGANISM: Nannochloropsis gaditana
    <220> FEATURE:
    <221> NAME/KEY: misc_feature
    <223> OTHER INFORMATION: STP-4551 protein

<400> SEQUENCE: 2

Met Ala Ser Ala His Gly Thr Ser Gly Ala Asn Val Met Leu Leu Ser
    1               5                   10                  15

Gly Gly Met Gly Asp Gly Lys Ala Phe Arg Glu Ala Ser Cys Pro Cys
                20                  25                  30

Pro Pro Phe Gln His Ser Ser Pro Thr Thr Lys Leu Tyr Gln Asn Gln
                35                  40                  45

Gly Gly Arg Gly Glu Gln Thr Met Pro Val Thr His Leu His Val Leu
            50                  55                  60

Pro Pro Arg Val Gln Lys Val Ser Ile Leu Ser Asn Asn Phe Pro Gln
    65                  70                  75                  80

Leu Gln Pro Lys Ala Gly Ser Tyr Cys Cys Lys Cys Gly Cys Pro Arg
                    85                  90                  95

Ala Asp Val Arg Leu Thr Cys Cys Asn Ser Val Val His Gly Arg Cys
                    100                 105                 110

Val Tyr Pro Trp Pro Val Thr Arg Cys Pro Ser Cys Ser Met Asp Gly
                    115                 120                 125

Lys Glu Met Ala Phe Glu Val Leu Leu Pro Glu Pro Tyr Thr Arg Asn
                130                 135                 140

Gly Ala Thr Leu Ser Leu Ser His Gln Glu Leu Ser Lys Lys Arg Gly
    145                 150                 155                 160
```

```
Gly Arg Trp Ser Glu Ala Glu Cys Ala Phe Ala Glu Leu Val Met Glu
            165                 170                 175
Gly Phe Gly Ser Gly Met Leu Pro Leu Arg Asp Gly Ser Arg Leu Gly
            180                 185                 190
Thr Phe Leu Cys Ser Leu Leu Gln Cys Thr Ser Ala Arg Leu Ser Ser
            195                 200                 205
Lys Leu Arg Thr Gly Lys Arg Asn Phe Arg Tyr Leu Val Asp Glu Gly
    210                 215                 220
Ile Ser Ala Glu Ser Ile Phe Arg Tyr Glu Gln Gln Arg Gln Leu
225                 230                 235                 240
Ser Arg Arg Glu Glu Leu Phe Leu His Tyr Leu Ser Pro Glu Glu Ala
            245                 250                 255
Ala Leu Ala Ser Arg Ser Leu Gln Leu Glu Trp Arg Leu Gln Phe Leu
            260                 265                 270
His Leu Gly Lys Gln Val Gly Val Arg Val Ser Asn Leu Tyr Glu Trp
            275                 280                 285
Asp Ala Phe Leu Lys Thr Val Val Pro Ala Ala Pro Lys Ala Val Gly
            290                 295                 300
Gly Ala Gly Gly Pro Gln Ala Leu Ser Gly Arg Lys Pro Glu Gly Asn
305                 310                 315                 320
Ala Glu Asp Asp Thr Thr Ser Pro Pro Thr Phe Ser Arg Lys Arg Arg
            325                 330                 335
Thr Ile Gly Pro Thr Val Ala Gln Cys Pro Asp Asn His Leu Gln Arg
            340                 345                 350
Val Arg Gly Ala Arg Gln Ala Ser Ala Glu Gln Asp Gly Ala Leu Pro
            355                 360                 365
Pro Ser Ser Leu Ala Thr Arg Gly Leu Gly Val Leu Met Leu Arg Leu
            370                 375                 380
Ala Ala Asp Lys His Arg Asn Phe Thr Val Gln Asn Gly Val Met Ala
385                 390                 395                 400
Ala Thr Ser Ile Glu Asp Leu Leu Leu Leu Arg Gln Ala Pro Gly
            405                 410                 415
Asp Glu Cys Ser Val Leu Ala Arg Ala Gly Asn Gly Ala Val Leu Phe
            420                 425                 430
Val Ser Val Gly Ile Lys Gly Leu Leu Gly Trp Gly Asp Ala Asp Leu
            435                 440                 445
Val Gly Thr Pro Leu Ile Asp Ala Lys Ser Arg Gly Cys Ala Thr
            450                 455                 460
Gly Ser Gly Phe Gln Gly Arg Leu Gly Arg Asn Gln Asn Gly Val Ile
465                 470                 475                 480
His Gly Glu Asp Gly Ser Val Leu Gln Ala Ala Val Arg Gln Ser Gln
            485                 490                 495
Val His Thr Ala Ser Val Leu Glu Arg Leu Gly Asn Pro Gln Leu Pro
            500                 505                 510
Val Gln Glu His Asp Leu Met Met Val Pro Leu Val Leu Arg Leu Tyr
            515                 520                 525
Arg Arg Asp Arg Thr Leu Val Arg Arg Gln Leu Thr Val Phe Ala Thr
            530                 535                 540
Glu Asp Phe Leu Leu Leu His Gly Ser Leu Ala Ala Pro Thr Pro Pro
545                 550                 555                 560
Val His Arg Ala Gln Gly Arg Arg Arg Glu Asn Val His Arg Pro Thr
            565                 570                 575
```

```
Lys Gln Cys Gly Tyr Gln Glu Gly Phe Tyr Leu Ser Gln His Glu Gly
                580                 585                 590

Gln His Thr Asp Asp Tyr Gln Pro Tyr Gln Gln Gln Gln Gln Gln Gln
            595                 600                 605

Tyr His Glu Glu His Gln Gly Gln Gln Glu Lys Gln Glu Pro Gln Gly
        610                 615                 620

Pro Gln Gln Trp Arg His Pro His Asp Val Gly His Val Glu Thr Arg
625                 630                 635                 640

Gln Gly Lys Glu Arg Asn Asp Phe Ser Gly His Leu Ser Lys Ser Ser
                645                 650                 655

Leu Thr Leu Ser Leu Arg Asn Leu Ala Leu Ala Pro Ser His Gln Tyr
            660                 665                 670

Pro Arg Val Tyr Arg Asn Thr Ser Phe Thr Ser Thr Leu Pro Leu Cys
        675                 680                 685

Arg Ala Ser Val Glu Arg Met Gln Ala Ser Ser Leu Ser Thr Asn Tyr
690                 695                 700

Val Gln Pro Ala His Leu Ser Tyr Glu Gln Val Val His Glu Glu Gly
705                 710                 715                 720

Gly Ala Leu Pro Leu Pro Glu Ser Ile Ile Gly Ser Arg Gly Pro Gln
                725                 730                 735

Ala His Ser Ile Thr Thr Ser Glu His Glu Ser Ser Val Pro Ile Ala
            740                 745                 750

Glu Gly Gly His Asp Met Asn Ser Cys Ile Leu His Gly Ala Ala Leu
        755                 760                 765

Leu Gly Arg Arg Ser Glu Val Ala Pro Thr Leu Val Leu Glu Ser Asn
770                 775                 780

Met Asp Val Glu Ala Arg Val Glu Gly Ala Ile Glu Arg Leu Glu Lys
785                 790                 795                 800

Trp Gly Ser Gln Leu Ser Glu Glu Gly Tyr Asn Ile Ala Thr Ser Ala
                805                 810                 815

Asp Asp Thr Ile Val Pro Arg Lys Gly Glu Ser Gly Leu Ala Glu Ala
            820                 825                 830

Glu Val Ile Glu Trp Ala Thr Asp Glu Asp Val Arg Leu Ala Leu Gly
        835                 840                 845

Glu His Ala Arg Glu Pro Thr Pro Gln Met Gln Arg Asp Ala Cys Gly
850                 855                 860

Gly Ala Tyr Asp Leu Cys Tyr Ser Pro Pro Ser Thr Phe Glu Glu Thr
865                 870                 875                 880

Met Arg Ala Phe Leu Leu Gly Leu Pro Ala Gln Cys Phe Gln Ser Ala
                885                 890                 895

Asp Ile Trp Val Pro Phe Arg Asp Pro Arg Thr Lys Arg Leu Ser Leu
            900                 905                 910

Gln Phe Gly Ser Gly Leu Ala Leu Arg Gly Asp Leu Ser Gln Trp Ile
        915                 920                 925

Tyr Tyr Ser Arg Asn Phe Ala Phe Phe Glu Gly Gln Gly Met Pro Gly
930                 935                 940

Arg Val Phe Arg Ser Gln Val Pro Glu Tyr Leu Glu Asn Ile Ala Ser
945                 950                 955                 960

Ile Asp Ala Lys Leu Phe Leu Arg Arg Asp Gly Ala Gln Val Ala Gly
                965                 970                 975

Val His Ser Ser Phe Gly Val Pro Leu Val Gln Asp Asp Ser Val Ile
            980                 985                 990

Val Leu Val Phe Tyr Ser Asn His  Asp Ser Ser Ser His  Ile Thr Gln
```

| | 995 | | | | 1000 | | | | | 1005 | |
|---|---|---|---|---|---|---|---|---|---|---|---|
| Glu | Leu | Leu | Asp | Phe | Val | Arg | Arg | Ala | Thr | Ala | Ser | Trp | Lys | Ile |
| | | 1010 | | | | | 1015 | | | | | 1020 | | |

Gln Thr Thr Phe Pro Val Pro Lys Ala Leu Thr Ala Asp Pro Asp
    1025                1030                1035

His Gln Pro Ala Val Val Arg Ser Ala Leu Leu Arg
    1040                1045                1050

<210> SEQ ID NO 3
<211> LENGTH: 3153
<212> TYPE: DNA
<213> ORGANISM: Nannochloropsis gaditana
<220> FEATURE:
<221> NAME/KEY: misc_feature
<223> OTHER INFORMATION: STP-4551 open reading frame (ORF)

<400> SEQUENCE: 3

```
atggcgtccg cgcatggcac gtccggcgcg aatgttatgc tcttgagcgg tggcatggga     60
gatggcaaag catttcggga ggcctcttgc ccttgtcctc cgtttcaaca ctccagtccg    120
acaaccaagc tttaccaaaa ccaaggtggg cgtggtgaac aaactatgcc tgtaacacac    180
ctacatgtac tgccgcctcg cgttcagaag gtgtccatat tgtcgaacaa tttcccccag    240
ttgcagccga aggcgggctc ctactgctgc aagtgcggtt gtccacgggc tgatgtcagg    300
ctgacatgtt gcaatagtgt cgtccatggc cgttgtgtat accatgcc cgtgactcgc    360
tgcccgagct gtagcatgga cgggaaagag atggcttttg aagtgcttct gccggagcct    420
tatacccgca acgcgcaac cttgtcgctc tctcaccagg agttgagtaa aaagcgtggg    480
gggcggtggt cagaagctga gtgtgcattt gcggagctgg ttatggaggg gttcggttcc    540
ggtatgttgc ccctgaggga cggcagtcgc cttggcacct tcctgtgtag cttgcttcaa    600
tgcacttcag cgcgcttgtc ctccaagtta cgcacgggca agcgaaattt tcggtatttg    660
gtggatgagg gcatttctgc cgaaagcatc ttccgatatg aacaggaaca cgccaactc    720
tcgcggcgcg aggagctctt cctgcattat ctctcccccg aggaggccgc actggcctct    780
cgcagtctgc aactggaatg cgcctccag ttcctgcacc tcggcaaaca agtgggcgta    840
cgggtaagca atttatacga atgggacgct tttctgaaga ccgtggtccc agccgccccg    900
aaagccgtgg gtggtgcagg tggccccag gccctctctg gcggaagcc cgaagggaac    960
gcagaggatg acaccacgtc gccgccgacc ttttctcgga agaggcggac gatcggtcct   1020
accgttgcac agtgccctga caatcacctt cagcgtgtgc gtggcgcccg gcaggcatcg   1080
gccgagcaag atggcgctct accaccgtct tccctcgcga ctcgaggatt aggcgtcctg   1140
atgctacgtc tggccgcgga caaacaccgg aacttcacgg tgcaaaacgg ggtcatggcc   1200
gccacttcaa tcgaggactt gcttctcctc ctgcggcaag ctcctggcga cgaatgttca   1260
gtcttagctc gggccgggaa cggagctgtc ctcttcgtct ccgttggtat taaaggcttg   1320
cttgggtggg gcgatgccga cctggtgggc actccgctca tcgatgcgaa gagcagagga   1380
ggatgtgcga cagggtccgg cttccaaggt cgtctcggca ggaaccagaa tgggtcatc   1440
catggagaag acgggagtgt tctgcaggcg gccgttcgtc aaagccaagt tcacactgcc   1500
agtgtgcttg agcgcctggg caatccgcag ctgccagttc aagagcatga tttgatgatg   1560
gtgcccctgg ttttacgcct gtatcgtcgg accgtactt tagtgcgccg gcagctcaca   1620
gtgttcgcca cggaagactt ccttctcctc cacggctctc tggcagctcc gactcctccg   1680
gtgcatcgag ctcaaggacg gagacgtgaa aacgtccatc ggccaactaa gcagtgtggc   1740
```

```
taccaggaag gattttacct gtcgcagcat gaaggacagc acactgatga ctatcaacct    1800
tatcagcagc agcaacagca gcaataccac gaggagcacc aaggccagca agaaaaacaa    1860
gaaccgcaag gtcctcagca atggcggcac ccgcatgacg ttggacacgt tgaaacaagg    1920
cagggcaagg agagaaatga ttttcaggc cacttgtcga aaagctcgct gacattgtct     1980
cttcggaatc tagcgcttgc tccatcacat caatacccctc gtgtctaccg caatacttct   2040
ttcacctcga ccttacccct ttgtcgagca tctgtggaaa ggatgcaggc atctagttta   2100
tcgaccaatt atgtgcagcc tgcccatcta agctacgagc aggttgttca tgaagagggc   2160
ggggctcttc ccttacctga gtcgattatc ggctcccgtg accgcaagc gcatagcatt    2220 accacgtccg agcatgagag tagtgtaccg atcgctgagg gtggtcatga tatgaatagc   2280
tgcattcttc atggcgcggc tctactgggc cgccgcagtg aggttgcccc aacattagtc   2340
ctggagtcca acatggacgt ggaagcacgg gtggagggtg ccatcgagcg gttggaaaag   2400 tggggggtctc aattaagtga ggagggttat aatatcgcaa caagcgcaga tgacactatc   2460
gtgcctcgta aaggagaaag cgggctggcc gaggcggagg tcatcgagtg ggcgacggat    2520
gaggacgtga ggctggcgct cggagagcat gctcgtgagc ccacgcctca aatgcagcgt    2580
gatgcctgtg gaggagctta cgacctctgc tactctcctc catccaccctt tgaggagaca   2640 atgcgcgcgt ttttgctcgg tctgcctgcc cagtgcttcc aaagcgctga tatctgggtg    2700
ccattccggg accctcgcac taagcggctt tcgcttcaat ttggcagcgg gttagctctt    2760
cgaggagact tatacagtg gatttactac tctcgaaact ttgcctttt tgaagggcaa      2820 ggaatgccgg ggcgagtctt tcgctcgcag gtgcccgagt acctggagaa tatcgcctcc    2880
atcgacgcca aacttttcct acgtcgagat ggggcgcaag tcgctggagt ccactcatcc    2940
ttcggtgtcc ccctcgtgca ggatgactca gtgattgttt tggtcttcta ctcgaaccac    3000
gactcgtcat ctcatatcac ccaggagctg ctagacttcg ttcgtcgagc cacagcatct    3060
tggaaaatcc agaccacgtt tcccgtacca aaggccttga cggcagatcc cgaccatcaa    3120
ccagctgtcg tgcgctcagc tttattaagg tag                                 3153
```

<210> SEQ ID NO 4
<211> LENGTH: 21
<212> TYPE: DNA
<213> ORGANISM: Nannochloropsis gaditana
<220> FEATURE:
<221> NAME/KEY: misc_feature
<223> OTHER INFORMATION: Target sequence in STP-4551 gene

<400> SEQUENCE: 4

```
acgctgaagg tgattgtcag g                                                21
```

<210> SEQ ID NO 5
<211> LENGTH: 4101
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Cas9 gene codon optimized for Nannochloropsis

<400> SEQUENCE: 5

```
gacaagaagt actccatcgg gctggacatc gggacgaact ccgtgggatg ggccgtgatc    60
acagacgaat acaaggtgcc ttccaagaag ttcaaggtgc tggggaacac ggacagacac   120
```

| | |
|---|---|
| tccatcaaga agaacctcat cggggccttg ctcttcgact ccggagaaac cgccgaagca | 180 |
| acgcgattga aaagaaccgc cagaagacga tacacacgac ggaagaaccg catctgctac | 240 |
| ctccaggaga tcttcagcaa cgagatggcc aaggtggacg actcgttctt tcatcgcctg | 300 |
| gaggagagct tcctggtgga ggaagacaag aaacatgagc gccacccgat cttcgggaac | 360 |
| atcgtggacg aagtggccta ccacgagaaa taccccacga tctaccactt gcgcaagaaa | 420 |
| ctcgtggact ccacggacaa agcggacttg cggttgatct acttggcctt ggcccacatg | 480 |
| atcaaatttc ggggccactt cctgatcgag ggcgacttga atcccgacaa ttccgacgtg | 540 |
| gacaagctct tcatccagct ggtgcagacc tacaaccagc tcttcgagga gaaccccatc | 600 |
| aatgcctccg gagtggacgc caaagccatc ttgtccgccc gattgtccaa atccagacgc | 660 |
| ttggagaact tgatcgcaca acttcctggc gagaagaaga acggcctctt cggcaacttg | 720 |
| atcgcgctgt cgctgggatt gacgcctaac ttcaagtcca acttcgactt ggccgaggac | 780 |
| gccaagttgc aactgtccaa ggacacctac gacgacgacc tcgacaacct gctggcccaa | 840 |
| attggcgacc aatacgcgga cttgttttg gcggccaaga acttgagcga cgccatcttg | 900 |
| ttgagcgaca tcttgcgcgt gaatacggag atcaccaaag cccctttgtc cgcctctatg | 960 |
| atcaagcggt acgacgagca ccaccaagac ttgaccctgt tgaaagccct cgtgcggcaa | 1020 |
| caattgcccg agaagtacaa ggagatcttc ttcgaccagt ccaagaacgg gtacgccggc | 1080 |
| tacatcgacg gaggagcctc ccaagaagag ttctacaagt tcatcaagcc catcctggag | 1140 |
| aagatggacg gcaccgagga gttgctcgtg aagctgaacc gcgaagactt gttgcgaaaa | 1200 |
| cagcggacgt tcgacaatgg cagcatcccc caccaaatcc atttgggaga gttgcacgcc | 1260 |
| atcttgcgac ggcaagagga cttctacccg ttcctgaagg acaaccgcga gaaaatcgag | 1320 |
| aagatcctga cgttcagaat cccctactac gtgggaccct tggcccgagg caattcccgg | 1380 |
| tttgcatgga tgacgcgcaa aagcgaagag acgatcaccc cctggaactt cgaagaagtg | 1440 |
| gtcgacaaag gagcatccgc acagagcttc atcgagcgaa tgacgaactt cgacaagaac | 1500 |
| ctgcccaacg agaaggtgtt gcccaagcat cgctgctgt acgagtactt cacggtgtac | 1560 |
| aacgagctga ccaaggtgaa gtacgtgacc gagggcatgc gcaaacccgc gttcctgtcg | 1620 |
| ggagagcaaa agaaggccat tgtggacctg ctgttcaaga ccaaccggaa ggtgaccgtg | 1680 |
| aaacagctga agaggacta cttcaagaag atcgagtgct cgactccgt ggagatctcc | 1740 |
| ggcgtggagg accgattcaa tgcctccttg gaacctacc atgacctcct gaagatcatc | 1800 |
| aaggacaagg acttcctgga caacgaggag aacgaggaca tcctggagga catcgtgctg | 1860 |
| accctgaccc tgttcgagga ccgagagatg atcgaggaac ggttgaaaac gtacgcccac | 1920 |
| ttgttcgacg acaaggtgat gaagcagctg aaacgccgcc gctacaccgg atggggacga | 1980 |
| ttgagccgca aactgattaa tggaattcgc gacaagcaat ccggaaagac catcctggac | 2040 |
| ttcctgaagt ccgacgggtt cgccaaccgc aacttcatgc agctcatcca cgacgactcc | 2100 |
| ttgaccttca aggaggacat ccagaaggcc caagtgtccg acaaggaga ctccttgcac | 2160 |
| gagcacatcg ccaatttggc cggatccccc gcaatcaaaa aaggcatctt gcaaaccgtg | 2220 |
| aaagtggtcg acgaactggt gaaggtgatg ggacggcaca gcccgagaa catcgtgatc | 2280 |
| gaaatggccc gcgagaacca aaccacccaa aaaggacaga gaactcccg agagcgcatg | 2340 |
| aagcggatcg aagagggcat caaggagttg ggctcccaga tcctgaagga gcatcccgtg | 2400 |
| gagaatacc aattgcaaaa cgagaagctc tacctctact acctccagaa cgggcgggac | 2460 |
| atgtacgtcg accaagagct ggacatcaac cgcctctccg actacgatgt ggatcatatt | 2520 |

```
gtgccccaga gcttcctcaa ggacgacagc atcgacaaca aggtcctgac gcgcagcgac    2580
aagaaccggg gcaagtctga caatgtgcct tccgaagaag tcgtgaagaa gatgaagaac    2640
tactggcggc agctgctcaa cgccaagctc atcacccaac ggaagttcga caacctgacc    2700
aaggccgaga gaggaggatt gtccgagttg acaaagccg gcttcattaa cgccaactc     2760 gtggagaccc gccagatcac gaagcacgtg gcccaaatct tggactcccg gatgaacacg    2820
aaatacgacg agaatgacaa gctgatccgc gaggtgaagg tgatcacgct gaagtccaag    2880
ctggtgagcg acttccggaa ggacttccag ttctacaagg tgcgggagat caacaactac    2940
catcacgccc atgacgccta cctgaacgcc gtggtcggaa ccgccctgat caagaaatac    3000
cccaagctgg agtccgaatt cgtgtacgga gattacaagg tctacgacgt gcggaagatg    3060
atcgcgaagt ccgagcagga gatcggcaaa gccaccgcca gtacttctt ttactccaac     3120 atcatgaact tcttcaagac cgagatcacg ctcgccaacg gcgagatccg caagcgcccc    3180
ctgatcgaga ccaacggcga gacgggagag attgtgtggg acaaaggaag agattttgcc    3240
acagtgcgca aggtgctgtc catgcctcag gtgaacatcg tgaagaagac cgaggtgcaa    3300
acaggagggt tttccaaaga gtccattttg cctaaggaga attccgacaa gctcatcgcc    3360
cgcaagaagg actgggaccc caagaagtac gggggcttcg actccccac ggtggcctac      3420 tccgtgttgg tggtggccaa agtggagaaa gggaagagca gaagctgaa atccgtgaag     3480 gagttgctcg gaatcacgat catggaacga tcgtcgttcg agaaaaaccc catcgacttc    3540
ctcgaagcca aagggtacaa agaggtgaag aaggacctga tcatcaagct gcccaagtac    3600
tccctgttcg agctggagaa cggccgcaag cggatgctgg cctccgccgg ggaactgcag    3660
aaagggaacg aattggcctt gccctccaaa tacgtgaact tcctctactt ggcctcccat    3720
tacgaaaagc tcaaaggatc ccctgaggac aatgagcaga agcaactctt cgtggaacaa    3780
cacaagcact acctggacga gatcatcgag cagatcagcg agttctccaa gcgcgtgatc    3840
ctcgccgacg ccaacctgga caaggtgctc tccgcctaca acaagcaccg cgacaagcct    3900
atccgcgagc aagccgagaa tatcattcac ctgtttaccc tgacgaattt gggagcccct    3960 gccgcctta  aatactttga caccaccatc gaccgcaaaa gatacacctc caccaaggaa    4020
gtcttggacg ccaccctcat ccaccagtcc atcacgggcc tctacgagac gcgcatcgac    4080
ctctcccaat tgggcggcga c                                             4101
```

<210> SEQ ID NO 6
<211> LENGTH: 24
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Nuclear localization sequence

<400> SEQUENCE: 6

```
cccaagaaaa agcggaaggt cggc                                            24
```

<210> SEQ ID NO 7
<211> LENGTH: 24
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: FLAG tag

<400> SEQUENCE: 7
gactacaagg atgacgatga caag                                              24

<210> SEQ ID NO 8
<211> LENGTH: 147
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Nuclear localization sequence-peptide linker-
      FLAG tag

<400> SEQUENCE: 8
atgcccaaga aaaagcggaa ggtcggcgac tacaaggatg acgatgacaa gttggagcct        60
ggagagaagc cctacaaatg ccctgagtgc ggaaagagct tcagccaatc tggagccttg       120
acccggcatc aacgaacgca tacacga                                          147

<210> SEQ ID NO 9
<211> LENGTH: 1000
<212> TYPE: DNA
<213> ORGANISM: Nannochloropsis gaditana
<220> FEATURE:
<221> NAME/KEY: misc_feature
<223> OTHER INFORMATION: RPL24 promoter

<400> SEQUENCE: 9
aataagcata catcatatga atacaattca gcttaaattt atcatacaaa gatgtaagtg        60
cagcgtgggt ctgtaacgat cgggcgtaat ttaagataat gcgagggacc ggggaggtt       120 ttggaacgga atgaggaatg ggtcatggcc cataataata atatgggttt ggtcgcctcg       180
cacagcaacc gtacgtgcga aaaggaaca gatccattta ataagttgaa cgttattctt       240
tcctatgcaa tgcgtgtatc ggaggcgaga gcaagtcata ggtggctgcg cacaataatt       300
gagtctcagc tgagcgccgt ccgcgggtgg tgtgagtggt catcctcctc ccggcctatc       360
gctcacatcg cctctcaatg gtggtggtgg ggcctgatat gacctcaatg ccgacccata       420
ttaaaaccca gtaaagcatt caccaacgaa cgagggctc ttttgtgtgt gttttgagta       480
tgattttaca cctctttgtg catctctctg gtcttccttg gttcccgtag tttgggcatc       540
atcactcacg cttccctcga ccttcgttct tcctttacaa ccccgacaca ggtcagagtt       600
ggagtaatca aaaaggggt gcacgaatga gatacattag attttgacag atatcctttt       660
actggagagg gttcaaggga tcaaatgaac agcgggcgtt ggcaatctag ggagggatcg       720
gaggttggca gcgagcgaaa gcgtgtccat ccttttggct gtcacacctc acgaaccaac       780
tgttagcagg ccagcacaga tgacatacga gaatctttat tatatcgtag accttatgtg       840
gatgaccttt ggtgctgtgt gtctggcaat gaacctgaag gcttgatagg gaggtggctc       900
ccgtaaaccc tttgtccttt ccacgctgag tctccccgc actgtccttt atacaaattg       960
ttacagtcat ctgcaggcgg ttttctttg gcaggcaaag                            1000

<210> SEQ ID NO 10
<211> LENGTH: 317
<212> TYPE: DNA
<213> ORGANISM: Nannochloropsis gaditana
<220> FEATURE:
<221> NAME/KEY: misc_feature
<223> OTHER INFORMATION: Bidirectional terminator 2

<400> SEQUENCE: 10

```
agtgatgcgg cctttaggaa acaccacaaa agtaattgac aatctcagga acgatctgcg      60
tgtttacagc ttcccaaata acaattatac cacgtaccaa aaggggttta atgtatctca     120
caaattcttc taataggtac agcttctcaa attgggtgta tgatgtgaca cttcgtctca     180
cacacgtcac gataattcag cgtatggctt cccttcatca cattcacgca aacttctaca     240
caaccctggg catatttctt gtgttggcaa cactcccgaa atcgattctg cacacaatgg     300
ttcattcaat gattcaa                                                    317
```

<210> SEQ ID NO 11
<211> LENGTH: 399
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: blasticidin S deaminase gene from Aspergillus
      terreus codon optimized for Nannochloropsis gaditana

<400> SEQUENCE: 11

```
atggccaagc ctttatccca gaggaatcc acgctgatcg aacgtgcaac tgcgaccatc       60
aacagcatac ctattagcga ggactactcg gtggccagtg cagccctctc gtccgacggt     120
cggatcttta ccggcgtgaa tgtatatcat ttcaccggag ggccatgcgc ggagctcgtg     180
gtcctcggaa cggccgctgc ggctgctgcc ggaaatctga cgtgcatagt ggccatcggg     240
aacgaaaacc gcggcattct gtctccgtgc gggcgatgtc ggcaggtgct gcttgacttg     300
cacccgggga tcaaggcaat tgtcaaagat tccgatgggc agcccacagc ggttggcatc     360
agggagttgc ttccctctgg ctacgtctgg gagggttga                            399
```

<210> SEQ ID NO 12
<211> LENGTH: 999
<212> TYPE: DNA
<213> ORGANISM: Nannochloropsis gaditana
<220> FEATURE:
<221> NAME/KEY: misc_feature
<223> OTHER INFORMATION: TCTP promoter

<400> SEQUENCE: 12

```
cgtgcaggtg tacagattga aggaaacaat ggagatatct ttggcagttg aaaaccgtgt      60
tcgaatcatg cttttctact ctccaactga gacgaaattt atagcgccat gtcgcttctg    120
actaccaggc ttaggaaggc ctcatcacaa gctggatcgg ttcgaattaa gcaggcactg    180
aagccaagct tgcaagacag ccaccttta attccctcaa acactttct caattcagcc      240
cggtaaatat gccgattcac agcggccaag atagagggga ggttagcaag aatgttgcga    300
tccctcccca gtcgttgcct cgcacacaac ctaggcctttc accttttccat ggaaaattga   360
gaagtgaata ttggttttct tacggcatat cagatgaaat catgacccct aaacatgaag    420
agctgcaggc aaaacacctg ctctggacga gcacgatgaa atctcgagaa cccgccgtac    480
ttcagttgat cccgcatgat gacggccgcc attgaaataa gccacctcac tttattctag    540
caccgatttc caccgttgtg agggccgaac gaggacaatt tcgtgcgaaa caagcacgaa    600
cacgcacacg attagtagta cagacgagca gatcgatggc atgcggcacg gtctcgcgtt    660
ctcggcgacc aggacaacgg agcagaggga ggcctgccga gttccgaggg gcatttagt    720
ccaaaattgt gttgacacgt gaacaagtgg cttgaaaaga ggaaggaaat gcctgggttt    780
```

```
cccttcgaga gcgggaactc gcttgtgcgt catcctagct acccatggtc cctttgtggg    840
ggaggctgtt tcgtcctacc gaatgtgtgg cgctccatgc atcttctgcc tcccaaacca    900
ccaacatgag cacgcgaagg aaggagaaaa aagtggccgc aacgttctct tctcatattt    960
attgtctcat cacaaacata ggtacataat acaacaatc                           999
```

```
<210> SEQ ID NO 13
<211> LENGTH: 318
<212> TYPE: DNA
<213> ORGANISM: Nannochloropsis gaditana
<220> FEATURE:
<221> NAME/KEY: misc_feature
<223> OTHER INFORMATION: EIF3 terminator

<400> SEQUENCE: 13
ggcactgtaa ccccggttcc gctcgacgaa ggctgggagc gccctttcgg tgggataaaa     60
tggatgcttt accgctgcgc ttcggctgag gaagagagaa atgcgagcgg ggatcggggt    120
cctagaaacg aagaaaggag aacaagttcc tggccaaaga aaaacaagac aaataccctc    180
tccaggcctg ggcccattac ttttttttgc tgtttcttat acctgcactc gtgcttctct    240
agtctgtcga gaccttacct gatcttcctc cctccatcgc tccccgcccc cccatccga    300 gcaaccgtcg accatacg                                                  318
```

```
<210> SEQ ID NO 14
<211> LENGTH: 121
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: STP-4551 guide RNA sense oligonucleotide

<400> SEQUENCE: 14
taatacgact cactataacg ctgaaggtga ttgtcagggt tttagagcta gaaatagcaa     60
gttaaaataa ggctagtccg ttatcaactt gaaaaagtgg caccgagtcg gtgctttttt    120
t                                                                    121
```

```
<210> SEQ ID NO 15
<211> LENGTH: 121
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: STP-4551 guide RNA reverse complement
      oligonucleotide

<400> SEQUENCE: 15
aaaaaaagca ccgactcggt gccactttt caagttgata acggactagc cttattttaa     60
cttgctattt ctagctctaa aaccctgaca atcaccttca gcgttatagt gagtcgtatt    120
a                                                                    121
```

```
<210> SEQ ID NO 16
<211> LENGTH: 1029
<212> TYPE: DNA
<213> ORGANISM: Artificial Sequence
<220> FEATURE:
<223> OTHER INFORMATION: Synthetic
<220> FEATURE:
```

<221> NAME/KEY: misc_feature
<223> OTHER INFORMATION: Hyg resistance gene

<400> SEQUENCE: 16

```
atggggaaga aaccggaact gaccgctacg tccgtggaga aattccttat tgagaagttc      60
gactctgtct ccgacttgat gcaactgagc gagggagagg agagtagggc gttctcgttt     120
gacgtagggg gtcggggata cgtgttgagg gttaatagtt gtgcggacgg gttctacaag     180
gatcggtatg tctaccgtca tttcgcctcc gccgctctcc ccataccaga ggtactggac     240
attggggagt ttagcgaatc tctcacgtac tgcatctcgc gccgagccca gggagtgacg     300
ttgcaagatc tgcccgaaac tgaattgcct gccgttttgc aacccgtggc cgaggccatg     360
gacgcgatcg ctgccgcaga tctgtctcag acgtccggct ttggaccttt tgggccccag     420
ggcatcgggc agtacacgac ctggcgagac ttcatctgcg ccattgccga tcctcacgtc     480
tatcattggc agacagtcat ggatgacacc gtgtctgcat ccgtggccca agcactggac     540
gaactcatgt tgtgggccga ggattgccct gaggtcaggc acctggtgca cgcggatttc     600
ggcagcaata acgtacttac agacaatggt cggattactg ctgtcatcga ctggtccgaa     660
gcgatgtttg gtgatagcca atacgaagtg gcgaacatat tcttctggcg tccctggttg     720
gcgtgcatgg agcagcagac acgctacttt gaacggaggc acccggagct ggccggctcc     780
ccacgactcc gcgcctatat gttgcgtatc ggactcgatc agctttacca gtctctcgtc     840
gacggcaact tcgacgacgc cgcgtgggcg cagggccgct gcgacgcgat agtccgcagc     900
ggggctggga cggtgggtcg gacccaaatc gcacgccggt cggctgcggt gtggacagac     960
ggctgtgttg aggtgcttgc ggactcgggc aaccgtaggc cgagcacccg accgcgtgca    1020
aaggagtga                                                           1029
```

<210> SEQ ID NO 17
<211> LENGTH: 1000
<212> TYPE: DNA
<213> ORGANISM: Nannochloropsis gaditana
<220> FEATURE:
<221> NAME/KEY: misc_feature
<223> OTHER INFORMATION: EIF3 promoter

<400> SEQUENCE: 17

```
tcataatcaa agatgagcca gccacgaagc taccggagaa ttctgtaaga aaatgttta      60
aagttgaaaa tgctaacagt gaagtgatat ccttttttaa tggagtgttg aggtgaagtc     120
tagcatcgta ggggaaaaca ggattctgtg tcttccattc tactccttga taaagcgaag     180
aaatccgaca aaaccaaaga gattgttcaa gtttaagatt tgtaagcgta caactatgaa     240
cttcttctct ttgtaggcct gagtggtcgt atgcatacga ttcatgaagt gaatcagtat     300
cgctggattt tgcttaggag taaagcacaa ctaagaaaat atgctgcctg gcaggcatcc     360
tgagacatga ggcaagcgac gtagcaattg aatcctaatt taagccaggg catctgtatg     420
actctgttag ttaattgatg aaccaatgag ctttaaaaaa aaatcgttgc gcgtaatgta     480
gttttaattc tccgccttga ggtgcggggc catttcggac aaggttcttt ggacggagat     540
ggcagcatgt gtcccttctc caaattggtc cgtgtggtag ttgagatgct gccttaaaat     600
tctgctcggt catcctgcct tcgcattcac tcctttcgag ctgtcgggtt cctcacgagg     660
cctccgggag cggattgcgc agaaaggcga cccggagaca cagagaccat acaccgacta     720
aattgcactg gacgatacgg catggcgacg acgatggcca agcattgcta cgtgattatt     780
cgccttgtca ttcagggaga aatgatgaca tgtgtgggac ggtctttaca tgggaagagg     840
```

```
gcatgaaaat aacatggcct ggcgggatgg agcgtcacac ctgtgtatgc gttcgatcca    900
caagcaactc accatttgcg tcggggcctg tctccaatct gctttaggct acttttctct    960
aatttagcct attctataca gacagagaca cacagggatc                         1000
```

```
<210> SEQ ID NO 18
<211> LENGTH: 27
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: 27 nucleotide 5' ID sequence

<400> SEQUENCE: 18
tccacagccc gaacccatga gagagaa                                         27
```

```
<210> SEQ ID NO 19
<211> LENGTH: 27
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: 27 nucleotide 3' ID sequence

<400> SEQUENCE: 19
gcccgaatcg agttgatggc ccgcaaa                                         27
```

```
<210> SEQ ID NO 20
<211> LENGTH: 2400
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: HygR cassette with flanking ID sequences

<400> SEQUENCE: 20
tccacagccc gaacccatga gagagaatca taatcaaaga tgagccagcc acgaagctac     60
cggagaattc tgtaagaaaa atgtttaaag ttgaaaatgc taacagtgaa gtgatatcct    120
tttttaatgg agtgttgagg tgaagtctag catcgtaggg gaaaacagga ttctgtgtct    180
tccattctac tccttgataa agcgaagaaa tccgacaaaa ccaaagagat tgttcaagtt    240
taagatttgt aagcgtacaa ctatgaactt cttctctttg taggcctgag tggtcgtatg    300
catacgattc atgaagtgaa tcagtatcgc tggattttgc ttaggagtaa agcacaacta    360
agaaaatatg ctgcctggca ggcatcctga gacatgaggc aagcgacgta gcaattgaat    420
cctaatttaa gccagggcat ctgtatgact ctgttagtta attgatgaac caatgagctt    480
taaaaaaaaa tcgttgcgcg taatgtagtt ttaattctcc gccttgaggt gcggggccat    540
ttcggacaag gttctttgga cggagatggc agcatgtgtc ccttctccaa attggtccgt    600
gtggtagttg agatgctgcc ttaaaattct gctcggtcat cctgccttcg cattcactcc    660
tttcgagctg tcgggttcct cacgaggcct ccgggagcgg attgcgcaga aaggcgaccc    720
ggagacacag agaccataca ccgactaaat tgcactggac gatacggcat ggcgacgacg    780
atggccaagc attgctacgt gattattcgc cttgtcattc agggagaaat gatgacatgt    840
gtgggacggt ctttacatgg aagagggca tgaaaataac atggcctggc gggatggagc    900
```

```
gtcacacctg tgtatgcgtt cgatccacaa gcaactcacc atttgcgtcg gggcctgtct    960
ccaatctgct ttaggctact tttctctaat ttagcctatt ctatacagac agagacacac   1020
agggatcatg gggaagaaac cggaactgac cgctacgtcc gtggagaaat tccttattga   1080
gaagttcgac tctgtctccg acttgatgca actgagcgag ggagaggaga gtagggcgtt   1140
ctcgtttgac gtaggggtc ggggatacgt gttgagggtt aatagttgtg cggacgggtt   1200
ctacaaggat cggtatgtct accgtcattt cgcctccgcc gctctcccca taccagaggt   1260
actggacatt ggggagttta gcgaatctct cacgtactgc atctcgcgcc gagcccaggg   1320
agtgacgttg caagatctgc ccgaaactga attgcctgcc gttttgcaac ccgtggccga   1380
ggccatggac gcgatcgctg ccgcagatct gtctcagacg tccggctttg gacctttttgg   1440 gccccagggc atcgggcagt acacgacctg gcgagacttc atctgcgcca ttgccgatcc   1500
tcacgtctat cattggcaga cagtcatgga tgacaccgtg tctgcatccg tggcccaagc   1560
actggacgaa ctcatgttgt gggccgagga ttgccctgag gtcaggcacc tggtgcacgc   1620
ggatttcggc agcaataacg tacttacaga caatggtcgg attactgctg tcatcgactg   1680
gtccgaagcg atgtttggtg atagccaata cgaagtggcg aacatattct tctggcgtcc   1740
ctggttggcg tgcatggagc agcagacacg ctactttgaa cggaggcacc cggagctggc   1800
cggctcccca cgactccgcg cctatatgtt gcgtatcgga ctcgatcagc tttaccagtc   1860
tctcgtcgac ggcaacttcg acgacgccgc gtgggcgcag ggccgctgcg acgcgatagt   1920
ccgcagcggg gctgggacgg tgggtcggac ccaaatcgca cgccggtcgg ctgcggtgtg   1980
gacagacggc tgtgttgagg tgcttgcgga ctcgggcaac cgtaggccga gcacccgacc   2040
gcgtgcaaag gagtgattga atcattgaat gaaccattgt gtgcagaatc gatttcggga   2100
gtgttgccaa cacaagaaat atgcccaggg ttgtgtagaa gtttgcgtga atgtgatgaa   2160
gggaagccat acgctgaatt atcgtgacgt gtgtgagacg aagtgtcaca tcatacaccc   2220
aatttgagaa gctgtaccta ttagaagaat ttgtgagata cattaaaccc cttttggtac   2280
gtggtataat tgttatttgg gaagctgtaa acacgcagat cgttcctgag attgtcaatt   2340
acttttgtgg tgtttcctaa aggccgcatc actgcccgaa tcgagttgat ggcccgcaaa   2400
```

<210> SEQ ID NO 21
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Forward primer to detect insertion of the donor fragment into the targeted locus of Naga_100020g79

<400> SEQUENCE: 21
accctgtcgc acatcctcct                                                   20

<210> SEQ ID NO 22
<211> LENGTH: 22
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Reverse primer to detect insertion of the donor fragment into the targeted locus of Naga_100020g79

```
<400> SEQUENCE: 22
ttctgaagac cgtggtccca gc                                              22
```